(12) United States Patent
Akhavan-Tafti et al.

(10) Patent No.: US 6,635,437 B2
(45) Date of Patent: *Oct. 21, 2003

(54) COMPOUNDS, COMPOSITIONS AND METHODS FOR GENERATING CHEMILUMINESCENCE WITH PHOSPHATASE ENZYMES

(75) Inventors: Hashem Akhavan-Tafti, Brighton, MI (US); Zahra Arghavani, Brighton, MI (US); Renuka DeSilva, Northville, MI (US)

(73) Assignee: Lumigen, Inc., Southfield, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/054,417

(22) Filed: Jan. 22, 2002

(65) Prior Publication Data

US 2003/0023089 A1 Jan. 30, 2003

Related U.S. Application Data

(63) Continuation of application No. 09/539,816, filed on Mar. 31, 2000, now abandoned, which is a division of application No. 08/894,143, filed as application No. PCT/US97/00015 on Jan. 15, 1997, now Pat. No. 6,045,727, which is a continuation-in-part of application No. 08/683,927, filed on Jul. 19, 1996, now abandoned, and a continuation-in-part of application No. 08/585,090, filed on Jan. 16, 1996, now abandoned.

(51) Int. Cl.[7] .............................. C12Q 1/42; C09K 3/00; G01N 33/53
(52) U.S. Cl. .............................. 435/21; 435/4; 435/6; 435/7.9; 435/7.92; 435/968; 252/700; 436/172; 549/26; 549/359; 549/362; 549/366
(58) Field of Search .............................. 435/21, 4, 6, 7.9, 435/7.92, 968; 252/700; 436/172; 549/26, 359, 362, 366

(56) References Cited

U.S. PATENT DOCUMENTS

| | | | |
|---|---|---|---|
| 3,130,203 A | | 4/1964 | Buchel |
| 5,132,204 A | * | 7/1992 | Urdea et al. ................ 252/700 |
| 5,965,736 A | | 10/1999 | Akhavan-Tafti |
| 6,045,727 A | | 4/2000 | Akhavan-Tafti |
| 6,270,695 B1 | | 8/2001 | Akhavan-Tafti |

FOREIGN PATENT DOCUMENTS

WO  WO 00/15618  3/2000

OTHER PUBLICATIONS

M. Kitamura, M. Maeda, A. Tsuji, J. Biolumin. Chemilumin., 10, 1–7 (1995).
M. Maeda, A. Tsuji, K.H. Yang, S. Kamada, Biolum. and Chemilum. Current Status, 119–22 (1991).
R.B. McComb, G.N. Bowers, S. Posen in Alkaline Phosphatase, Plenum Press, New York 1979, pp. 268–275, 332–334, 394–397, 410–413.
W. Miska, R. Geiger, J. Biolumin. Chemilumin., 4, 119–28 (1989).
J.K. Myers, T.s. Widlanski, Science, 262, 1451–3 (1993).
M. Nakazono, H. Nohta, K. Sasamoto, Y. Ohkura, Anal. Sci., 8, 779–83 (1992).
H. Sasamoto, M. Maeda, A. Tsuji, Anal. Chim. Acta, 306, 161–6 (1995).
K. Sasamoto, Y. Ohkura, Chem. Pharm. Bull., 38, 1323–5 (1991).
N. Ugarova, Y. Vosny, G. Kutuzova, I. Dementieva, Biolum. and Chemilum. New Perspectives, P. Stanley and L.J. Kricka, eds., Wiley, Chichester, 511–4 (1981).

* cited by examiner

*Primary Examiner*—Evelyn Mei Huang
(74) *Attorney, Agent, or Firm*—Richard S. Handley

(57) ABSTRACT

Novel heterocyclic compounds which generate chemiluminescence on reaction with a phosphatase enzyme are provided as well as a process for their preparation and intermediates useful therein. The compounds comprise a nitrogen, oxygen or sulfur-containing heterocyclic ring system bearing an exocyclic carbon—carbon double bond. The double bond is further substituted at the distal carbon with a phosphate group and an oxygen or sulfur atom-containing group. Novel compositions further comprising a cationic aromatic compound (CAC) in addition to the heterocyclic phosphate compound are provided. The addition of the CAC in the composition greatly increases the production of chemiluminescence and provides improved detection sensitivity. Compositions further comprising an anionic surfactant and a non-ionic surfactant provide additional improvements in detection sensitivity. The novel chemiluminescent compounds and compositions are useful in methods for producing light and in assays for phosphatase enzymes and enzyme inhibitors and in assays employing enzyme-labeled specific binding pairs.

42 Claims, 19 Drawing Sheets

COMPOUNDS, COMPOSITIONS AND METHODS FOR GENERATING CHEMILUMINESCENCE WITH PHOSPHATASE ENZYMES

CROSS REFERENCE TO RELATED APPLICATION

The present application is a continuation of application Ser. No. 09/539,816, filing date Mar. 31, 2000 now abandoned, which is a divisional application of Ser. No. 08/894,143, filing date Aug. 13, 1997 now U.S. Pat. No. 6,045,727. The '143 application resulted from National Stage Entry of PCT Application US97/00015 filed on Jan. 15, 1997. The latter PCT application is a continuation-in-part of U.S. application Ser. No. 08/683,927, filed on Jul. 19, 1996, now abandoned and a continuation-in-part of U.S. application Ser. No. 08/585,090, filed on Jan. 16, 1996, now abandoned.

FIELD OF THE INVENTION

The present invention relates to chemiluminescent compounds which react with phosphatase enzymes to generate light. In particular, the present invention relates to chemiluminescent compounds containing a heterocyclic ring group and an enol phosphate group which react with oxygen upon removal of a phosphate group with a phosphatase enzyme to produce an enolate which reacts with to produce chemiluminescence and a carbonyl compound.

The present invention further relates to compositions for generating chemiluminescence by reaction with a phosphatase enzyme. Chemiluminescent compositions comprise a first compound containing a heterocyclic ring group and an enol phosphate group and a second compound which acts to increase light production from the reaction of the phosphate compound with a phosphatase enzyme. The present invention relates to methods for generating light or chemiluminescence by the reaction of a phosphatase enzyme with a chemiluminescent composition. In particular, the present invention relates to improvements in such methods which substantially increase light emission.

The invention further relates to the use of the chemiluminescent reactions and compositions in assay methods for detecting phosphatase enzymes and for detecting phosphatase-labeled specific binding partners in immunoassays, nucleic acid probe assays and the like.

The present invention relates to a process for the preparation of chemiluminescent compounds which react with phosphatase enzymes to generate chemiluminescence. The present invention relates to novel intermediates useful in this process. In particular, the present invention relates to a process and intermediates for preparing chemiluminescent compounds containing a heterocyclic ring group and an enol phosphate group which react with oxygen upon removal of a phosphate protecting group to produce chemiluminescence and a carbonyl compound.

BACKGROUND OF THE INVENTION a. Chemiluminescent Detection of Phosphatase Enzymes.

Hydrolytic enzymes such as alkaline phosphatase are frequently used as markers or labels in enzyme-linked assays for biological molecules and other analytes of interest such as drugs, hormones, steroids and cancer markers. In addition, phosphatase enzymes, e.g. alkaline phosphatase (AP) and acid phosphatase (AcP), are clinically significant in their own right in human and veterinary diagnostics. Chemiluminescent detection of these enzymes offers a safe, convenient and sensitive means to provide a quantitative measure of the amount of enzyme in a sample or of the amount of an enzyme-labeled analyte or labeled specific binding partner for an analyte. Numerous chemiluminescent reaction schemes have been developed to quantitate the level of particular hydrolytic enzymes. Most of these schemes are complex and expensive, requiring multiple enzymes or several reagents. Commercial acceptance of most of such methods for large volume testing has been slow.

Applicant's co-pending U.S. patent application Ser. No. 08/585,090 which is fully incorporated herein by reference, discloses the chemiluminescent reaction of certain heterocyclic compounds bearing an enol phosphate group with a phosphatase enzyme. Light emission is enhanced in the presence of cationic surfactants allowing the phosphatase to be detected at levels of $10^{-18}$ to $10^{-19}$ mol.

Applicant's co-pending U.S. patent application Ser. No. 08/683,927 which is fully incorporated herein by reference, discloses the use of cationic aromatic compounds (CAC's) in conjunction with the chemiluminescent reaction of certain heterocyclic compounds bearing an enol phosphate group with a phosphatase enzyme to substantially increase the amount of light emitted. The detection limit of phosphatase enzymes is thereby dramatically lowered.

b. Chemically and Enzymatically Triggerable Dioxetanes. Stable 1,2-dioxetanes bearing a protected phenol group triggering group undergo a chemiluminescent decomposition upon removal of a protecting group (A. P. Schaap, T. S. Chen, R. S. Handley, R. DeSilva, and B. P. Giri, Tetrahedron Lett., 1155 (1987); A. P. Schaap, R. S. Handley, and B. P. Giri, Tetrahedron Lett., 935 (1987); A. P. Schaap, M. D. Sandison, and R. S. Handley, Tetrahedron Lett., 1159 (1987); and A. P. Schaap, Photochem. Photobiol., 47S, 50S (1988)). Enzymatically triggerable dioxetanes bear an aryloxide substituent which is blocked by an enzymatically removable protecting group. Reaction with a hydrolytic enzyme in an aqueous buffer reveals an aryloxide anion which accelerates the chemiluminescent decomposition rate of the dioxetane by orders of magnitude. Chemically triggerable dioxetanes bear an aryloxide substituent which is blocked by a protecting group which is removed by a simple chemical agent. An example is deprotection of an acetoxy dioxetane with hydroxide or a silyloxy dioxetane with fluoride. Numerous examples of such triggerable dioxetanes are disclosed, for example, in U.S. Pat. Nos. 4,857,652, 5,068,339, 4,952,707, 5,112,960, 5,220,005, 5,326,882 and in PCT applications WO96/24849, WO94/10258 and WO94/26726. However, an inherent disadvantage of some triggerable dioxetanes is their tendency to generate background chemiluminescence in the absence of enzyme through slow thermal decomposition or non-enzymatic hydrolysis.

c. Luminol Derivatives. A phosphate and a NAG derivative of luminol are known (K. Sasamoto, Y. Ohkura, Chem. Pharm. Bull., 38, 1323–5 (1991); M. Nakazono, H. Nohta, K. Sasamoto, Y. Ohkura, Anal. Sci., 8, 779–83 (1992)). Treatment of the luminol derivative with the appropriate enzyme liberates luminol which is reacted in a subsequent step with ferricyanide to produce light.

d. Luciferin Derivatives. Phosphate and galactoside derivatives of firefly luciferin are known (N. Ugarova, Y. Vosny, G. Kutuzova, I. Dementieva, Biolum. and Chemilum. New Perspectives, P. Stanley and L. J. Kricka, eds., Wiley, Chichester, 511–4 (1981); W. Miska, R. Geiger, J. Biolumin. Chemilumin., 4, 119–28 (1989)). Treatment of the firefly luciferin derivative with the appropriate enzyme liberates firefly luciferin which is reacted in a second step with luciferase and ATP to produce light.

e. Reactions Involving the Generation of Reducing Agents. Chemiluminescent methods involving the generation of a reducing agent from a phosphate ester catalyzed by alkaline phosphatase have been reported. (M. Maeda, A. Tsuji, K. H. Yang, S. Kamada, Biolum. and Chemilum. Current Status, 119–22 (1991); M. Kitamura, M. Maeda, A. Tsuji, J. Biolumin. Chemilumin., 10, 1–7 (1995); H. Sasamoto, M. Maeda, A. Tsuji, Anal. Chim. Acta, 306, 161–6 (1995)).The reducing agent causes a reaction between oxygen and lucigenin to produce light arising from the lucigenin. Representative reducing agents include ascorbic acid, glycerol, NADH, dihydroxyacetone, cortisol and phenacyl alcohol. These methods are distinguished from the present invention which involves the production of light from the deprotected fluorescent compound, not from lucigenin. The known methods of enzymatically generating a reducing agent for reaction with lucigenin all require a separate preliminary incubation step between the enzyme and the phosphate compound. This adds additional complexity and assay time.

U.S. Pat. No. 5,589,328 to Mahant discloses a chemiluminescent reaction whereby indoxyl esters, thioindoxyl esters and benzofuran esters are hydrolyzed by an enzyme and thereby generate superoxide. Luminescence is amplified by adding a chemiluminescence generating reagent such as lucigenin. Lucigenin produces chemiluminescence by reaction with superoxide.

f. Cooled Enzyme Methods. Numerous other chemiluminescent methods and assays for determining hydrolytic enzymes such as phosphatase enzymes through coupled enzyme reactions are known. A compilation of such methods is listed in A. Tsuji, M. Maeda, H. Arakawa, Anal. Sci., 5, 497–506 (1989). Other examples of dual enzyme chemiluminescent reactions are described in U.S. Pat. No. 5,306,621 and commonly assigned application Ser. No. 08/300,367. The former describes the enzymatic generation of a peroxidase enhancer to enhance the chemiluminescent oxidation of luminol with a peroxidase; the latter describes the enzymatic generation of a peroxidase enhancer to enhance the chemiluminescent oxidation of an acridancarboxylic acid derivative with a peroxidase.

With the exception of enzyme-triggered dioxetanes, each of the aforementioned methods suffers the drawback of requiring multiple reagents or enzymes in order to generate the luminescent signal. The added expense or operational complexity has hindered commercial acceptance of these methods in spite of their demonstrated exceptional detection sensitivity. Chemiluminescent methods for detecting and quantitating hydrolytic enzymes which achieve these levels of sensitivity but do not require additional enzymes or auxiliary reagents in addition to the enzyme substrate would be advantageous. The present invention provides such methods and compounds.

SUMMARY OF THE INVENTION

It is an object of the present invention to provide compounds for chemiluminescent detection of phosphatase enzymes which are thermally and hydrolytically stable at room temperature over an extended period of time and are cleaved by a phosphatase enzyme to cleave the phosphate moiety.

It is also an object of the present invention to provide novel compounds substituted at one terminus of the double bond with a nitrogen, oxygen or sulfur-containing heterocyclic ring group and further substituted at the other terminus of the double bond with an enzymatically cleavable phosphate ($O-PO_3^{2-}$) group which can be triggered to decompose with the generation of light.

It is a further object of the present invention to provide a method and compositions for generating chemiluminescence containing such novel compounds which can be triggered by a phosphatase enzyme.

It is yet another object of the present invention to provide compounds which have superior light-generating ability and provide significant advantages when used for the detection of phosphatase enzymes, and for use in immunoassays and the detection of enzyme-linked nucleic acids, antibodies, haptens and antigens by generally known methods which employ phosphatase labels for detection of analytes.

The above and other objects and advantages in accordance with the present invention are attained by a compound having the formula I:

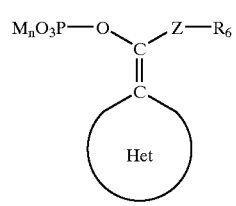

wherein Het is a heterocyclic ring system comprising at least one five or six-membered ring which comprises at least one heteroatom selected from N, O and S atoms, wherein Z is selected from the group consisting of O and S atoms, wherein $R_6$ is an organic group and wherein each M is independently selected from H and a cationic center and wherein n is a number which satisfies electroneutrality.

The above and other objects and advantages in accordance with the present invention are further attained by a reagent composition which produces chemiluminescence in the presence of a phosphatase enzyme which comprises in an aqueous solution: a compound of formula I and at least one surfactant enhancer in an amount effective to enhance the chemiluminescence.

The above and other objects and advantages in accordance with the present invention are further attained by a method for producing chemiluminescence which comprises reacting a phosphatase enzyme with at least one compound of formula I.

The above and other objects and advantages in accordance with the present invention are further attained by a method for detecting an analyte in a sample by a chemiluminescent assay procedure which comprises: reacting a phosphatase enzyme with at least one compound of formula I to produce chemiluminescence for detecting the analyte; detecting the chemiluminescence; and relating the amount of the chemiluminescence to the amount of the analyte.

The above and other objects and advantages in accordance with the present invention are further attained by a method of detecting an analyte in an assay procedure by a chemiluminescent reaction which comprises: providing a reagent composition which generates chemiluminescence in the presence of a phosphatase enzyme which comprises, in an aqueous solution, at least one compound of formula I which reacts with the phosphatase enzyme wherein in the compound of formula I, and a surfactant enhancer in an amount effective to enhance the chemiluminescence; reacting a phosphatase enzyme with the composition to produce chemiluminescence for detecting the analyte; and relating the amount of chemiluminescence to the amount of the analyte.

It is also an object of the present invention to provide compositions comprising a cationic aromatic compound and a compound of formula I which can be triggered to decompose with the generation of light.

It is a further object of the present invention to provide an improved method for generating chemiluminescence by reaction of a reagent composition with a phosphatase enzyme.

Still further, it is an object of the present invention to provide a composition and method which rapidly produces efficient chemiluminescence on reaction with a phosphatase enzyme.

The above and other objects and advantages in accordance with the present invention are attained by a reagent composition comprising a cationic aromatic compound and a compound of formula I.

The above and other objects and advantages in accordance with the present invention are further attained by a reagent composition which produces chemiluminescence in the presence of a phosphatase enzyme which comprises in an aqueous solution: a cationic aromatic compound, a compound of formula I which reacts with the phosphatase enzyme and, in combination, at least one anionic surfactant and at least one non-ionic surfactant in amounts effective to provide rapid generation of efficient chemiluminescence.

It is a further object of the present invention to provide a synthetic process and intermediates useful therein for the preparation of chemiluminescent compounds which react with phosphatase enzymes to generate light.

It is a further object of the present invention to provide a process and intermediates for preparing chemiluminescent compounds of formula I containing a heterocyclic ring group and an enol phosphate group which reacts with oxygen upon removal of a phosphate protecting group to produce light and a carbonyl compound.

It is a further object of the present invention to provide a process comprising phosphorylating an enolate of an ester or thioester compound to produce a phosphodiester or triester intermediate compound which is deprotected to a phosphate monoester salt.

DESCRIPTION OF THE PREFERRED EMBODIMENTS

Figure 1:
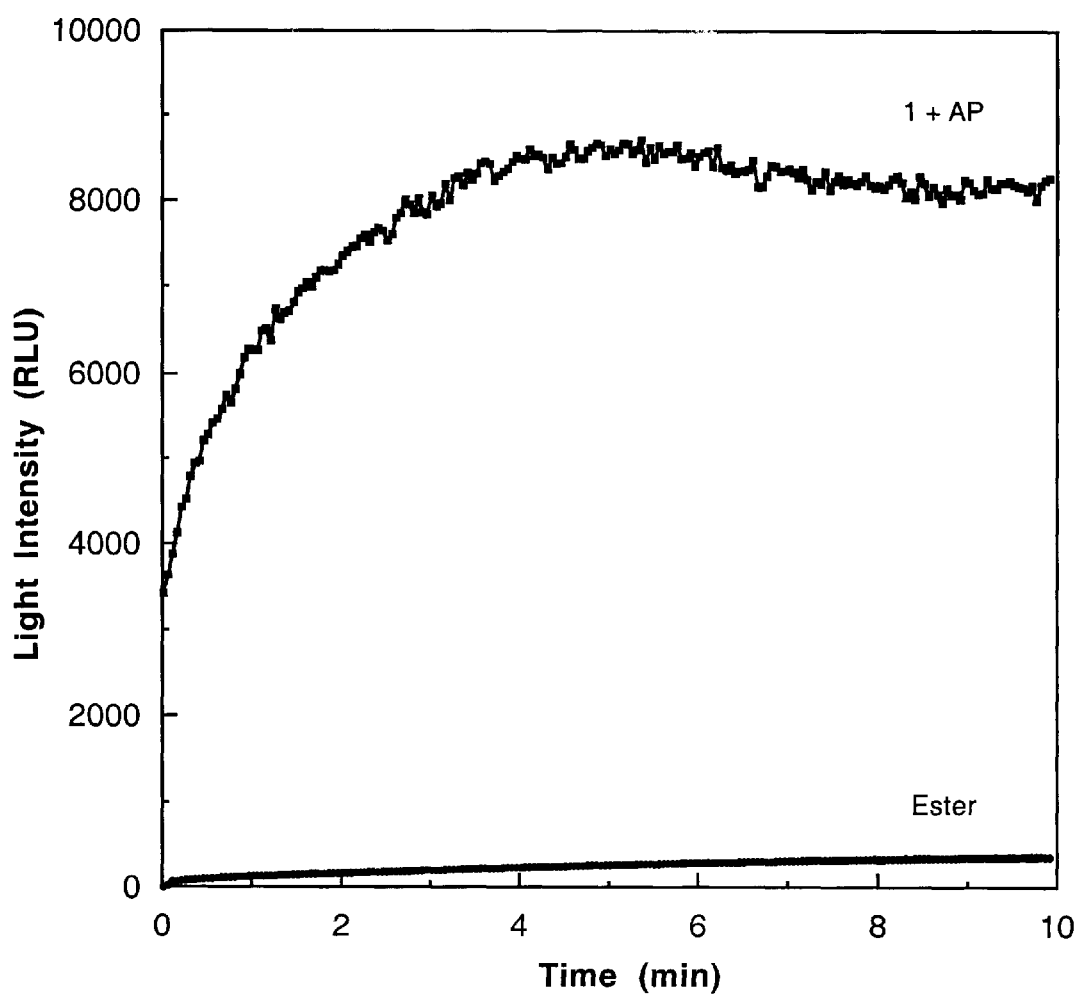
FIG. 1 is a graph showing the time profile of the chemiluminescence intensity emitted by 100 $\mu$L of a reagent consisting of a 0.33 mM solution of acridan phosphate 1 (9-(phenoxyphosphoryloxymethylidene)-10-methylacridan, disodium salt) in 0.1 M tris buffer, pH 8.5 and 0.01 mg/mL of the enhancer polyvinylbenzyltributylphosphonium chloride co-polyvinylbenzyltrioctylphosphonium chloride (containing about a 3:1 ratio of tributyl: trioctyl groups), (Enhancer A) triggered at 25° C. by addition of $8\times10^{-16}$ mol of alkaline phosphatase (AP). The figure also shows for comparison the chemiluminescence profile of the ester phenyl 10-methylacridan-9-carboxylate in a similar reagent composition containing the ester in place of 1.

It has been unexpectedly discovered as disclosed in Applicant's co-pending U.S. patent application Ser. No. 08/585,090 that certain novel compounds react with a phosphatase enzyme to generate easily detectable chemiluminescence. Compounds of the present invention which produce chemiluminescence in the presence of a phosphatase enzyme have the formula:

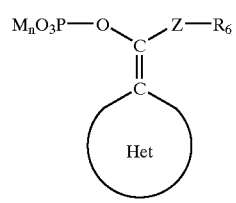

I wherein Het is a heterocyclic ring system comprising at least one five or six-membered ring which comprises at least one heteroatom selected from N, O and S atoms, wherein Z is an O or S atom, wherein $R_6$ is an organic group which allows the light to be produced and wherein each M is independently selected from H and a cationic center and wherein n is a number which satisfies electroneutrality. Reaction of the phosphatase with I in the presence of oxygen leads to formation of a carbonyl-containing compound VI in an electronically excited state (VI*) and the dephosphorylated product VII. Radiative decay of VI* leads to light emission.

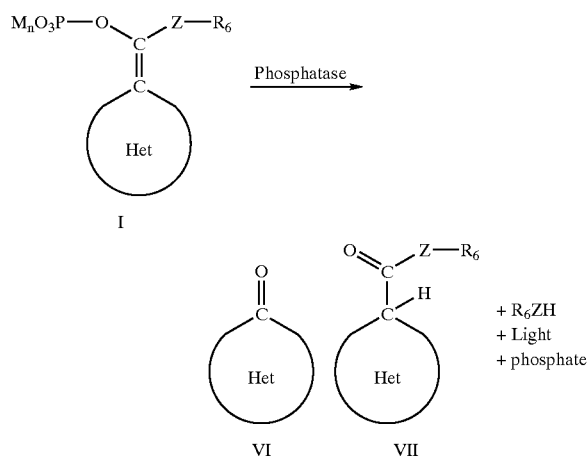

The heterocyclic ring system of I contains at least one heteroatom selected from N, O and S atoms and is in conjugation with the ring carbon bearing the exocyclic double bond. Preferred heterocyclic compounds include compounds of formulas II and III as depicted below and their double bond isomers or mixtures of the isomers.

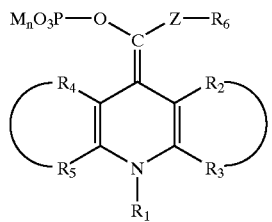

II

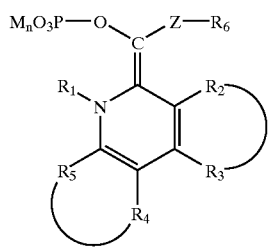

III where Z, M, n and $R_6$ are as defined above and $R_1$–$R_5$ are defined below.

Referring back to formula I, exemplary ring structures which can comprise the group Het include the structures below where the asterisk denotes the position of the exocyclic double bond. Without explicitly showing all possible substitution patterns, it is to be understood that each ring position can contain substituents other than hydrogen. Other heterocyclic ring compounds not specifically listed below but still falling within the scope of formula I will occur to the skilled artisan.

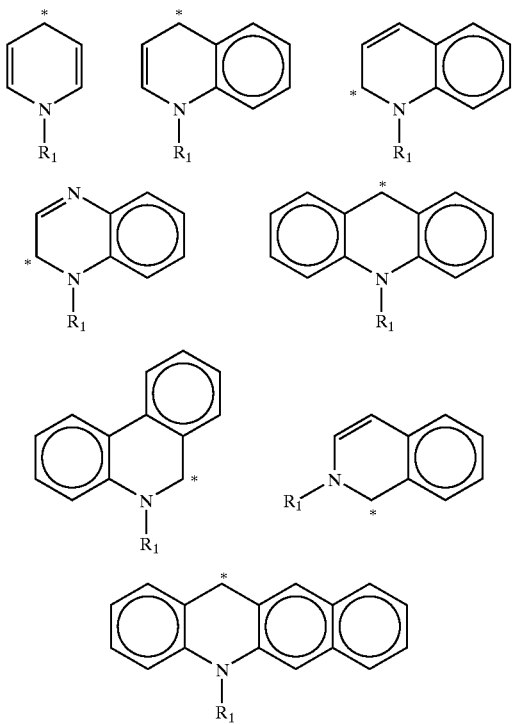

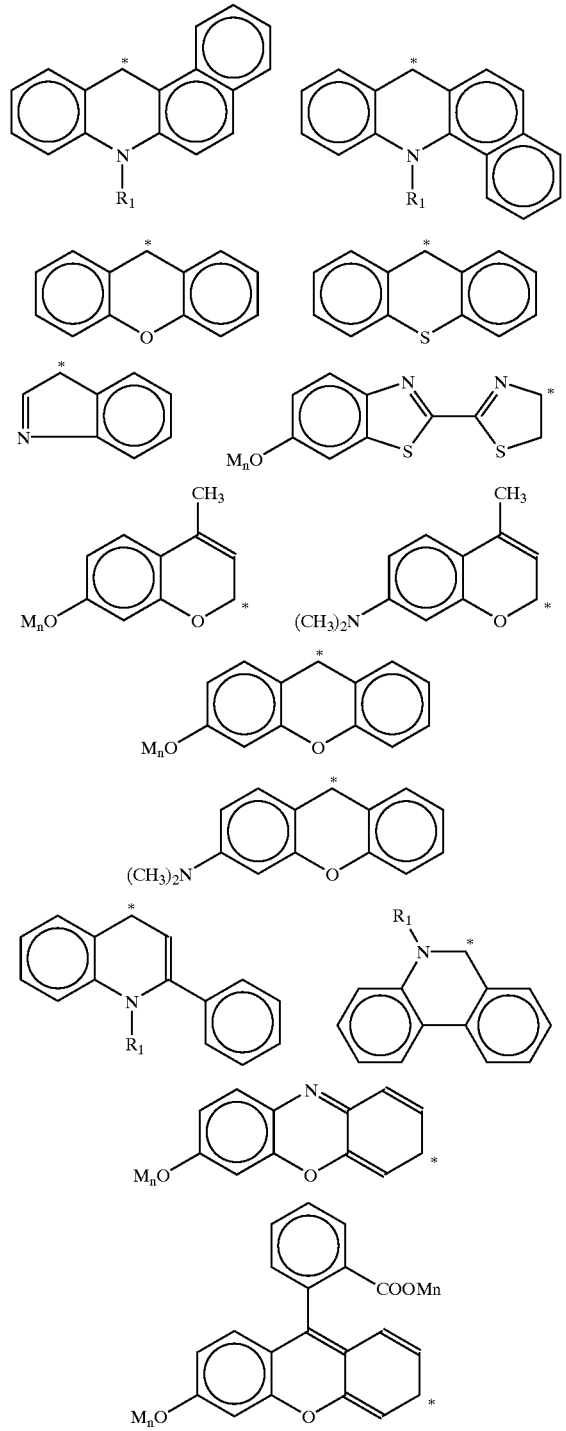

In all of the above compounds, the group $R_1$ is an organic group containing from 1 to 50 atoms selected from C, N, O, S, P and halogen atoms exclusive of the necessary number of H atoms required satisfy the valencies of the atoms in the group. The organic group is preferably selected from the group consisting of alkyl, substituted alkyl, aryl, substituted aryl and aralkyl groups. More preferred groups for $R_1$ include $C_1$–$C_4$ alkyl groups and benzyl groups.

In all of the above compounds, the groups $R_2$–$R_5$, which can be the same or different, each are H or a substituent group which permits the light to be produced and will generally contain from 1 to 50 atoms selected from C, N, O, S, P and halogen atoms. Representative substituent groups which can be present include, without limitation, alkyl, substituted alkyl, aryl, substituted aryl, aralkyl, alkenyl, alkynyl, alkoxy, aryloxy, halogen, amino, substituted amino groups, carboxyl, carboalkoxy, carboxamide, cyano, and sulfonate groups. Either or both pairs of adjacent groups, i.e. $R_2$–$R_3$ or $R_4$–$R_5$, can be joined together as a carbocyclic or heterocyclic ring system comprising at least one 5 or 6-membered ring which is fused to the ring bearing the exocyclic double bond. Such fused heterocyclic rings can contain 1 or more N, O or S atoms and can be substituted at the ring carbons with groups other than hydrogen such as those mentioned above.

Substituent groups can be incorporated in various quantities and at selected ring positions in order to modify the properties of the compound or to provide for convenience of synthesis of the final phosphate compound. Such properties include, for example, chemiluminescence quantum yield, rate of reaction with the enzyme, maximum intensity of light emission, duration of light emission, wavelength of light emission and solubility in the reaction medium. Specific substituents and their effects are illustrated in the specific examples below, which, however, are not to be considered limiting the scope of the invention in any way.

Each of the groups M independently comprise a hydrogen atom or a cationic center. A cationic center means a positively charged atom such as a sodium atom $Na^+$, a group of atoms such as an ammonium ion $NH_4^+$ or a portion of a molecule with one or more sites of positive charge. Examples of the latter include dicationic compounds described in U.S. Pat. No. 5,451,347 to applicant and polymeric compounds with multiple cationic groups as described in applicant's U.S. Pat. No. 5,393,469. the positive charge on a cationic center may take any unit value, i.e. 1, 2, 3 etc. Exemplary cationic centers include, without limitation, alkali metal ions, alkaline earth ions, quaternary ammonium ions and quaternary phosphonium ions and are present in the number required by their valence. If two groups are required to be present in the compound of formula I for electroneutrality, they can be the same or different. Preferred counter ions are the alkali metal ions.

As noted above, the organic group $R_6$ can be any group which allows or does not interfere with the light production and preferably contains from 1 to 50 atoms selected from C, N, O, S, P and halogen atoms and the necessary number of H atoms required satisfy the valencies of the atoms in the group. Groups which can function as the $R_6$ group include, without limitation, alkyl, substituted alkyl, aryl, substituted aryl and aralkyl groups. Substituent groups other than H atoms, such as ionic groups or polar groups, can be incorporated in various numbers and at selected positions on the carbon chain or ring of $R_6$ in order to modify the properties of the compound or to provide for convenience of synthesis of the final phosphate compound. Such properties include, for example, chemiluminescence quantum yield, rate of reaction with the enzyme, maximum intensity of light emission, duration of light emission, wavelength of light emission and solubility in the reaction medium. Specific substituents and their effects are illustrated in the specific examples below, which, however, are not to be considered limiting the scope of the invention in any way.

A preferred class of compounds have the formula IV below wherein Ar is an aryl ring group containing at least one carbocyclic or heterocyclic aromatic ring and which can be further substituted, Z is selected from O and S atoms, $R_1$ is as defined above, M is H or a monovalent or divalent cationic counter ion as defined above and n is 2 or 1, respectively.

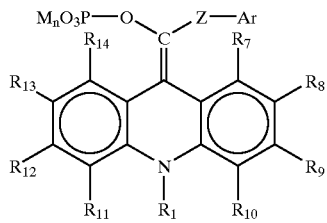

IV

The groups $R_7$ to $R_{14}$, which can be the same or different, each are H or a substituent group containing from 1 to 50 atoms selected from C, N, O, S, P and halogen atoms and which permit the light to be produced and can include, without limitation, alkyl, substituted alkyl, aryl, substituted aryl, aralkyl, alkenyl, alkynyl, alkoxy, aryloxy, halogen, amino, substituted amino groups, carboxyl, carboalkoxy, carboxamide, cyano, and sulfonate groups. Adjacent groups, e.g. $R_7$–$R_8$ or $R_8$–$R_9$, can be joined together as a carbocyclic or heterocyclic ring system comprising at least one 5 or 6-membered ring. It is preferred that $R_7$ to $R_{14}$ are selected from hydrogen and alkoxy groups such as methoxy, ethoxy, t-butoxy and the like. Especially preferred compounds have the formula V where Z is O or S and Ar is a phenyl group, a substituted phenyl group, a naphthyl group or a substituted naphthyl group and M and n are as defined above.

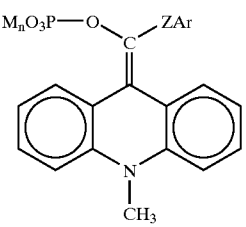

V

Another aspect of the present invention is the use of compounds of any of formulas I-V in a method to produce visible chemiluminescence by reaction with a phosphatase enzyme. Reaction of a compound of formula I-V with a phosphatase enzyme in an aqueous buffer solution produces easily detected chemiluminescence. Light intensity reaches a maximum level within minutes at room temperature when the reaction is conducted at alkaline pH. The reaction is conducted optionally in the presence of an enhancer.

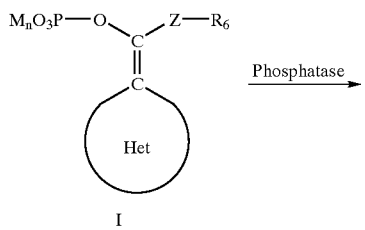

I

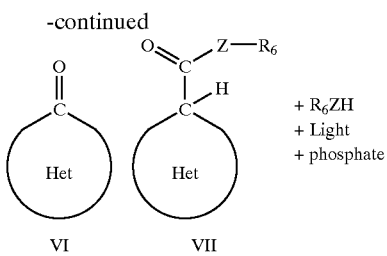

While not wishing to be bound by any specific mechanistic explanation for this discovery at this point, molecular oxygen is a necessary reactant and the reaction products are ketone VI, an ester or thioester VII, a compound of the formula $R_6ZH$ and phosphate ion. Light is emitted from the electronically excited state of VI. A necessary condition for the production of light is that the reaction produces sufficient energy to form the excited state of VI. If VI is fluorescent then chemiluminescence is produced directly from the reaction via emission from the excited state of VI. An especially surprising finding is that reaction of compounds of formula I with a phosphatase enzyme at moderately basic pH produces far more intense light emission than is produced by autoxidation of the enolate intermediate (the anion of VII) which would be expected to form upon cleavage of the phosphate group.

In a preferred method of producing chemiluminescence, a compound containing an acridan ring is reacted with alkaline phosphatase in an alkaline buffer with a pH between about 8 and 10 to produce a continuous chemiluminescence signal which commences upon reaction of the enzyme and the phosphate compound. The light intensity at any time point can be increased up to at least 40-fold by incorporation of at least one surfactant enhancer as will be described in more detail below.

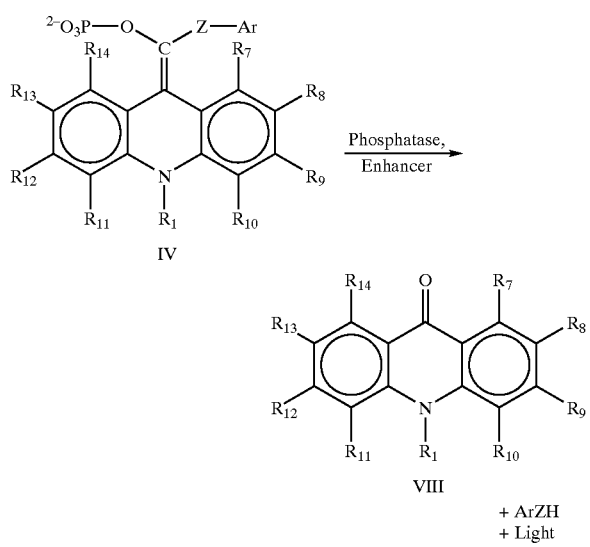

In a preferred method of producing light from the reaction of compound IV with a phosphatase enzyme, the reaction is performed at a temperature between 5° C. and 50° C., preferably between 20° C. and 40° C. in an aqueous buffer solution at a pH between 7 and 10.5, preferably between 8.5 and 10. Compound IV is used at a concentration between 1 μM and 20 mM, preferably between 10 μM and 1 mM. The enzyme is preferably an alkaline phosphatase or an alkaline phosphatase conjugate. Light is emitted from the excited state of VIII.

Compounds of the present invention typically produce light over a 100–200 nm wide band of emission, which exhibits a maximum intensity at wavelengths in the near ultraviolet to the visible region of the electromagnetic spectrum. Typical wavelengths of maximum intensity $\lambda_{max}$ in the range of 350–500 nm. It is contemplated that phosphate compounds of formula I bearing a covalently linked fluorophore not in conjugation with the double bond of the vinyl phosphate moiety could, upon formation of the excited product VI*, undergo intramolecular energy transfer resulting in emission at longer wavelengths from the excited state of the fluorophore.

More than one compound of formula I can be used concurrently in a method for producing light by the action of a phosphatase enzyme. It may be advantageous in some instances to simultaneously react two or more compounds of formula I with the phosphatase enzyme. When the two or more compounds have differing luminescent or physical properties, the combination of the two may be desirable to produce a light emitting reaction with characteristics not readily achievable through the use of any one compound. Examples of luminescent and physical properties which can differ between compounds I include emission spectrum, duration of light emission, enzyme turnover, rate of rise of emission to maximum, hydrophobicity/hydrophilicity and solubility. While particular luminescent properties can differ among the compounds of formula I in the present methods, the variation in properties does not detract from the basic utility of the compounds; selection of particular compounds with desirable properties can be made by virtue of the teachings and methods described herein.

Light emitted by the present method can be detected by any suitable known means such as a luminometer, x-ray film, high speed photographic film, a CCD camera, a scintillation counter, a chemical actinometer or visually. Each detection means has a different spectral sensitivity. The human eye is optimally sensitive to green light, CCD cameras display maximum sensitivity to red light, x-ray films with maximum response to either UV to blue light or green light are available. Choice of the detection device will be governed by the application and considerations of cost, convenience, and whether creation of a permanent record is required.

It is contemplated that fluorescent energy acceptors can be employed to shift the maximum emission to longer wavelengths (red-shifting). Various techniques for red-shifting emission are known in the art of chemiluminescent reactions and assays. Covalently linked fluorophores as described above are one example. Fluorescers can be added to the reaction solution as separate species. Fluorescers can be linked to an enhancer substance such as a cationic polymer or associated with an enhancer substance such as a micelle or polymer in order to bring the fluorescer in close contact to the compound. Alternately, the fluorescer can be provided in a non-fluorescent form which is convertible to the fluorescent form by removal of a phosphate group during the enzyme reaction period. Examples of the latter type of compound include fluorescein diphosphate, coumarin phosphates such as 4-methylumbelliferone phosphate, benzothiazole phosphates such as ATTOPHOS (JBL Scientific, San Luis Obispo, Calif.).

At least one enhancer compound can also be employed in the chemiluminescent reaction of the present invention, in order to increase the amount of light emitted. Enhancers which are effective in the present method can function by increasing the fraction of excited state product molecules which emit light, by increasing the fraction of product molecules which are formed in the excited state, by increasing the rate of reaction or turnover of the enzyme, by increasing the rate of a subsequent chemical reaction step, by improving the stability of the enzyme, by promoting the association of the enzyme with the compound of formula I, by inhibiting or preventing competitive non-luminescent side reactions or by any combination of these mechanisms. Enhancers will be used in an amount effective to enhance the chemiluminescence, preferably between 0.001 and 5 mg/mL in the final reaction solution, more preferably between 0.01 and 2.5 mg/mL.

Enhancer compounds that are effective in the practice of the present method are typically surfactant compounds, i.e. compounds which display surface active properties, e.g., surface tension depression, surface wetting or detergency. Surfactants comprise a hydrophilic region containing polar and/or ionic groups and a hydrophobic region containing mainly hydrocarbon groups or alkylenoxy groups or both. Surfactants are categorized as cationic, anionic, nonionic and zwitterionic and can be monomeric or polymeric. Cationic surfactant enhancers found useful in the practice of the present invention include polyvinyl type polymers with pendant quaternary phosphonium groups which are disclosed in U.S. Pat. No. 5,393,469 the disclosure of which is incorporated herein by reference. Exemplary polymers of this type include polyvinylbenzyltributylphosphonium chloride copolymer with polyvinylbenzyltrioctylphosphonium chloride and (polyvinylbenzyltributylphosphonium chloride). Polyvinyl type polymers with pendant quaternary ammonium groups are also useful as enhancers in the present invention. Examples of such polymers are disclosed in U.S. Pat. No. 5,112,960, the disclosure of which is incorporated herein by reference and include polyvinylbenzylbenzyldimethylammonium chloride and polyvinylbenzyltributylammonium chloride.

Another category of cationic surfactant enhancers found useful in the practice of the present invention are dicationic compounds bearing two quaternary ammonium or phosphonium groups as disclosed in U.S. Pat. No. 5,451,347 the disclosure of which is incorporated herein by reference. The compound (1-trioctylphosphoniummethyl-4-tributylphosphoniummethylbenzene dichloride) for example provides enhanced chemiluminescence when used in a method for producing light according to the present invention. Still other cationic surfactant enhancers useful in the practice of the present invention are monoquaternary ammonium salts e.g. cetyltrimethylammonium chloride or bromide and monoquaternary phosphonium salts such as cetyltrimethylammonium bromide.

Anionic surfactant enhancers include alkyl sulfates and alkylsulfonates. Nonionic surfactant enhancers include polyoxyethylenated alkylphenols, polyoxyethylenated alcohols, polyoxyethylenated ethers and polyoxyethylenated sorbitol esters. Zwitterionic surfactant enhancers include quaternary ammoniumalkyl phosphates and sulfonates. More extensive lists of exemplary structures of each category of surfactant can be found in any standard treatise on surfactants. Numerous representative member surfactants have been tested and found to be effective to varying degrees in increasing the amount or intensity of light produced compared to the amount produced in its absence. Cationic surfactants, in particular, quaternary ammonium and quaternary phosphonium salts have been found to be among the most effective enhancers.

As described above, surfactant enhancers can also have fluorescent groups covalently attached or associated through electrostatic or hydrophobic interactions.

In an alternate mode of performing the present chemiluminescent reactions, the chemiluminescent compound is reacted with a phosphatase enzyme in a buffer at a first pH in the range 5.0–9.5 for a first period of time ranging from a few seconds to less than about 10 min in the absence of an enhancer. Any light produced during this first period is neglected. Then a strongly basic trigger solution containing an enhancer is added at once and the burst of light measured either by measuring the peak intensity, or integrating for a second fixed time period or until light emission has ceased. It is desirable that the pH and amount of enhancer be selected so that all of the light is emitted in a short period of time, preferably about one minute or less. The pH of the trigger solution should be >11 and preferably above 12. Preferred bases are sodium hydroxide and potassium hydroxide. Enhancers useful in this mode of reaction are as identified in the foregoing discussion and will be used in an amount effective to enhance the chemiluminescence, preferably between 0.001 and 1 mg/mL in the final reaction solution.

This mode of generating the chemiluminescence may be advantageous in assays in which a large number of samples is processed simultaneously for measurement at a later time. Detection of acid phosphatase can also be performed in this manner. An optional step which can also be incorporated into such a chemiluminescent reaction or assay is to add an enzyme inhibitor to the reaction system after the first period of time to stop all further enzyme action.

Since the reaction is catalyzed by the phosphatase enzyme, exceedingly small quantities of the enzyme are sufficient to produce a detectable amount of light. Sensitivities of 1 attomol ($1\times10^{-18}$ mol) have been achieved. The ability to detect such small amounts of phosphatase enzymes make the present chemiluminescent technology suitable for analyses of many types of analytes using enzyme-linked assays.

The chemiluminescent reaction of the present invention provides a particularly effective reagent for detection of AP conjugates on polyvinylidene difluoride (PVDF) membranes, nylon membranes and on nitrocellulose filters and membranes. Surprisingly, it has been found that reaction of an antibody-AP conjugate on a PVDF membrane with a reagent composition containing compound 1

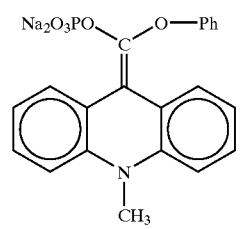

provides an intense luminescence which rises to a maximum level nearly instantly and maintains essentially constant intensity for at least 2 days. Detection on film and optimizing image intensity are thus particularly convenient.

Surprisingly, it has been found that light emission produced on PVDF membranes persists at useful levels for very long periods of time, exceeding a month. Art-known chemiluminescent reagents used in membrane-based detection schemes provide a luminescent signal with a time course which shows either a rapid decay, e.g. luminol with peroxidase which decays within 3–4 hours, or a slow rise and gradual decay as is the case with enzyme-triggered dioxetanes.

In another aspect, the present invention relates to a reagent composition for producing chemiluminescence by reaction with a phosphatase enzyme comprising an aqueous buffer with a pH between about 7 and about 10.5, a compound of formula I at a concentration of 0.01–10 mM and optionally at least one enhancer in an amount effective to enhance the chemiluminescence, preferably between 0.001 and 10 mg/mL. Formulations for chemiluminescent reaction with alkaline phosphatase can further comprise a magnesium or zinc salt at a concentration of 0.01–10 mM for increasing the activity of the enzyme.

A preferred reagent composition for producing chemiluminescence by reaction with a phosphatase enzyme comprises an aqueous buffer with a pH between about 7 and about 10.5, acridan phosphate of formula IV or V at a concentration of 0.01–10 mM and a surfactant enhancer in an amount effective to enhance the chemiluminescence, preferably between 0.001 and 10 mg/mL. The formulation further comprises a magnesium salt at a concentration of 0.01–10 mM.

It is preferred that the surfactant enhancer in the reagent composition is selected from the group consisting of polymeric cationic enhancers containing ammonium or phosphonium groups and dicationic enhancers containing ammonium or phosphonium groups. Especially preferred are polyvinyl polymers bearing a pendant trialkylphosphonium group on each monomeric unit and polyvinyl polymers bearing a pendant trialkylammonium group or a benzyldialkylammonium group on each monomeric unit. The amount and choice of enhancer can be selected for optimum performance in a given application as a matter of routine experimentation. A preferred composition for detection of AP or conjugates in solution comprises an amine buffer, pH 8.5 the compound 9-(phenoxyphosphoryloxymethylidene)-10-methylacridan, disodium salt, 0.1–1 mM, a magnesium salt, 0.1–1 mM, and Enhancer A (polyvinylbenzyltributylphosphonium chloride co-polyvinylbenzyltrioctylphosphonium chloride containing about a 3:1 ratio of tributyl: trioctyl groups), 0.01–0.1 mM. A preferred composition for detection of AP or conjugates on a membrane comprises an amine buffer, pH 9.6, the compound 9-(phenoxyphosphoryloxymethylidene)-10-methylacridan, disodium salt, 0.1–1 mm, a magnesium salt, 0.1–1 mM, and Enhancer A, 0.1–1 mM.

Applicant's co-pending U.S. patent application Ser. No. 08/683,927 discloses that adding a cationic aromatic compound (CAC) to the above reaction system greatly increases the quantity and/or intensity of light produced. Further, adding the CAC to the compound of formula I in the absence of the phosphatase enzyme does not lead to a corresponding increase in spontaneous (background) chemiluminescence since it is believed that the CAC exerts its effect on a dephosphorylated intermediate derived from compound I and not on compound I itself. Greatly increased sensitivity of detection of the phosphatase enzyme results by virtue of the increased signal/background. It is significant that light emission continues to arise from the excited state of VI and not from the CAC.

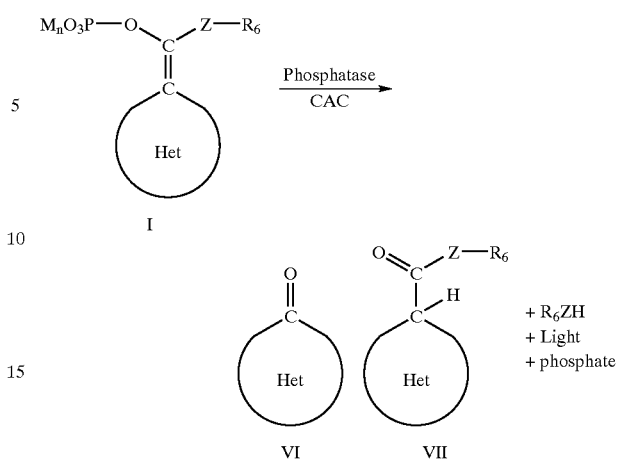

A variety of CACs have been found to function to increase the quantity and/or intensity of light produced. CACs are aromatic compounds bearing at least one positive charge either on the aromatic ring or ring system or residing on a substituent on one of the rings, provided that the substituent is in conjugation with the unsaturated ring atoms.

The CACs of the present invention are those compounds having oxidation/reduction potentials suitable for causing an increase in chemiluminescence in reactions of the invention. The suitability of compounds as CACs can be readily determined by means of the methods set forth in the specific examples below. Without being bound by any particular mechanistic interpretation, it appears that an intermediate product of dephosphorylation of I undergoes a redox reaction which can be reversible or irreversible. Molecular oxygen reacts with one or more of the reacting species in the reaction selected from the CAC, a reduced form of the CAC or the dephosphorylated intermediate of compound I or an oxidized or reduced form thereof to ultimately form an oxygenated reaction product derived from compound I. The oxygenated reaction product undergoes a chemiluminescent reaction, which is likely an O—O bond breaking reaction.

The CACs of the present invention can be a heteroaromatic ring compound comprising one or more isolated or fused aromatic rings containing at least one atom other than carbon (heteroatom), preferably one or more nitrogen atoms in which the positive charge is substantially localized on one or more of the heteroatoms. Examples of this class of CAC are cyanine dyes, thiacyanine dyes, carbocyanine dyes, thiacarbocyanine dyes, selenacarbocyanine dyes, azo dyes and acridinium derivatives of the formula:

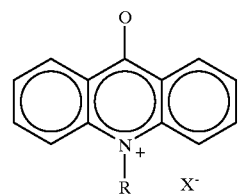

wherein Q is an electron withdrawing group, X— is a non-interfering anionic counter ion and R is an alkyl or aralkyl group each of which can optionally contain non-interfering substitutents. Acridinium derivatives in which some of the ring hydrogens are replaced by other substituting groups are also within the scope of functional CACs. The electron withdrawing group Q can be e.g. a halogen atom such as Cl, a cyano group, or a carbonyl group such as an ester group —COOR, a thioester group —COSR, an amide group —CONR$^1$R$^2$ or a sulfonimide group —CON(R)SO$_2$R'. Similarly the CAC can be a derivative of a phenanthridinium or phenanthrolinium compound.

The CACs of the present invention can be an aromatic ring compound comprising one or more isolated or fused carbocyclic aromatic rings bearing at least one cationic substituent containing at least one heteroatom, provided that the cationic site is in conjugation with the aromatic ring. In the latter class of CAC it is preferred that the heteroatom be a nitrogen or sulfur atom. Examples include Methylene Blue and Nile Blue.

The CACs of the present invention can bear more than one positive charge; e.g. dicationic compounds are within the scope of the invention. Exemplary compounds of this type include N,N'-dimethylbiacridinium dinitrate, commonly known as lucigenin and 1,1'-dimethyl-4,4'-bipyridinium dichloride, commonly known as methyl viologen dichloride, or paraquat dichloride.

Additional compounds which are useful as the CAC component of the present invention include, by way of illustration, compounds in Table I.

Table 1. CACs

Alcian Yellow, Basic Blue 41, Basic Blue 66, Basic Red 29,
3-Benzyl-5-(2-hydroxyethyl)-4-methylthiazolium chloride,
[2-[2-[2-Chloro-3-[(1,3-dihydro-1,3,3-trimethyl-2H-indol-2-ylidene)ethylidene]-1-cyclohexen-1-yl]ethenyl]1,3,3-trimethylindolium perchlorate, {IR-786 perchlorate},
trans-4-[4-(Dibutylamino)styryl]-1-methylpyridinium iodide,
5,5'-Dichloro-11-diphenylamino-3,3'-diethyl-10,12-ethylene thiatricarbocyanine perchlorate, {IR-140},
3,3'-Diethyl-9-methylthiacarbocyanine iodide,
1,1'-Diethyl-2,2' quinotricarbocyanine iodide,
3,3'-Diethylselenacarbocyanine iodide,
3,3'-Diethylthiacyanine iodide,
3,3'-Diethylthiadicarbocyanine iodide,
2-[4-(Dimethylamino)styryl]-3-ethylbenzothiazolium iodide,
3,6-Dimethyl-2-(4-dimethylaminophenyl)-benzothiazolium bromide,
3,4-Dimethyl-5-(2-hydroxyethyl)thiazolium iodide,
4-[2-[3-[(2,6-Diphenyl-4H-thiopyran-4-ylidene)ethylidene]-2-phenyl-1-cyclo-hexen-1-yl]ethenyl]-2,6-diphenyl-thiopyrylium tetrafluoroborate {IR-1040},
5-[3-Ethoxy-4-(3-ethyl-5-methyl-2(3H)-benzothiazolylidene)-2-butenylidene]-3-ethyl-2-[(3-ethyl-4,5-diphenyl-2(3H)-thiazolylidene)methyl]-4,5-dihydro-4-oxothiazolium iodide,
3-Ethyl-2-(2-hydroxy-1-propenyl)benzothiazolium chloride,
3-Ethyl-2-methylbenzothiazolium iodide,
3-Ethyl-2-methylbenzoxazolium iodide,
1-Ethyl-3-methyl-1H-imidazolium chloride,
Methylene Blue, Nile Blue A, and
Triphosphopyridine nucleotide, sodium salt hydrate Another aspect of the present invention, therefore, is the use of compounds of any of formulas I-V and a CAC in a method to produce detectable chemiluminescence by reaction with a phosphatase enzyme. Reaction of a compound of formula I-V with a phosphatase enzyme in the presence of a CAC in an aqueous buffer solution produces easily detected chemiluminescence from the excited state of VI.

Light intensity reaches a maximum level within seconds to minutes at room temperature when the reaction is conducted at alkaline pH.

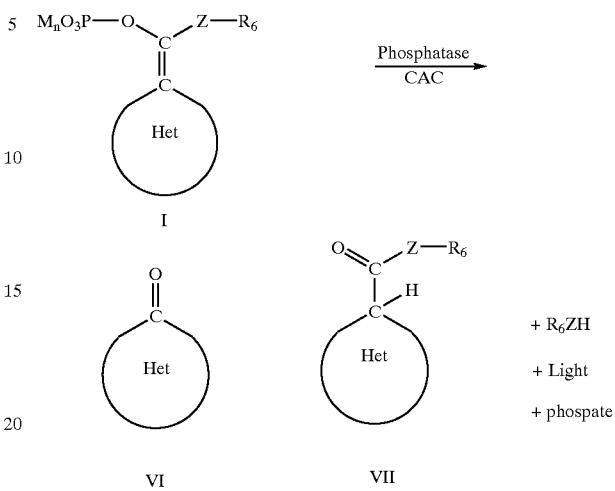

In a preferred method of producing chemiluminescence, a compound of formula IV containing an acridan ring is reacted in the presence of a CAC with alkaline phosphatase in an alkaline buffer with a pH between about 7 and 10.5 to produce a continuous chemiluminescence signal which commences upon reaction of the enzyme and rapidly reaches peak intensity. Further modifications and improvements in the light producing reaction can be realized by incorporation of an anionic surfactant and a non-ionic surfactant in combination as will be described in more detail below.

In a preferred method of producing light from the reaction of compound IV with a phosphatase enzyme and a CAC, the reaction is performed at a temperature between 5° C. and 50° C., usually between 20° C. and 40° C. in an aqueous buffer solution at a pH between 7 and 10.5, preferably between about 8 and 10. It is particularly convenient to conduct the reaction at ambient temperature, without the need to precisely regulate the temperature due to the relatively small influence of temperature on light intensity near ambient temperature. Compound IV is used at a concentration between 1 µM and 20 mM, preferably between 10 µM and 1 mM. The enzyme is preferably an alkaline phosphatase or an alkaline phosphatase conjugate.

More than one compound of formula I-V can be used concurrently in a method for producing light by the action of a phosphatase enzyme in the presence of a CAC. It can be advantageous in some instances to simultaneously react two or more compounds of formula I-V with the phosphatase enzyme and the CAC. When the two or more compounds have differing luminescent or physical properties, the combination of the two can be desirable to produce a light emitting reaction with characteristics not readily achievable through the use of any one compound. Examples of luminescent and physical properties which can differ between compounds I-V include emission spectrum, duration of light emission, enzyme turnover, rate of rise of emission to maximum, hydrophobicity/hydrophilicity and solubility.

Similarly, more than one CAC can be used concurrently in a method for producing light by the action of a phosphatase enzyme. The CAC is used at a concentration between $10^{-2}$ M and $10^{-9}$ M, preferably between about $10^{-4}$ M and $10^{-7}$ M. Desirable concentrations of a particular CAC for use in the present methods can be readily determined by means of the methods set forth in the specific examples below In another aspect, the present invention relates to a reagent composition for producing chemiluminescence by reaction with a phosphatase enzyme comprising an aqueous buffer with a pH between about 7 and about 10.5, a compound of formula I-V and a CAC in an amount effective to provide increased levels of chemiluminescence.

Additionally, it has been found that incorporation of certain additives into the reaction of a compound of formula I-V and a CAC with a phosphatase enzyme results in further desirable improvements in the light producing reaction. Yet another aspect of the present invention therefore is a reagent composition comprising a compound of formula I-V, a CAC, an effective amount of an anionic surfactant and an effective amount of a non-ionic surfactant. Anionic surfactants serve to substantially increase the speed with which maximum chemiluminescence intensity is reached. Non-ionic surfactants serve to substantially increase the amount or intensity of chemiluminescence which is generated. Use of the latter compositions is particularly advantageous in providing increased light emission which rapidly reaches and maintains peak light intensity.

In contrast to the methods of Applicant's co-pending application U.S. Ser. No. 08/585,090 in which cationic surfactants enhance the production of chemiluminescence, the incorporation of cationic surfactants, both monomeric and polymeric, are ineffective in promoting the chemiluminescent reaction which requires the presence of a CAC. In some cases, inclusion of cationic surfactants virtually extinguishes light production. The opposite effect of cationic surfactants in the present methods and compositions underscores the difference in the chemiluminescent reaction process which results from utilizing a CAC.

Anionic surfactants useful in compositions containing a CAC include alkyl sulfates and alkylsulfonates having an alkyl group of at least ten carbons. A preferred compound is sodium dodecyl sulfate (SDS). Anionic surfactants are preferably used in an amount from about 10 mg/mL to 10 µg/mL.

Non-ionic surfactants useful in compositions containing a CAC include polyoxyethylenated alkylphenols, polyoxyethylenated alcohols, polyoxyethylenated ethers and polyoxyethylenated sorbitol esters. Preferred non-ionic surfactants include TWEEN 20 and TRITON X-100. Non-ionic surfactants are preferably used in an amount from about 1.0% to about 0.001% by weight of the composition.

More extensive lists of exemplary structures of each category of surfactant can be found in any standard treatise on surfactants and are known to those of skill in the art. Numerous representative member surfactants have been tested and found to be effective to varying degrees in increasing the amount or intensity of light produced compared to the amount produced in its absence.

A still further aspect of the present invention is a reagent composition comprising a compound of formula I-V, a CAC, an effective amount of an anionic surfactant, an effective amount of a non-ionic surfactant and an effective amount of a background reducing agent which reduces chemiluminescence produced by the composition in the absence of a phosphatase enzyme (background chemiluminescence).

Background reducing agents are compounds which reduce chemiluminescence produced by the composition in the absence of a phosphatase enzyme. These agents can also function by preventing the accumulation of background chemiluminescence over a period of time. These agents can also function by improving the ratio of specific signal produced by reaction of the composition with a phosphatase enzyme to background chemiluminescence. Preferred compounds which are effective in reducing the amount of background chemiluminescence include sulfite salts such as lithium sulfite, sodium sulfite and potassium sulfite.

A preferred composition for detection of AP or conjugates in solution comprises an amine buffer, pH 8.5–9, 0.1–1000 µm lucigenin, 0.1–1.0 mM compound 5, 0.1–5 mg/mL SDS, 1–100 µg/mL $Na_2SO_3$, 0.01–0.1% (w/v) TWEEN 20 and 0.1–1.0 mM Mg salt. A preferred composition for detection of AP or conjugates on a membrane comprises an amine buffer, pH 8.5–9, 0.1–1000 µM lucigenin, 0.1–1.0 mM compound 5, 0.1–5 mg/mL SDS, 1–100 µg/mL $Na_2SO_3$, 0.01–0.1% (w/v) TWEEN 20 and 0.1–1.0 mM Mg salt.

Compositions which are effective in the present method can function by increasing the fraction of excited state product molecules which emit light, by increasing the fraction of product molecules which are formed in the excited state, by increasing the rate of reaction or turnover of the enzyme, by increasing the rate of a subsequent chemical reaction step, by improving the stability of the enzyme, by promoting the association of the enzyme with the compound of formula I, by inhibiting or preventing competitive non-luminescent side reactions or by other as yet unidentified mechanisms.

It is contemplated that fluorescent energy acceptors can be employed to shift the maximum emission to longer wavelengths (red-shifting). Various techniques for red-shifting emission are known in the art of chemiluminescent reactions and assays. The fluorescer can be covalently linked to a compound of formula I-V whereby the excited state of the corresponding compound VI can undergo an intramolecular energy transfer resulting in emission at longer wavelengths. Fluorescers can be added to the reaction solution as separate species. Fluorescers can be linked to an anionic or non-ionic surfactant which can form a micelle in order to bring the fluorescer in close contact to the light emitter. Alternately, the fluorescer can be provided in a non-fluorescent form which is convertible to the fluorescent form by removal of a phosphate group during the enzyme reaction period. Examples of the latter type of compound include fluorescein diphosphate, coumarin phosphates such as 4-methylumbelliferone phosphate and benzothiazole phosphates such as ATTOPHOS (JBL Scientific, San Luis Obispo, Calif.).

An important use of the present chemiluminescent methods is for detecting the presence or amount of an analyte in an assay procedure by a chemiluminescent reaction. The method comprises the steps of contacting a sample suspected of containing the analyte with a chemiluminescent compound of the present invention and a phosphatase enzyme, detecting the light produced in a qualitative method and, if quantitation is desired, relating the amount of light produced to the amount of the analyte. The relationship between light intensity and amount of analyte can be easily discerned by constructing a calibration curve with known amounts of the analyte. The chemiluminescent compound is typically used in a concentration of about $10^{-5}$ M to about $10^{-2}$ M, preferably between about $10^{-4}$ M and about $10^{-3}$ M. The phosphatase enzyme is preferably below about $10^{-9}$ M when detected in a solution. Typical samples which are analyzed by the chemiluminescent reaction method are body fluids such as blood, plasma, serum, urine and semen.

Analyte as used herein means a substance whose presence can be detected or quantified in a sample. Analytes which can be assayed by the present methods include phosphatase enzymes, in which case it would be unnecessary to add additional phosphatase enzyme. The analyte can be an inhibitor of a phosphatase enzyme. The analyte can be any of various classes of organic and biological molecules which can be detected in ligand-binder assays as are generally known in the art and include immunoassays, nucleic acid probe assays, cell receptor assays and the like. In these assays, the analyte is labeled with a phosphatase enzyme or can be specifically detected through phosphatase-labeled specific binding partners. The phosphatase can be incorporated directly as the label on the analyte binding compound. Alternately, the analyte binding compound can be bound to at least one phosphatase-labeled specific binding substance for the analyte binding compound. Alternately, the analyte binding compound can be labeled with at least one second specific binding substance which is then bound to a phosphatase-labeled binding partner for the second specific binding substance. The phosphatase enzyme can also be provided as a label on a ligand analog such as an enzyme-hapten conjugate in a competitive assay.

The phosphatase enzyme which can undergo the chemiluminescent reaction include alkaline phosphatase from a bacterial source such as *E. coli,* or a mammalian alkaline phosphatase or acid phosphatase from plant or mammalian sources. Conjugates of a phosphatase enzyme and a biological molecule can also be used in the method for producing chemiluminescence, the only proviso being that the conjugate display phosphatase activity, i.e. the ability to hydrolyze phosphate monoesters. Biological molecules which can be conjugated to one or more molecules of a phosphatase enzyme include DNA, RNA, oligonucleotides, antibodies, antibody fragments, antibody-DNA chimeras, antigens, haptens, proteins, lectins, avidin, streptavidin and biotin. Complexes including or incorporating phosphatase enzymes such as liposomes, micelles, vesicles and polymers which are functionalized for attachment to biological molecules can also be used in the methods of the present invention.

The reaction of a composition of the present invention with a phosphatase enzyme to produce chemiluminescence constitutes a rapid and highly sensitive method for detecting the presence or amount of the phosphatase enzyme. Use of the present method can therefore be made for the purpose of determining the presence or quantity of a phosphatase enzyme in a sample by measuring the amount or intensity of light produced by reaction of the sample with a compound of formula I. Such a determination can be used e.g. in measuring the level of alkaline phosphatase in blood serum as an indication of the status of a patient's liver function or as an index of certain disease conditions. Prostatic acid phosphatase is also useful as a clinical diagnostic index of prostate cancer.

Compositions of the present invention are useful for measurement of acid phosphatase (AcP) produced chemiluminescence which rapidly reaches maximum intensity within 2–5 sec and then decays within a short period of time. Even though the pH of the compositions is far higher than the optimal pH for AcP activity, it is possible to quantitate this enzyme with good sensitivity. Moreover, AcP could be measured in the presence of AP by means of this detection reagent. Since the chemiluminescent signal induced by AcP and AP display different kinetics, it is possible to simultaneously determine both AcP and AP activities in the same sample in one experiment.

A second area of application for the chemiluminescent measurement of phosphatase activity is in the detection and measurement of enzyme inhibitors. Inhibitors can act reversibly by acting as a substrate in competition with a second substrate such as the compounds of the present invention. Another mode of inhibition known as suicide inhibition acts irreversibly by deactivating the enzyme. Inhibitors of alkaline phosphatase include inorganic phosphate, levamisole and its racemic form tetramisole and other imidazo[1,2-b] thiazoles, L-phenylalanine and L-homoarginine and are identified in R. B. McComb, G. N. Bowers, S. Posen in *Alkaline Phosphatase,* Plenum Press, New York 1979, pp. 268–275, 332–334, 394–397, 410–413. Inhibitors of acid phosphatase include fluoride, molybdate, orthophosphate ions, tartrate, 4-(fluoromethyl)phenyl phosphate and 4-(fluoromethyl)phenyl phosphonate (J. K. Myers, T. S. Widlanski, Science, 262, 1451–3 (1993)). It is recognized that some substances are only inhibitory at some concentrations and can be only partially inhibitory.

Measurement of the quantity or characteristics of an inhibitor, such as the inhibition constant $K_i$, or half-life for inhibition, $t_{1/2}$, are made by measuring the enzyme activity of a sample containing the enzyme in question in the presence of a substrate producing a detectable product and a quantity of the inhibitor. In a method of detecting a phosphatase inhibitor according to the present invention, a compound of formula I produces light as the detectable product. Reaction of the phosphatase enzyme and chemiluminescent compound is made in the presence and absence of the inhibitor substance and the results are compared to determine the presence or amount of the inhibitor. The effect of the inhibitor can have one or more of any of three effects, a decrease in light intensity, a slower rate of rise of light intensity or a delay period before light emission begins.

A third area of application for the chemiluminescent measurement of phosphatase activity is in gene expression assays. Alkaline phosphatase and in particular an isozyme produced in the placenta which is excreted are useful as reporter genes (J. Alam, J. Cook, Anal. Biochem. 188, 245–54 (1990)). In this type of assay, a gene responsible for expression of a reporter enzyme is cloned into the genetic material of an organism via a plasmid in the vicinity of a promoter or enhancer sequence. The effect of the promoter or enhancer sequence on transcriptional activity is gauged by measuring the level of production of reporter enzyme.

Techniques for performing enzyme assays are well known. With the guidance provided by the examples as taught herein, variations of procedures for preparing samples, determining appropriate quantities and ratios of reagents, reaction times, constructing calibration curves and the like will be within the ability of one of ordinary skill in the art to devise as a matter of routine experimentation.

Since the reaction is catalyzed by the phosphatase enzyme, exceedingly small quantities of the enzyme are sufficient to produce a detectable amount of light. Sensitivities of 4 zeptomol ($4\times10^{-21}$ mol) have been achieved. The ability to detect such small amounts of phosphatase enzymes make the present chemiluminescent technology suitable for analyses of many types of analytes using enzyme-linked assays. Such analyses and assays require the ability to detect small quantities of phosphatase enzymes due to low abundance of the analyte in the sample to be analyzed or to limited sample quantity. In this type of assay, alkaline phosphatase is conjugated to one member of a specific binding pair. An example is a chemiluminescent enzyme-linked immunoassays, such as the so-called enzyme-linked immunosorbent assay or ELISA. Such assays are commonly used in manual format as well as on automated multi-test immunoassay systems. In a typical immunoassay, the analyte hapten, antigen or antibody is assayed by detecting the presence or amount of an enzyme-labeled specific binding partner for the analyte or an enzyme-labeled analog of the analyte. Various assay formats and the protocols for performing the immunochemical steps are well known in the art and do not constitute a part of the invention per se. These assays fall broadly into two categories. Competitive assays feature an immunological binding of a specific antibody with the analyte and an analyte analog, e.g. a detectably labeled analyte molecule. Sandwich assays result by the sequential or simultaneous binding of two antibodies, one of which is detectably labeled, with the analyte. The detectable enzyme-labeled binding pair so formed can be assayed with the compounds and methods of the present invention. Measurement can be performed with enzyme-labeled species attached to a solid surface or support including beads, tubes, microwells, magnetic particles, test strips, membranes and filters such as are in common use in the art. The detectable enzyme-labeled species can also be present free in solution or enclosed within an organized assembly such as a liposome in which case a lytic agent is employed to lyse the liposome and free the detectable enzyme.

Another exemplary use is the detection of proteins by the technique of Western blotting. A sample containing a protein of interest as the analyte is subject to electrophoretic separation. The separated proteins are transferred to a blotting membrane by capillary action or with the aid of an electric field. Such transferred protein is typically detected with a specific primary antibody and an enzyme-labeled secondary antibody which recognizes and binds to the primary antibody. Visualization of marker enzyme activity reflects the presence of the analyte protein. To adapt the methods of the present invention for Western blotting, an AP conjugated secondary antibody can be employed and AP activity measured with chemiluminescence using a compound of the present invention as the chemiluminescent reagent. Variations on this technique such as using biotinylated antibodies and avidin-AP are considered within the scope of assays able to be performed using the inventive methods.

In addition to the aforementioned antigen-antibody, hapten-antibody or antibody—antibody pairs, specific binding pairs also can include complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

A particularly useful application of the present detection methods is the detection of nucleic acids by the use of enzyme-labeled nucleic acid probes. Methods for analysis and chemiluminescent detection of nucleic acids using enzyme-labels, for example, hybridization assays, DNA detection in Southern blotting, RNA by Northern blotting, DNA sequencing, DNA fingerprinting, colony hybridizations and plaque lifts are all well established techniques. The enzyme label (e.g. AP) can be present as a direct conjugate with a probe oligonucleotide or capture oligonucleotide or it can be incorporated through indirect linking means using art-know methods. Examples of indirect linking means include using hapten-labeled oligonucleotides and anti-hapten-AP conjugates or biotinylated oligonucleotides and avidin-AP conjugates. Such nucleic acid assays can be performed on a blotting membrane or in solution using oligonucleotides attached to solid surfaces including beads, tubes, microwells, magnetic particles, test strips such as are known in the art.

Process for the Preparation of Compounds I-IV. A process and intermediates useful for the preparation of chemiluminescent phosphate compounds I-IV of the present invention was disclosed and embodied in the co-pending 585,090 application. For the purposes of elaborating additional exemplary methods and conditions, the following additional explanatory information is presented.

Briefly, the process involves reacting a heterocyclic ester or thioester compound VIII with a base to form an enolate of VIII; phosphorylating the enolate of VIII by reacting the enolate with a phosphorylating agent to form a protected enol phosphate IX and deprotecting the enol phosphate to form the enol phosphate salt compound I by reacting IX with at least one deprotecting agent in the presence of a cationic species M if the cationic species is not a part of the deprotecting agent.

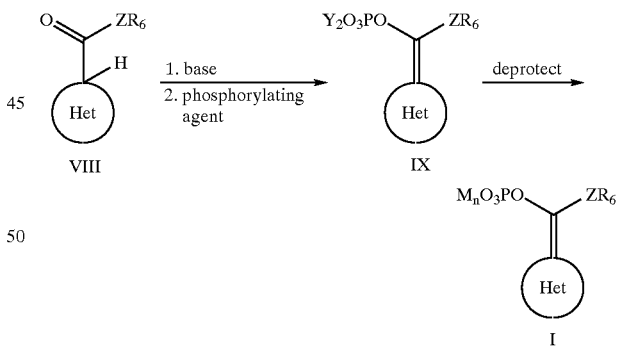

In one embodiment, the protected enol phosphate IX is formed by first reacting the enolate of compound VIII with a phosphorus oxyhalide compound $POW_3$, where W is a halogen atom selected from F, Cl, Br and I to form an enol dihalophosphate X. The intermediate enol dihalophosphate X is converted to protected enol phosphate IX by reaction with at least two equivalents of a hydroxylic compound Y—OH. The phosphate triester IX is then converted to phosphate salt I by reaction with at least one deprotecting agent in the presence of a cationic species M if the cationic species is not a part of the deprotecting agent.

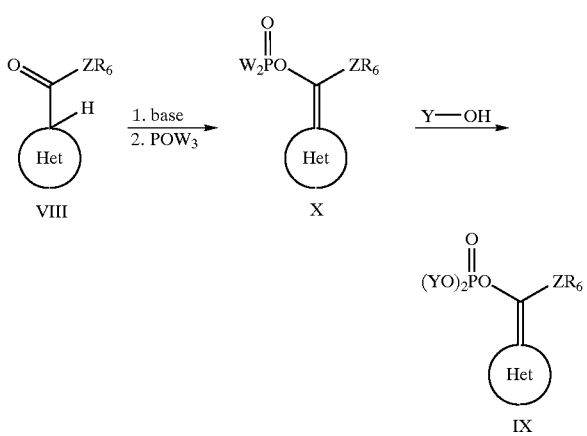

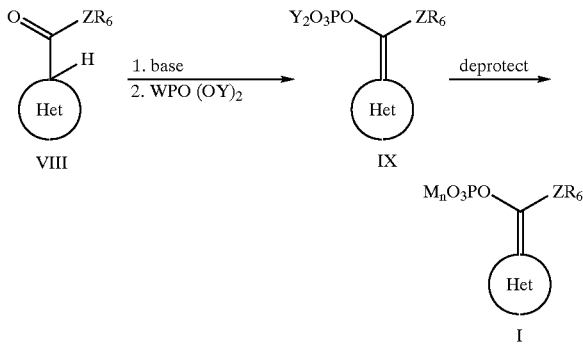

Preferably the halogen W is Cl. Compounds which can serve as the hydroxylic compound Y—OH include, without limitation, lower alcohols such as methanol and ethanol, substituted lower alcohols such as 3-hydroxypropionitrile ($HOCH_2CH_2CN$) and 2-trimethylsilylethanol, phenol, substituted phenols, benzyl alcohol and others as are generally known.

In another embodiment, the protected enol phosphate IX can be prepared directly from VIII by reacting the enolate of VIII a phosphorylating agent containing the protecting groups Y and having the formula W—$PO(OY)_2$.

The groups O—Y in this phosphorylating agent can include, by way of example, alkoxy such as $OCH_3$, $OCH_2CH_3$, and the like, substituted alkoxy such as cyanoethoxy ($OCH_2CH_2CN$) or trimethylsilylethoxy ($OCH_2CH^2Si(CH_3)_3$), phenoxy, substituted phenoxy, benzyloxy and others as are generally known to the skilled organic chemist. The two groups O—Y can also be combined together as a single group as occurs in the reagent

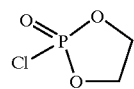

The enolate is formed by reacting the ester or thioester compound VIII with a strong base in a non-reactive organic solvent at a temperature in the range of −90 to 25° C. In a preferred mode, the reaction is performed at the temperature of a dry ice/acetone bath, nominally −78° C. for a time and then allowed to warm to 0 to 25° C. for a second time. Suitable solvents are those non-protic solvents which are compatible with the strong base required to form the enolate and include ethers and hydrocarbon solvents. The preferred solvent is tetrahydrofuran. The strong base and carbonyl compound VIII can be added to the reaction vessel in either order.

The phosphorylation step is performed in the same solution at a temperature in the range of about −78° C. to about 25° C. The phosphorylating agent, either $POW_3$ or WPO $(OY)_2$ is added in a controlled fashion so as not to cause the reaction solution to become hot. The phosphorylation agent is preferably accompanied by an amine base, preferably pyridine.

The deprotection step is accomplished by reacting the protected enol phosphate IX with a deprotecting agent in a quantity sufficient to cause removal of the protecting groups and in the presence of a cationic species M if the cationic species is not a part of the deprotecting agent. Two equivalents of the deprotecting agent are typically required, however for convenience, the deprotecting agent can be used in molar excess. Removal of the protecting groups can in some cases be performed one at a time. For example, in a compound of formula XI wherein the two Y groups together constitute the single group —$CH_2CH_2$—, and thereby form a five-membered ring, the first O—$CH_2$ bond can be cleaved by treatment with a cyanide salt. The resulting compound XII is further reacted with a base to cleave the second O—$CH_2$ bond and generate the salt I.

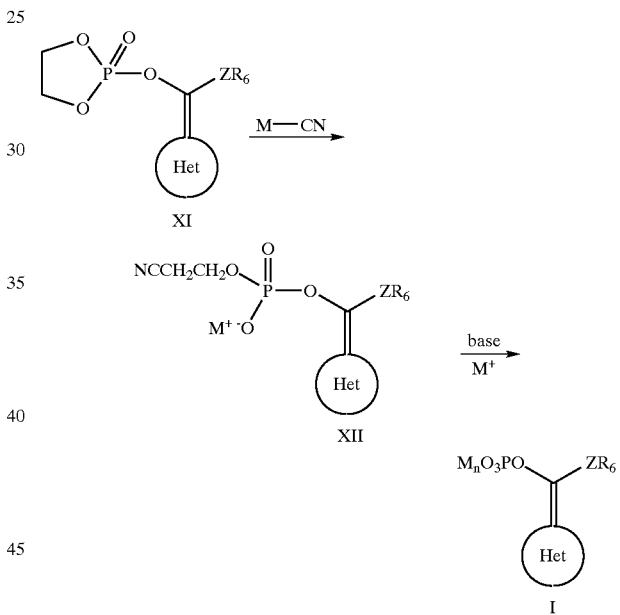

The choice of the deprotecting agent will be determined, in part, by the nature of the groups Y to be removed. The deprotecting agent must also not cause undesired side reactions such as hydrolysis of the vinyl ether or vinyl sulfide group or undesired changes to the heterocyclic group. Preferred deprotecting agents include organic and inorganic bases such as sodium hydroxide, potassium hydroxide, potassium carbonate, sodium methoxide, sodium ethoxide, potassium t-butoxide, ammonium hydroxide and the like. Other preferred deprotecting agents include nucleophilic agents such as cyanide ion, fluoride ion.

To the best of applicant's knowledge, compounds IX, X, XI and XII in which Het is a nitrogen or sulfur-containing heterocyclic group have not been prepared. An enol phosphate ester compound in which an oxygen-containing lactone ring is appended to the double bond is disclosed in U.S. Pat. No. 3,130,203. This compound however was prepared by a different process, not involving phosphorylation of an ester or thioester enolate.

EXAMPLES

The preparation and chemiluminescent reaction of the following compounds of formula I are described below for purposes of illustrating the invention in more detail.

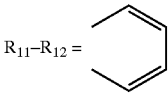

| Compound | R$_7$–R$_{14}$ | Z | R6 |
|---|---|---|---|
| 1 | all H | O | phenyl |
| 2 | all H | O | 3,5-difluorophenyl |
| 3 | R$_9$ = OCH$_3$ | O | phenyl |
| 4 | R$_9$ = Cl | O | 2,6-dimethylphenyl |
| 5 | all H | S | phenyl |
| 6 | R$_{11}$–R$_{12}$ = (butadiene) | O | phenyl |
| 7 | all H | S | 4-fluorophenyl |
| 8 | all H | S | 4-methoxyphenyl |
| 9 | all H | S | 2,6-dimethylphenyl |
| 10 | R$_8$, R$_{13}$ = F | S | phenyl |
| 11 | all H | S | trifluoroethyl |

-continued

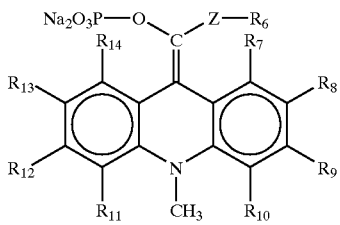

| Compound | R$_7$–R$_{14}$ | Z | R6 |
|---|---|---|---|
| 12 | all H | S | 4-chlorophenyl |
| 13 | all H | S | 2-naphthyl |

R$_7$–R$_{14}$ are H unless otherwise indicated.

Each of compounds 1–13 was prepared by the following synthetic scheme. It will be recognized that modifications to the reaction conditions can be made within the confines of the synthetic process described above in order to prepare these and other compounds of formula I.

Scheme 1

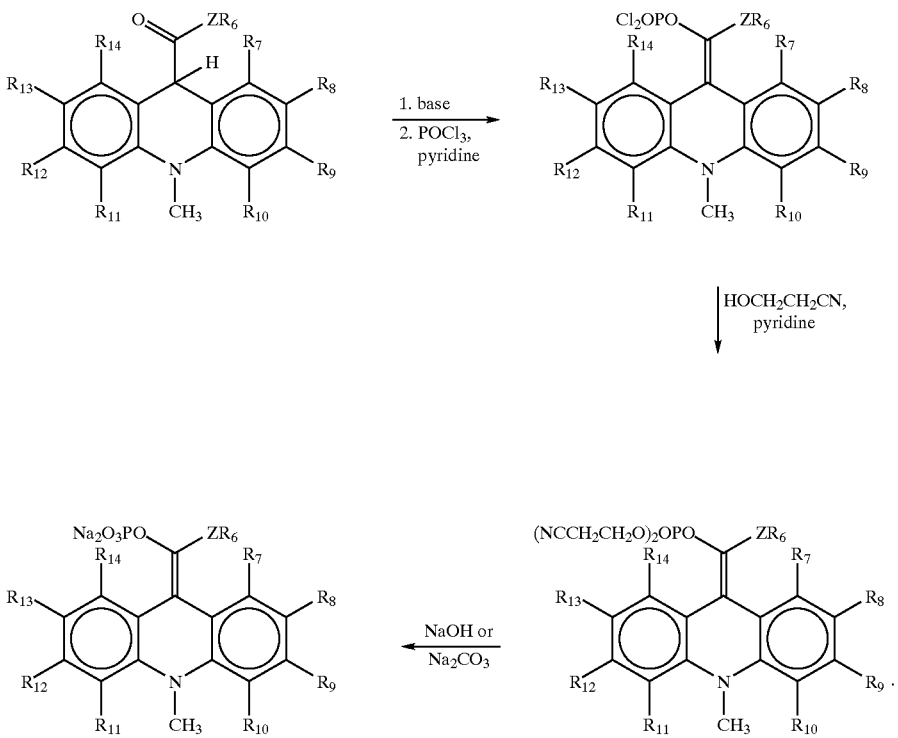

Example 1

Synthesis of Acridan Derivative 1

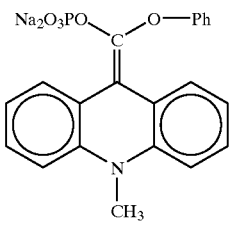

1 a. Phenyl acridine-9-carboxylate. Acridine-9-carboxylic acid (1 g, 4.1 mmol) was suspended in thionyl chloride (5 mL) and the reaction mixture was refluxed for 3 h. The solvent was removed under reduced pressure leaving a yellow solid which was dissolved in $CH_2Cl_2$ and pyridine (350 μL) under argon. This solution was cooled in an ice bath and a solution of phenol (0.78 g, 8.2 mmol) in $CH_2Cl_2$ was added dropwise. The reaction mixture was stirred overnight at room temperature. After evaporation of solvent, the residue was redissolved in ethyl acetate and washed with water. The organic layer was dried over $MgSO_4$ and concentrated to obtain a crude material which was chromatographed on silica gel (30% ethyl acetate/hexane) to yield the pure product as a yellow solid. $^1H$ NMR ($CDCl_3$) δ7.35–7.57 (m, 5H), 7.63–8.37 (m, 8H).

b. Phenyl 10-methylacridinium-9-carboxylate trifluoromethanesulfonate. Phenyl acridine-9-carboxylate (530 mg, 1.7 mmol) was dissolved in $CH_2Cl_2$ (5 mL) under argon and methyl triflate (1 mL, 8.8 mmol) was added. The solution was stirred overnight at room temperature to yield a thick yellow precipitate. This precipitate was filtered, washed with ether and dried to obtain the product as yellow crystals. $^1H$ NMR (acetone-$d_6$) δ5.22 (s, 3H), 7.47–7.71 (m, 5H), 8.23–9.07 (m, 8H).

c. Phenyl 10-methylacridan-9-carboxylate. Phenyl 10-methylacridinium-9-carboxylate trifluoromethanesulfonate (10 mg, 0.0216 mmol) was suspended in absolute ethanol (10 mL) and the mixture was refluxed for 15 min to obtain a clear solution. Ammonium chloride (88 mg, 1.6 mmol) was added by portions to the solution followed by zinc (108 mg, 1.6 mmol). Addition of zinc caused the yellow color of the solution to disappear immediately. The colorless solution was refluxed for 2 h. TLC of the reaction mixture showed complete conversion to a non polar material. The solution was filtered and precipitate was washed with ethanol (3×20 mL). The filtrate was concentrated to obtain an off-white solid which was redissolved in $CH_2Cl_2$ and washed with water (2×15 mL). The organic layer was dried over $Na^2SO^4$ and concentrated to yield the crude product which was purified by preparative TLC using (30% ethyl acetate:hexane). Pure product was obtained as an off-white solid. $^1H$ NMR ($CDCl_3$) δ3.38 (s, 3H), 5.16 (s, 1H), 6.89–7.37 (m, 13H); $^{13}C$ NMR ($CDCl_3$) δ33.29, 49.72, 112.93, 120.19, 121.36, 125.73, 128.67, 129.16, 129.26, 142.37, 151.04, 170.22.

d. 9-(Phenoxyphosphoryloxymethylidene)-10-methylacridan, bis(cyanoethyl) ester. A three-neck flask was purged with argon and charged with 5 mL of anhydrous THF and diisopropylamine (0.04 mL, 0.29 mmol). The flask was cooled in a dry ice-acetone bath. To this solution was added n-butyl lithium (0.116 mL, 0.29 mmol). After 20 min, a solution of the acridan ester from step (c)(70 mg, 0.22 mmol) in 5 mL of THF was added to this solution and stirring was continued for 30 min at −78° C. Finally a solution of $POCl_3$ (0.027 mL, 0.29 mmol) and pyridine (0.023 mL, 0.29 mmol) in 3 mL of THF was added and the dry ice bath was removed. After 45 min, pyridine (0.039 mL, 0.58 mmol) and 3-hydroxypropionitrile (0.094 mL, 1.16 mmol) was added and stirring maintained over night. Then it was filtered and solvent was removed from the filtrate. The residue was subjected to prep. TLC (80% ethyl acetate/hexane) to give the pure product; $^1H$ NMR ($CDCl_3$) δ2.35–2.54 (m, 4H), 3.47 (s, 3H), 3.79–3.90 (m, 2H), 3.98–4.08 (m, 2H), 6.825–7.45 (m, 12H), 7.80–7.83 (dd, 1H); $^{13}C$ NMR ($CDCl_3$) δ19.12, 19.24, 33.63, 62.19, 62.49, 88.72, 92.82, 112.40, 112.52, 115.83, 116.07, 119.68, 120.44, 120.71, 123.81, 126.69, 128.03, 128.27, 128.58, 130.09, 142.39, 143.06, 165.73, 202.09.

e. 9-(Phenoxyphosphoryloxymethylidene)-10-methylacridan, disodium salt (1). A solution of the bis (cyanoethyl) phosphate compound (2.897 g, 5.77 mmol) in 50 mL of acetone was purged with Ar for 30 min. An Ar-purged solution of 479 mg (12 mmol) of NaOH in 7.5 mL of water was added dropwise and the solution stirred over night. The precipitate which had formed was filtered, washed with 50 mL of Ar-purged acetone and air-dried. The yield was 3.473 g of 1 as a white solid which contained some water. $^1H$ NMR ($D_2O$) δ3.326 (s, 3H), 6.825–7.45 (m, 11H), 7.80–7.83 (d, 1H); $^{13}C$ NMR ($D_2O$) δ32.95, 102.86, 102.92, 112.30, 115.85, 120.68, 121.01, 122.35, 122.41, 122.62, 127.48, 127.66, 128.23, 129.66, 143.17, 143.32, 144.66, 156.01; $^{31}P$ NMR ($D_2O$) δ0.581 (rel. to ext. $H_3PO_4$).

Example 2

Synthesis of Acridan Derivative 2

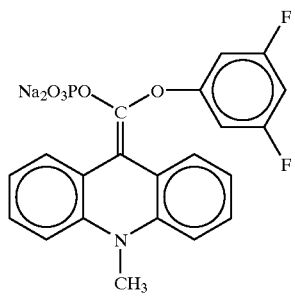

2 a. 3',5'-Difluoroohenyl acridine-9-carboxylate. Acridine-9-carboxylic acid (0.25 g) was suspended in 10 mL thionyl chloride and the reaction mixture was refluxed for 3 h. The solvent was removed under reduced pressure to obtain a yellow solid which was dissolved in $CH_2Cl_2$ and pyridine (0.22 g) under argon. A solution of 3,5-difluorophenol (0.16 g) in $CH_2Cl_2$ was added dropwise. The solution was stirred overnight at room temperature then diluted with more $CH_2Cl_2$ (100 mL) and washed with water (3×50 mL). The organic layer was dried over $Na_2SO_4$ and concentrated to obtain the product which was further purified by chromatography on silica gel (30% ethyl acetate/hexane) to yield the pure product as a creamy solid. $^1H$ NMR (CDCl3) δ6.84–7.09 (m, 3H), 7.67–8.37 (m, 8H).

b. 3',5'-Difluorophenyl 10-methylacridinium-9-carboxylate trifluoromethanesulfonate. The acridine ester from step (a) (0.20 g) was dissolved in CH$_2$Cl$_2$ (5 mL) under argon and methyl triflate (0.472 mL 7 eq.) was added. The solution was stirred overnight at room temperature to yield a thick yellow precipitate. This precipitate was filtered, washed with ether and dried to obtain the product as yellow crystals. $^1$H NMR (acetone-d$_6$) δ5.25 (s, 3H), 7.22–7.59 (m, 3H), 8.23–9.09 (m, 8H).

c. 3',5'-Difluorophenyl 10-methylacridan-9-carboxylate. The acridinium ester from step (b) (0.10 g) was dissolved in 10 mL of glacial acetic acid to obtain a yellow solution and zinc was added (1.30 g) causing immediate decolorization of the solution. After 5 min stirring at room temperature, TLC of the reaction mixture showed a nonpolar material. The acetic acid was decanted and the solid washed with CH$_2$Cl$_2$. The combined organic solutions were evaporated to obtain a crude solid which was redissolved in CH$_2$Cl$_2$ and washed with 2 or 3–50 mL portions of water. The crude material obtained after evaporation of CH$_2$Cl$_2$ was chromatographed on silica gel (20–30% ethyl acetate/hexane) to yield the pure product as a white solid. $^1$H NMR (CDCl$_3$) δ3.44 (s, 3H), 5.16 (s, 1H), 6.49–6.65 (m, 3 H), 6.99–7.36 (m, 8H).

d. 9-(3,5-Dimethylphenoxy)phosyloxymethylidene)-10-methylacridan. bis(cyanoethyl) ester. A three-neck flask was purged with argon and charged with 4 mL of anhydrous THF and diisopropylamine (0.0494 mL, 0.35 mmol). The flask was cooled in a dry ice-acetone bath. To this solution was added n-butyllithium (0.141 mL, 0.35 mmol). After 20 min, a solution of the acridan ester from step (c)(75 mg, 0.22 mmol) in 4 mL of THF was added dropwise to the LDA. The funnel was washed with an additional 4 mL of Ar-purged THF which was added to the reaction solution. Stirring was continued for 30 min at −78° C. Finally a solution of POCl$_3$ (0.034 mL, 0.35 mmol) and pyridine (0.057 mL, 0.35 mmol) in 4 mL of THF was added causing the brown solution to decolorize. The dry ice bath was removed and stirring continued for 15 min. A solution of pyridine (0.095 mL, 1.17 mmol) and 3-hydroxypropionitrile (0.080 mL, 1.17 mmol) in 4 mL of THF was added and stirring maintained over night. Then it was filtered and the solvent was removed from the filtrate. The residue was subjected to prep. TLC (55% ethyl acetate/hexane) from which a small amount of the pure product was isolated; $^1$H NMR (acetone-d$_6$) δ2.82 (m, 4H), 3.51 (s, 3H), 4.10–4.31 (m, 4H), 6.75–7.93 (m, 11H).

e. 9-(3,5-Dimethylphenoxy)phohosphoryloxymethylidene)-10-methylacridan. disodium salt (2). A solution of the bis(cyanoethyl)phosphate from step (d) 5 mg, 5.77 mmol) in 5 mL of methanol was purged with argon for 30 min with ice cooling. An Ar-purged solution of 6 mg of Na$_2$CO$_3$ in 0.5 mL of water was added dropwise and the solution stirred under argon over a weekend. The solvent was evaporated and the solid compound 2 dried under vacuum. $^1$H NMR (D$_2$O) δ3.34 (s, 3H), 6.66–8.09 (m, 11H).

Example 3

Synthesis of Acridan Derivative 3

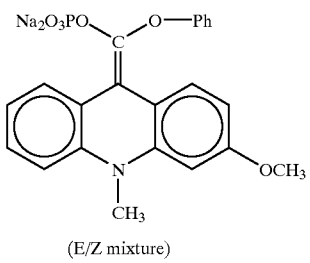

(E/Z mixture)

a. N-Methyl-3-methoxyisatin. 3-methoxydiphenylamine (250.2 g, 1.26 mol) dissolved in 900 mL of CH$_2$Cl$_2$ was added to a hot solution of 140 mL (1.6 mol) of oxalyl chloride in 1 L of CH$_2$Cl$_2$under an argon atmosphere. The addition was completed over a 2 hour period. Heating was discontinued during the addition since the reaction produced enough heat to maintain reflux. Stirring was continued at reflux temperature for another 30 min after adding the amine. The resulting brown solution was evaporated to remove excess oxalyl chloride. The brown solid was redissolved in 1.8 L of CH$_2$Cl$_2$ which was purged with argon. Aluminum chloride (359 g, 2.69 mol) was added in portions to the solution over a 45 min period while the mixture was stirred mechanically. The mixture became thick during the addition and began to reflux. Reflux was maintained for an additional hour after all of the AlCl$_3$ had been added. The cooled mixture was evaporated in vacuo and quenched with 4 kg of ice, ca. 500 mL of water and 240 mL of conc. HCl. The dark solid was carefully crushed to small particles while stirring at ice temperature for 2 h. The solid was then filtered off with suction and washed with a total of 8 L of water. Air drying produced an orange solid which was a mixture of isomeric isatins containing >90% of one isomer.

b. 3-Methoxyacridine-9-carboxylic acid. The isatin mixture from step (a) was refluxed in a 10% KOH solution in water for ca. 40 h. The solution was cooled to <60° C. and filtered through glass wool into a mixture of 480 mL of conc. HCl and 10 L of ice water which was stirred vigorously. The solid was suction filtered after 1 h and then washed with 8 L of water. The solid was air-dried over night and then dried under vacuum. $^1$H NMR (CD$_3$OD/NaOH) δ4.062 (s, 3H), 7.25–8.18 (m, 7H).

c. Phenyl 3-methoxyacridine-9-carboxylate. 3-Methoxyacridine-9-carboxylic acid (0.50 g) was suspended in 10 mL thionyl chloride (3–10 mL) and reaction mixture was refluxed for 3 h. The solvent was removed under reduced pressure to obtain a yellow solid which was dissolved in CH$_2$Cl$_2$ and pyridine (0.44 g) under argon. A solution of 2,6-difluorophenol (0.32 g) in CH$_2$Cl$_2$ was added dropwise. The solution was stirred overnight at room temperature then diluted with more CH$_2$Cl$_2$ (100 mL) and washed with water (3×50 mL). The organic layer was dried over Na$_2$SO$_4$ and concentrated to obtain the product which was further purified by chromatography on silica gel (30% ethyl acetate/hexane) to yield the pure product as a creamy solid. $^1$H NMR (acetone-d$_6$) δ4.08 (s, 3H), 7.39–8.29 (m, 12H).

d. Phenyl 3-methoxyacridan-9-carboxylate. Ammonium chloride (3.45 g, 64 mmol) and 4.2 g of zinc (64 mmol) were added to an Ar-purged suspension of 0.85 g (2.5 mmol) of the ester from step (c) in 50 mL of ethanol. The mixture was stirred for 2 h, filtered and the solids washed with $CH_2Cl_2$. The combined solutions were evaporated to dryness producing a white solid which was dissolved in ethyl acetate and washed with 3×25 mL of water. The product was used without further purification. $^1$H NMR (CDCl3) δ3.76 (s, 3H), 5.29 (s, 1H), 6.47–7.36 (m, 12H), 8.21 (br s, 1H).

e. Phenyl 3-methoxy-10-methylacridan-9-carboxylate. The acridan compound from the previous step (0.77 g, 2.3 mmol) was dissolved in $CH_2Cl_2$ and methyl triflate (3.8 g, 23 mmol) was added. TLC indicated complete methylation after stirring over night. The volatiles were evaporated and the residue purified by chromatography using 18% ethyl acetate/hexane to elute the column. The product contained 0.75 g of a sticky solid. $^1$H NMR (CDCl3) δ3.41 (s, 3H), 3.84 (s, 3H), 5.13 (s, 1H), 6.52–7.38 (m, 12H).

f. (E,Z)-9-(Phenoxy)phosphoryloxymethylidene)-3-methoxy-10-methylacridan, bis(cyanoethyl) ester. A solution of LDA was prepared essentially as described in Example 2d. After stirring 25 min at −78 C., a solution of the acridan ester from step 3e (95 mg, 0.26 mmol) in 4 mL of THF was added dropwise. Stirring was continued for 30 min at −78° C. Finally a solution of $POCl_3$ (0.04 mL) and pyridine (0.05 mL) in 4 mL of THF was added causing the yellow solution to decolorize. The dry ice bath was removed and stirring continued for 105 min. The solution was cooled in an ice bath and treated with pyridine (0.106 mL) and 3-hydroxypropionitrile (0.090 mL) in 4 mL of THF. After stirring for 20 h at room temperature, the reaction mixture was filtered and the yellow precipitate washed with THF. The reaction solvent was evaporated in vacuo and the residue combined with the precipitate. This material was subjected to prep. TLC (60% ethyl acetate/hexane) from which a small amount of the product was isolated as a mixture of double bond isomers; $^1$H NMR (acetone-d$_6$) δ2.75–2.82 (m, 4H), 3.52 (s, 3H), 3.82 (s), 3.91 (s), 4.00–4.26 (m, 4H), 6.47–7.96 (m, 12H).

g. (E,Z)-9-(Phenoxy)phosphoryloxymethylidene)-3-methoxy-10-methylacridan, disodium salt (3). The bis(cyano-ethyl)phosphate from step 3(f) was dissolved in 10 mL of MeOH purged with Ar and cooled in an ice bath. An Ar-purged solution of 11 mg of $Na_2CO_3$ in 1 mL of water was added dropwise and the solution stirred for 19 h. Another 3 mL of methanol was added and stirring continued for another 24 h to allow the deprotection to go to completion. The solvent was evaporated, the solid compound 3 washed with $CH_2Cl_2$ and dried under vacuum. $^1$H NMR ($D_2O$) δ3.24 (s, 3H), 3.66 (s), 3.83 (s), 6.35–8.07 (m, 12H).

Example 4

Synthesis of Acridan Derivative 4

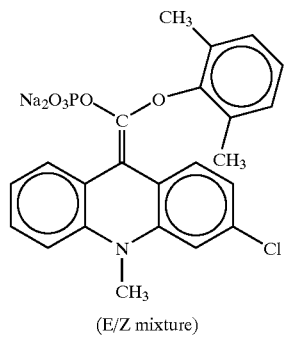

(E/Z mixture)

a. 3-Chloroisatin. 3-Chlorodiphenylamine (20 g, 0.98 mol) dissolved in 250 mL of $CH_2Cl_2$ was added to a solution of 14.0 g (0.11 mol) of oxalyl chloride in 150 mL of $CH_2Cl_2$ under an argon atmosphere. The solution was refluxed for 30 min. The resulting solution was evaporated to remove excess oxalyl chloride. The solid was redissolved in $CH_2Cl_2$ which was purged with argon. Aluminum chloride (54.48 g) was added in portions to the solution over a 45 min period while the mixture was stirred mechanically. The mixture became thick during the addition and began to reflux. Reflux was maintained for an additional hour after all of the AlCl had been added. The cooled mixture was evaporated in vacuo and quenched with 900 mL of 1M HCl in an ice bath. The solid was then filtered off with suction and washed with water. $^1$H NMR (CDCl$_3$) δ6.8–7.8 (m, 8H)

b. 3-Chloroacridinecarboxylic acid. The isatin product from step (a) was refluxed in 300 mL of 10% KOH solution in water for ca. 48 h. The solution was cooled and acidified to pH 2–3 with HCl. The yellow solid was suction filtered after 1 h and then washed with water. The solid was air-dried over night, washed with $CH_2Cl_2$ and then air-dried yielding 23.76 g of the acridine acid. $^1$H NMR (DMSO-d$_6$) δ7.72–8.30 (m, 7H).

c. 2',6'-Dimethylphenyl 3-chloroacridinecarboxylate. The acid (3.0 g) was esterified with 2,6-dimethylphenol (2.24 g, 1.5 eq.) and pyridine (1.98 mL, 2 eq.) in ca. 100 mL of $CH_2Cl_2$ at room temperature under nitrogen. The solvent was evaporated and the residue purified by column chromatography using 10–30% ethyl acetate/hexane which allowed the separation of the 1-chloro-(minor) and 3-chloro-isomers; $^1$H NMR (CDCl$_3$) δ2.430 (s, 6H), 7.20–7.28 (m, 3H), 7.60–7.75 (m, 3H), 8.28–8.50 (m, 4H).

d. 2',6'-Dimethylphenyl 3-chloro-10-methylacridinium-carboxylate trifluoromethanesulfonate. The acridine compound from the previous step (2.47 g, 6.7 mmol) was dissolved in $CH_2Cl_2$ and methyl triflate (3.8 mL, 5 eq.) was added. TLC indicated complete methylation after stirring over night. The volatiles were evaporated and the residue purified by chromatography using 5% ethyl acetate/hexane to elute the column. The product was recrystallized from $CH_2Cl_2$/hexane yielding 1.7 g of white crystals.

e. 2',6'-Dimethylphenyl 3-chloro-10-methylacridan-carboxylate. Ammonium chloride (2.91 g, 64 mmol) and 3.56 g of zinc (64 mmol) were added to an Ar-purged suspension of 2.00 g (5.4 mmol) of the ester from step (c) in 50 mL of ethanol. The mixture was stirred for 2 h, filtered and the solids washed with $CH_2Cl_2$. The combined solutions were evaporated to dryness producing a white solid. The product was used without further purification. $^1H$ NMR ($CDCl_3$) δ1.746 (s, 6H), 3.400 (s, 3H), 5.152 (s, 1H), 6.88–7.04 (m, 7H), 7.26–7.39 (m, 3H).

f. (E,Z)-9-(2, 6-Dimethylphenoxy)phosphoryloxymethylidene)-3-chloro-10-methylacridan, bis(cyanoethyl) ester. The acridan ester (0.100 g, 0.29 mmol) from step (e) was added to a solution of LDA (0.44 mmol) in 10 mL of THF. After stirring 30 min at −78 C., a solution of $POC_3$ (42 μL) and pyridine (47 μL) in 4 mL of THF was added. The dry ice bath was removed and stirring continued for 30 min. TLC (30% ethyl acetate/hexane) showed that the starting material was completely reacted. The solution was cooled in an ice bath and treated with pyridine (117 μL) and 3-hydroxypropionitrile (94 μL) in 4 mL of THF. After stirring over night at room temperature, the precipitated was filtered away and the reaction solvent evaporated. The residue was subjected to prep. TLC (60% ethyl acetate/hexane) from which the isomeric products was isolated; $^1H$ NMR ($CD_3OD$) δ(1.91 (s), 1.95 (s), combined 3H), (2.03 (s), 2.04 (s), combined 3H), 2.69–2.76 (m, 4H), (3.52 (s), 3.59 (s), combined 3H), 4.16–4.34 (m, 4H), 6.97–7.65 (m, 10H).

g. (E, Z)-9-(2,6-Dimethylphenoxy)phosphoryloxymethylidene)-3-chloro-10-methylacridan, disodium salt (4). The bis(cyanoethyl)phosphate from the step above is dissolved in 10 mL of methanol purged with argon and then cooled in an ice bath. An Ar-purged solution of 11 mg of $Na_2CO_3$ in 1 mL of water is added dropwise and the solution stirred under argon until the deprotection has gone to completion. The solvent is evaporated, the solid washed with $CH_2Cl_2$ and dried under vacuum to produce 4.

Example 5

Synthesis of Acridan Derivative 5

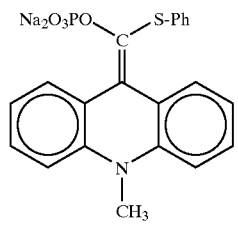

a. 9-(Phenythiophosphoryloxymethylidene)-10-methylacridan, bis(cyanoethyl) ester. Phenyl 10-methylacridan-9-thiocarboxylate (70 mg, 0.2 mmol) was added to a solution of LDA (0.24 mmol) in THF. After stirring 30 min at −78 C., a solution of $POCl_3$ (25 μL) and pyridine (21 μL) in 4 mL of THF was added. The dry ice bath was removed and stirring continued for 30 min. TLC (30% ethyl acetate/hexane) showed that the starting material was completely reacted. The solution was cooled in an ice bath and treated with pyridine (210 μL) and 3-hydroxypropionitrile (44 μL) in 4 mL of THF. After stirring over night at room temperature, the precipitated pyridine-HCl was filtered away and the reaction solvent evaporated in vacuo. The residue was subjected to prep. TLC (ethyl acetate) from which the product was isolated; $^1H$ NMR ($CDCl_3$) δ2.4–2.6 (m, 4H), 3.521 (s, 3H), 3.8–4 (m, 2H), 4.0–4.1 (m, 2H), 6.9–7.2 (m, 4H), 7.22–7.5 (m, 7H), 7.75–8 (dd, 2H).

b. 9-(Phenylthiophosphoryloxymethylidene)-10-methylacridan, disodium salt (5). A solution of the bis(cyanoethyl) phosphate compound (0.59 g, 1.21 mmol) in 50 mL of acetone was purged with argon for 30 min. An Ar-purged solution of 104 mg (2.6 mmol) of NaOH in 10 mL of water was added dropwise and the solution stirred under argon over night. The precipitate which had formed was suction filtered, washed with 50 mL of Ar-purged acetone and air-dried. The yield was 0.50 g of 5 as a slightly yellow solid which contained a slight amount of acetone. $^1H$ NMR ($D_2O$) δ3.36 (s, 3H), 6.9–7.4 (m, 11H), 7.75–7.8 (d, 1H), 8.2–8.22 (d, 1H); $^{31}P$ NMR ($D_2O$) δ1.85 (rel. to ext. $H_3PO_4$).

Example 6

Synthesis of Benz[c]acridan Derivative 6

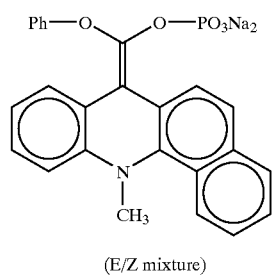

(E/Z mixture)

a. Benz[c]acridine-7-carboxylic acid. 1-Naphthylphenylamine (10 g, 46 mmol) dissolved in 25 mL of $CS_2$ was refluxed with 4.8 mL (55 mmol) of oxalyl chloride under argon. The resulting brown solution was evaporated to remove excess oxalyl chloride. The brown solid was dissolved in 60 mL of $CS_2$ which was purged with argon. $AlCl_3$ (21.47 g, 160 mmol) was added in portions to the solution while the mixture was stirred. The mixture became thick during the addition and began to reflux. Reflux was maintained for two more hours after all of the $AlCl_3$ had been added. The cooled mixture was evaporated in vacuo and quenched with 1 M HCl and ice. The dark solid was carefully crushed to small particles and the solid filtered off with suction and washed with water.

The isatin product was refluxed in a 10% KOH solution in water over night. The solution was cooled to <60° C. and neutralized with 6 M HCl and ice. The solid was suction filtered, washed with water and air-dried. $^1H$ NMR (DMSO-$d_6$) δ7.80–8.13 (m, 8H), 8.36–8.39 (d, 1H), 9.38–9.40 (m, 1H).

b. Phenyl benz[c]acridine-7-carboxylate. Benz[c]acridine-7-carboxylic acid (6.0 g) was suspended in 75 mL thionyl chloride (3–10 mL) and reaction mixture was refluxed for 4 h. The solvent was removed under reduced pressure and the product dissolved in 75 mL of $CH_2Cl_2$. Pyridine (8.9 mL) and phenol (2.27 g) were added and the solution was stirred for 3 days at room temperature under Ar. Purification was effected by chromatography on silica gel (50% $CH_2Cl_2$/hexane) to yield 3.05 g of the pure product as a light brown solid. $^1H$ NMR ($CDCl_3$) δ7.40 (t, 1H), 7.48–7.59 (m, 4H), 7.71–8.01 (m, 7H), 8.259 (d, 1H, J=7.8 Hz), 8.465 (d, 1H, J=7.8 Hz), 9.54–9.57 (m, 1H).

c. Phenyl benz[c]acridan-7-carboxylate. Ammonium chloride (10 g) and 10 g of zinc were added to an Ar-purged suspension of 1.0 g of the ester from step (b) in ethanol. The mixture was stirred for 2 h, filtered and the solids washed with CH$_2$Cl$_2$. The combined solutions were evaporated to dryness producing a white solid which was dissolved in ethyl acetate and washed with 3×25 mL of water. The product was purified by chromatography using 10% ethyl acetate/hexane. $^1$H NMR (CDCl$_3$) δ5.48 (s, 1H), 5.69–7.27 (m, 9H), 7.41–7.55 (m, 5H), 7.83–7.88 (m, 2H).

d. Phenyl 12-methylbenz[c]acridan-7-carboxylate. The acridan compound from the previous step (0.70 g) was dissolved in CH$_2$Cl$_2$ and methyl triflate (2.3 mL) was added. TLC indicated complete methylation after stirring over night. The volatiles were evaporated and the residue purified by chromatography using 5% ethyl acetate/hexane to elute the column. $^1$H NMR (CDCl$_3$) δ3.75 (s, 3H), 5.21 (s, 1H), 6.92–6.94 (d, 2H), 7.09–7.62 (m, 11H), 7.86–7.89 (dd, 1H), 8.23–8.26 (d, 1H); $^{13}$C NMR (CDCl$_3$) δ45.07, 49.99, 120.01, 121.23, 122.66, 123.51, 124.69, 125.30, 125.45, 125.84, 126.33, 126.97, 128.39, 128.64, 129.36, 134.89, 141.20, 147.09, 151.00, 170.89.

e. (E,Z)-9-(Phenoxy)phosphoryloxymethylidene)-12-methylbenz[c]acridan, bis(cyanoethyl) ester. A solution of LDA was prepared as described above. After stirring 25 min at –78 C., a solution of the benzacridan ester (0.30 g) in THF was added dropwise. Stirring was continued for 30 min at –78° C. Finally a solution of POCl$_3$ (0.123 mL) and pyridine (0.107 mL) in THF was added causing the deep red solution to become orange. The dry ice bath was removed and stirring continued for 1 h. The solution was cooled in an ice bath and treated with pyridine (0.213 mL) and 3-hydroxypropionitrile (0.180 mL) in THF. After stirring over night at room temperature, the reaction mixture was filtered and the precipitate washed with THF. The reaction solvent was evaporated in vacuo and the residue combined with the precipitate. This material was subjected to prep. TLC (60% ethyl acetate/hexane) from which a small amount of the product was isolated as a mixture of double bond isomers; $^1$H NMR (CDCl$_3$) δ2.44–2.52 (m, 4H), 3.81–4.10 (m, 7H), 6.89–8.24 (m, 15H).

f. (E,Z)-9-(Phenoxy)phosphoryloxymethylidene)-12-methylbenz[c]acridan, disodium salt (6). The bis (cyanoethyl)phosphate from the step above was dissolved in 10 mL of acetone purged with argon and then cooled in an ice bath. An Ar-purged solution (0.1 mL of 2M NaOH in water) was added dropwise and the solution stirred under Ar over night. The solid was filtered and the product compound 6 was washed with acetone and dried. $^1$H NMR (D$_2$O) δ3.52 (s, 3H), 6.85–6.90 (t, 1H), 7.03–7.06 (d, 2H), 7.15–7.23 (m, 3H), 7.33–7.48 (m, 5H), 7.72–7.75 (d, 1H), 7.87–7.89 (d, 1H), 8.10–8.17 (t, 2H).

Example 7

Synthesis of Acridan Derivative 7

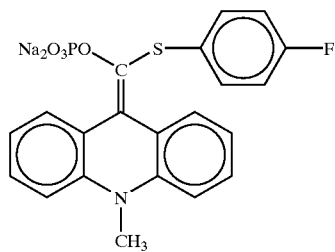

7 a. 4'-Fluorophenyl acridine-9-thiocarboxylate. Acridine-9-carboxylic acid (10 g, 45 mmol) was suspended in thionyl chloride (ca. 100 mL) and the reaction mixture was refluxed for 2 h. The solvent was removed under reduced pressure leaving a yellow solid which was dissolved in 100 mL of CH$_2$Cl$_2$ under argon. 4-Fluorothiophenol (5.25 mL, 49 mmol) was added followed by 30 mL of pyridine. The reaction mixture became reddish brown and warmed nearly to reflux. The mixture was stirred for 2 days at room temperature under argon. After evaporation of solvent, the residue was washed with 800 mL of hexane, and then with a total of 1 L of water. The remaining solid was dissolved in 300 mL CH$_2$Cl$_2$ and passed through a plug of Na$_2$SO$_4$/silica gel/Na$_2$SO$_4$. The thioester was obtained (11.55 g) as a yellow solid. $^1$H NMR (CDCl$_3$) δ7.20 (t, 2H), 7.60–7.68 (m, 4H), 7.80–7.88 (m, 2H), 8.129 (d, 2H), 8.278 (d, 2H).

b. 4'-Fluorophenyl 10-methylacridinium-9-thiocarboxylate trifluoromethanesulfonate. 4'-Fluorophenyl acridine-9-thiocarboxylate (11.36 g, 34 mmol) was dissolved in CH$_2$Cl$_2$ (100 mL) under argon and methyl triflate (20 mL) was added. The solution became brown and produced a yellow precipitate. After 2 days, the precipitate was filtered, washed with 50 mL of CH$_2$Cl$_2$ and 500 mL of hexane and dried to obtain the product as yellow solid (15.3 g). $^1$H NMR (DMSO-d$_6$) δ4.93 (s, 3H), 7.53 (t, 2H), 7.97–8.37 (m, 2H), 8.14 (t, 2H), 8.54 (t, 2H), 8.61 (d, 2H), 8.92 (d, 2H).

c. 4'-Fluorophenyl 10-methylacridan-9-thiocarboxylate. With room lighting off, 4'-fluorophenyl 10-methyl-acridinium-9-thiocarboxylate trifluoromethanesulfonate (15.05 g, 30 mmol) was suspended in 2-propanol (150 mL) and 2.1 mL of acetic acid. The solution was purged with argon for 30 min. and then 10.0 g of zinc powder added. Addition of zinc caused the yellow color of the solution to disappear within minutes. The mixture was stirred over night. The mixture was filtered and the solids washed with 2-propanol and then hexane. The remaining solid was washed with CH$_2$Cl$_2$. Since a TLC analysis showed that the product had dissolved in both solutions, the filtrates were concentrated and combined to obtain a brown solid which was redissolved in CH$_2$Cl$_2$ and passed through a plug of Na$_2$SO$_4$/silica gel/Na$_2$SO$_4$, eluting with CH$_2$Cl$_2$. A mixture of the expected acridan thioester and an acridan isopropyl ester resulting from transesterification was obtained. The two products were separated by column chromatography (50% CH$_2$Cl$_2$:hexane). One fraction of pure acridan thioester product (2.5 g) was obtained as a white solid. A second fraction was obtained as a mixture with the isopropyl ester. $^1$H NMR (CDCl$_3$) δ3.45 (s, 3H), 5.08 (s, 1H), 6.94–7.06 (m, 6H), 7.17–7.24 (m, 2H), 7.31–7.39 (m, 4H).

d. 9-(4-Fluorophenylthiophosphoryloxymethylidene)-10-methylacridan, bis(cyanoethyl) ester. With room lighting off, 4-fluorophenyl 10-methylacridan-9-thiocarboxylate (1.00 g, 2.87 mmol) in 10 mL of anhydrous THF was added dropwise to a solution of LDA in THF at –78 C. After stirring 60 min at –78 C., the yellow solution was treated with a solution of POCl$_3$ (0.79 g) and pyridine (3.0 mL) in 10 mL of THF over a 25 minute period. The dry ice bath was removed after an additional hour and stirring continued for 2 h. The solution was cooled in an ice bath and treated with 3-hydroxypropionitrile (0.71 mL) and the ice bath removed after the addition was complete. After stirring over night at room temperature, the precipitated pyridine-HCl was filtered off and washed with 50 mL of THF. The combined filtrates were evaporated in vacuo. The residue was separated by column chromatography using 50–100% ethyl acetate/hexanes from which the 0.658 g of the product was isolated; $^1$H NMR (CDCl$_3$) δ2.44–2.64 (m, 4H), 3.49 (s, 3H), 3.86–4.16 (m, 4H), 6.92–7.15 (m, 6H), 7.26–7.46 (m, 4H), 7.786 (d, 1H), 7.906 (d, 1H); $^{31}$P NMR (CDCl$_3$) δ−9.49 (p) (rel. to ext. H$_3$PO$_4$).

e. 9-(4-Fluorophenylthiophosphoryloxymethylidene)-10-methylacridan, disodium salt (7). With room lighting off, a solution of the bis(cyanoethyl) phosphate compound (0.658 g) in 20 mL of acetone under argon for 30 min. A solution of 116.5 mg of NaOH in 4.0 mL of water was added and the solution stirred under argon over night. The precipitate which had formed was suction filtered, washed with 100 mL of acetone and air-dried. A second crop of solid formed in the filtrate and was combined with the first crop. The yield was 0.545 g of 7 as a slightly yellow solid. $^1$H NMR (D$_2$O) δ3.16 (s, 3H), 6.80–6.98 (m, 4H), 7.06–7.14 (m, 4H), 7.21 (t, 1H), 7.32 (t, 1H), 7.78 (d, 1H), 8.19 (d, 1H); $^{31}$P NMR (D$_2$O) δ1.22 (s) (rel. to ext. H$_3$PO$_4$).

Example 8

Synthesis of Acridan Derivative 8

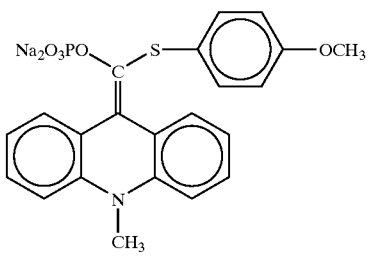

a. 4'-Methoxyphenyl acridine-9-thiocarboxylate. The Acridine-9-carbonyl chloride (2.0 g), made as described above was dissolved in 20 mL of CH$_2$Cl$_2$. 4-Methoxythiophenol (1.27 g) was added dropwise followed by 1.96 g of pyridine. The reaction mixture was stirred for 3.5 days at room temperature. The precipitate was collected, washed with water and dried to produce a first crop of product. The CH$_2$Cl$_2$ solution was washed with 3×50 mL of water, dried and evaporated to obtain a crude material which was chromatographed on silica gel (ethyl acetate) to yield a second crop of the pure product. $^1$H NMR (CDCl$_3$) δ3.86 (s, 3H), 7.01 (d, 1H), 7.56 (d, 2H), 7.62–8.28 (m, 8H).

b. 4'-Methoxyphenyl acridan-9-thiocarboxylate. 4'-Methoxyphenyl acridine-9-thiocarboxylate (2.0 g) was suspended in 2-propanol (150 mL). NH$_4$Cl (7.35 g) was added by portions to the solution followed by zinc (8.9 g). The solution was stirred at room temperature for 2 h and then warmed gently for 3 h. TLC of the reaction mixture showed complete consumption of the starting material. The solution was filtered and precipitate was washed with CH$_2$Cl$_2$. The filtrate and washings were concentrated to obtain a crude product which was redissolved in CH$_2$Cl$_2$ and washed with water (3×50 mL). The organic layer was dried and concentrated to yield the product which contained a small amount of the acridan isopropyl ester. $^1$H NMR (CDCl$_3$) δ3.74 (s, 3H), 5.19 (s, 1H), 6.29 (br s, 1H), 6.75–7.31 (m, 12H).

c. 4'-Methoxyphenyl 10-methylacridan-9-thiocarboxylate trifluoromethanesulfonate. 4'-Methoxyphenyl acridan-9-thiocarboxylate (1.8 g) was dissolved in CH$_2$Cl$_2$ under argon and methyl triflate (6.3 g) was added. The solution was stirred overnight at room temperature to effect complete methylation. The reaction mixture was concentrated and the residue separated by column chromatography (30% ethyl acetate/hexane) to obtain the 1.08 g of the product. $^1$H NMR (CDCl$_3$) δ3.45 (s, 3H), 3.76 (s, 3H), 5.07 (br s, 1H), 6.81–7.36 (m, 12H).

d. 9-(4-Methoxyphenylthiophosphoryloxymethylidene)-10-methylacridan, bis(cyanoethyl) ester. A solution of 4-methoxyphenyl 10-methylacridan-9-thiocarboxylate (700 mg) in 10 mL of dry THF was added dropwise to a solution of LDA (1.4 eq.) in 10 mL of dry THF maintained at −78 C. After stirring for 1 h at −78 C., a solution of POCl$_3$ (520 mg) and pyridine (1.64 g) in 4 mL of THF was added dropwise. Stirring continued for 30 min at −78° C., the dry ice bath was removed and stirring continued for another hour. The solution was again cooled in an ice bath and pyridine (1 mL) and 3-hydroxypropionitrile (0.86 mL) added dropwise. After stirring over night at room temperature, the precipitated pyridine-HCl was filtered away and the reaction solvent evaporated in vacuo. The residue was taken up in ethyl acetate and washed with water (3×25 mL). The organic solution was dried and concentrated, the crude product subjected to column chromatography (30–100% ethyl acetate/hexane) from which the product was isolated as a light yellow solid; $^1$H NMR (CDCl$_3$) δ2.44–2.62 (m, 4H), 3.51 (s, 3H), 3.82 (s, 3H), 3.88–4.11 (m, 4H), 6.53–7.41 (m, 10H), 7.84–7.91 (m, 2H); $^{31}$P NMR (CDCl$_3$) δ−9.63 (p) (rel. to ext. H$_3$PO$_4$ ).

e. 9-(4-Methoxyphenylthiophosphoryloxymethylidene)-10-methylacridan, disodium salt (8). A solution of the bis(cyanoethyl) phosphate compound (0.42 g) in 11 mL of acetone was purged with argon. A 614 μL portion of a 2.5 M NaOH solution in water was added dropwise and the solution stirred under argon over night. The precipitate which had formed was suction filtered and air-dried producing a quantitative yield of 8 as a slightly yellow solid. $^1$H NMR (D$_2$O) δ3.32 (s, 3H), 3.70 (s, 3H), 6.69–7.33 (m, 10H), 7.80 (d, 1H), 8.18 (d, 1H).

Example 9

Synthesis of Acridan Derivative 9

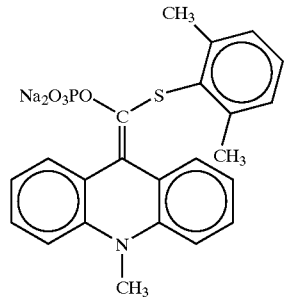

a. 2',6'-Dimethylphenyl acridine-9-thiocarboxylate. Acridine-9-carboxylic acid (2 g) was suspended in thionyl chloride (25 mL) and the reaction mixture was refluxed for 2.5 h. The solvent was removed under reduced pressure leaving a solid which was dissolved in 50 mL of CH$_2$Cl$_2$. This solution was cooled in an ice bath and 2,6-dimethylthiophenol (1.23 g) was added dropwise followed by 3.6 mL of pyridine. The reddish brown reaction mixture was stirred for 1.5 h at room temperature. The reaction mixture was diluted with CH$_2$Cl$_2$ and washed with 3×50 mL of water. The organic layer was dried and concentrated to obtain an orange product which was chromatographed on silica gel (ethyl acetate) to yield 2.5 g of the pure product as an off-white solid. $^1$H NMR (CDCl$_3$) δ2.68 (s, 6H), 7.30–7.41 (m, 3H), 7.63–8.31 (m, 8H).

b. 2',6'-Dimethylphenyl acridan-9-thiocarboxylate. 2',6'-Dimethylphenyl acridine-9-thiocarboxylate (2.46 g) was suspended in 2-propanol (200 mL). Ammonium chloride (9.5 g) was added by portions to the solution followed by zinc (11.65 g).The solution was gently warmed for 2 h. TLC of the reaction mixture showed complete consumption of starting material. The solution was filtered and precipitate was washed with $CH_2Cl_2$. The filtrate was concentrated to obtain a white solid which was redissolved in $CH_2Cl_2$ and washed with water (3×50 mL). The organic layer was dried over $Na_2SO_4$ and concentrated to yield 2.46 g of the product as a white solid. $^1$H NMR ($CDCl_3$) δ2.08 (s, 6H), 5.24 (s, 1H), 6.27 (br s, 1H), 6.78–7.31 (m, 11H).

c. 2',6'-Dimethylphenyl 10-methylacridanthiocarboxylate. 2',6'-Dimethylphenyl 10-methylacridan-9-thiocarboxylate (2.0 g) dissolved in 30 mL of $CH_2Cl_2$ under argon and methyl triflate (6.6 mL) was added. The solution was stirred for 3 days at room temperature. The mixture was evaporated to dryness and the crude product purified by column chromatography ($CH_2Cl_2$) to obtain 1.85 g of the product as a white solid. $^1$H NMR ($CDCl_3$) δ2.09 (s, 6H), 3.46 (s, 3H), 5.09 (s, 1H), 6.97–7.36 (m, 11H).

d. 9-(2,6-Dimethylphenylthiophosphoryloxymethylidene)-10-methylacridan, bis(cyanoethyl) ester. 2,6-Dimethylphenyl 10-methylacridan-9-thiocarboxylate (700 mg) in 12 mL of dry THF was added to a solution of LDA (1.4 eq.) in 10 mL of dry THF at −78° C. The orange solution was stirred for 60 min at −78 C. A solution of $POCl_3$ (280 μL) and pyridine (1.57 mL) in 4 mL of THF was added dropwise. The reaction mixture was stirred for 15 min before the dry ice bath was removed. Stirring continued for 60 min. TLC (30% ethyl acetate/hexane) showed that most of the starting material was reacted.

The solution was cooled in an ice bath and treated with pyridine (1.0 mL) and 3-hydroxypropionitrile (666 μL). After stirring over night at room temperature, the precipitated pyridine-HCl was filtered and washed with THF. The combined organic solutions were evaporated in vacuo. The organic layer was dried and concentrated to obtain an orange product which was chromatographed on silica gel (ethyl acetate) to yield 80 mg of the pure product as a yellow oil. $^1$H NMR ($CDCl_3$) δ2.34–2.43 (m, 4H), 2.47 (s, 6H), 3.47 (s, 3H), 3.42–3.71 (m, 4H), 7.01–8.07 (m, 11H); $^{31}$P NMR ($CDCl_3$) δ−10.207 (p) (rel. to ext. $H_3PO_4$).

e. 9-(2,6-Dimethylphenylthiophosphoryloxymethylidene)-10-methylacridan. disodium salt (9). A solution of the bis(cyanoethyl) phosphate compound (0.80 g) in 6 mL of acetone was purged with argon. A solution of 1M NaOH in water (293 μL) was added dropwise followed by an additional 300 μL of water and the solution stirred under argon over night. The precipitate which had formed was suction filtered, washed with acetone and air-dried. The yield was 0.60 g of 9 as a white solid. $^1$H NMR ($D_2O$) δ2.13 (s, 6H), 3.19 (s, 3H), 6.60–8.19 (m, 11H); $^{31}$P NMR ($D_2O$) δ1.653 (s) (rel. to ext. $H_3PO_4$).

Example 10

Synthesis of Acridan Derivative 10

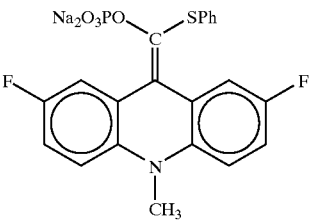

a. 4-Fluoroacetanilide. 4-Fluoroaniline (20 g) was dissolved in 25 mL of acetic acid and cooled in an ice bath. Acetic anhydride (25 mL) was added in 5 mL portions to the stirred solution. The resulting solution was poured into 200 mL of cold water and the precipitated product filtered off. The solid was washed with water and vacuum-dried. $^1$H NMR ($CDCl_3$) δ2.175 (s, 3H), 7.014 (t, 2H), 7.15 (br s, 1H), 7.43–7.48 (m, 2H).

b. 4,4'-Difluorodiphenylamine. 4-Fluoroacetanilide (12.0 g) was condensed with 1-bromo-4-fluorobenzene (21 mL) in the presence of 11.08 g of $K_2CO_3$ and 1.61 g of CuI at 190° C. for 90 h. After cooling, the mixture was filtered and the solid washed with $CH_2Cl_2$. The combined organic solutions were evaporated under vacuum producing ca. 20 g of a dark brown liquid. This was dissolved in 100 mL of ethanol and refluxed with 9 g of KOH for 24 h. The ethanol was evaporated and the dark residue taken up in ether and washed with water (3×100 mL). The ether solution was dried and concentrated and the crude product purified by column chromatography on silica using 15% ethyl acetate/hexane: $^1$H NMR ($CDCl_3$) δ5.46 (br s, 1H), 6.947 (s, 4H), 6.97 (s, 4H); $^{13}$C NMR ($CDCl_3$) δ115.86, 116.16, 119.38, 119.47.

c. 2,7-Difluoroacridine-9-carboxylic acid. 4,4'-Difluorodiphenylamine (5.4 g) dissolved in 50 mL of $CH_2Cl_2$ was added to a solution of 2.52 mL (0.11 mol) of oxalyl chloride in 30 mL of $CH_2Cl_2$ under an argon atmosphere at a rate to maintain reflux. The mixture was refluxed an additional 35 min. The resulting solution was evaporated to remove excess oxalyl chloride. The solid was redissolved in 75 mL of $CH_2Cl_2$ and cooled in an ice bath. The flask was purged with argon and $AlCl_3$ (14.28 g) was added in portions while the mixture was stirred. The mixture became thick during the addition and began to reflux. Reflux was maintained for an additional hour after all of the $AlCl_3$ had been added. The cooled mixture was evaporated in vacuo and quenched with 300 mL of 3:1 ice/5 M HCl. The mixture was stirred for 1 h, the orange solid (isatin) filtered off with suction and washed with water. $^1$H NMR (acetone-$d_6$) δ6.92–6.97 (m, 1H), 7.35–7.61 (m, 6H).

The isatin product was refluxed in 110 mL of 10% KOH solution in water over night. The dark green mixture was cooled and acidified with 400 mL of 1:1 ice/5 M HCl. The solid was washed with water and air-dried yielding the acridine acid. $^1$H NMR (DMSO-$d_6$) δ7.81–7.94 (m, 4H), 8.31–8.36 (m, 2H).

d. Phenyl 2,7-difluoroacridine-9-thiocarboxylate. 2,7-Difluoroacridine-9-carboxylic acid (1.0 g) was suspended in $SOCl_2$ (5 mL) and the reaction mixture was refluxed for 3 h. The solvent was removed under reduced pressure leaving a brown solid which was dissolved in 20 mL of $CH_2Cl_2$ under argon. Thiophenol (468 mg) was added followed by pyridine (2 mL). The reaction mixture was stirred overnight at room temperature. The reaction mixture was diluted with CH$_2$C$_2$ and washed with water (3×50 mL). The organic layer was dried over MgSO$_4$ and concentrated to obtain a crude material which was chromatographed on silica gel (40% ethyl acetate/hexane) to yield 1.2 g of the pure product. $^1$H NMR (CDCl$_3$) δ7.52–7.75 (m, 9H), 8.26–8.30 (m, 2H).

e. Phenyl 2,7-difluoroacridan-9-thiocarboxylate. Phenyl 2,7-difluoroacridine-9-thiocarboxylate (1.2 g) was suspended in 2-propanol (125 mL) along with NH$_4$Cl (4.57 g). Zinc (5.5 g) was added and the reaction mixture was warmed for 2.5 h followed by a 1.5 h period at room temperature. TLC of the reaction mixture showed complete conversion to a new material. The solution was filtered and the precipitate was washed with CH$_2$Cl$_2$. The filtrate was concentrated and the light orange residue was redissolved in CH$_2$Cl$_2$ and washed with water (2×100 mL). The organic layer was dried over Na$_2$SO$_4$ and concentrated to yield the crude product which was used without further purification. $^1$H NMR (CDCl$_3$) δ5.12 (s, 1H), 6.19 (br s, 1H), 6.72–7.35 (m, 11H).

f. Phenyl 2,7-difluoro-10-methylacridan-9-thiocarboxylate. Phenyl 2,7-difluoroacridan-9-thiocarboxylate (1.4 g) was dissolved in CH$_2$Cl$_2$ (50 mL) under argon and methyl trifluoromethanesulfonate (5.29 g) was added. The solution was stirred overnight at room temperature. TLC showed the conversion to be ca. 50% complete so another 2 mL of methyl triflate was added and stirring continued for another 40 h. This reaction mixture was concentrated and the residue separated chromatographically using 20–50% CH$_2$Cl$_2$/hexane to obtain the product along with a minor amount of the isopropyl ester of the acridancarboxylate as a by-product. 1H NMR (acetone-d$_6$) δ3.41 (s, 3H), 4.98 (s, 1H), 6.89–7.34 (m, 11H).

g. 9-(Phenylthiophosphoryloxymethylidene)-2,7-difluoro-10-methylacridan, bis(cyanoethyl) ester. Phenyl 2,7-difluoro-10-methylacridan-9-thiocarboxylate (500 mg, 1.3 mmol) was added to a solution of LDA (1.4 mmol) in THF –78° C. After stirring 1 h, a solution of POCl$_3$ (313 mg) and pyridine (1.07 g) in 4 mL of THF was added and the reaction mixture maintained at –78° C. for 1 h. The dry ice bath was removed and stirring continued for 1 h.

The solution was cooled in an ice bath and treated dropwise with pyridine and 3-hydroxypropionitrile (484 mg) in 4 mL of THF. After stirring over night at room temperature, the precipitated pyridine-HCl was filtered away and the reaction solvent evaporated in vacuo. The residue was taken up in ethyl acetate and washed with 4×25 mL of water. After drying and evaporating the ethyl acetate, the residue was separated chromatographically (75–80% ethyl acetate/hexane) to yield the product was isolated; $^1$H NMR (CDCl$_3$) δ2.48–2.65 (m, 4H), 3.48 (s, 3H), 4.02–4.16 (m, 4H), 6.91–7.66 (m, 11H); $^{31}$P NMR (CDCl$_3$) δ–9.874 (p) (rel. to ext. H$_3$PO$_4$).

h. 9-(Phenylthiophosphoryloxymethylidene)-2,7-difluoro-10-methylacridan, disodium salt (10). A solution of the bis(cyanoethyl) phosphate compound (0.28 g) in 17 mL of acetone was cooled in an ice bath and purged with argon. A solution of 1N NaOH in 1.02 mL of water was added dropwise and the solution stirred under argon for 16 h. The precipitate which had formed was suction filtered, washed with acetone and vacuum-dried. The yield was 0.236 g of 10 as an off-white solid. $^1$H NMR (D$_2$O) δ3.28 (s, 3H), 6.78–8.21 (m, 11H); $^{31}$P NMR (D$_2$O) δ1.006 (s) (rel. to ext. H$_3$PO$_4$).

Example 11

Synthesis of Acridan Derivative 11

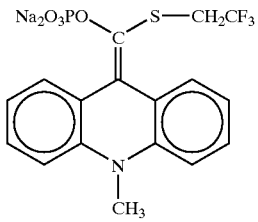

a. 2',2',2'-Trifluoroethyl acridine-9-thiocarboxylate. Acridine-9-carbonyl chloride (1.89 g), made as described above was dissolved in 30 mL of CH$_2$Cl$_2$ under argon. This solution was cooled in an ice bath and 2,2,2-trifluoroethanethiol (1.0) was added dropwise followed by 3.23 g of pyridine. The reaction mixture was stirred at room temperature for 3 days. Water (20 mL) was added and the remaining precipitate filtered and discarded. The CH$_2$Cl$_2$ solution was washed with 3×25 mL of water, dried and evaporated to obtain the product as an off-white solid sufficiently pure to take on to the next reaction. $^1$H NMR (CDCl$_3$) δ4.02–4.10 (q, 2H), 7.61–8.31 (m, 8H).

b. 2',2',2'-Trifluoroethyl acridan-9-thiocarboxylate. 2',2',2'-Trifluoroethyl acridine-9-thiocarboxylate (1.7 g) was suspended in 2-propanol (150 mL) along with NH$_4$Cl (7.08 g). Zinc (8.61 g) was added and the reaction mixture was stirred for 1.5 h at room temperature. TLC of the reaction mixture showed complete conversion to a new material. The solution was filtered and the precipitate was washed with CH$_2$Cl$_2$. The filtrate was concentrated and the light orange residue was redissolved in CH$_2$Cl$_2$ and washed with water (3×50 mL). The organic layer was dried and concentrated to yield the crude product as an off-white solid sufficiently pure to take on to the next reaction. $^1$H NMR (CDCl$_3$) δ3.37–3.47 (q, 2H), 5.206 (s, 1H), 6.27 (br s, 1H), 6.78–7.27 (m, 8H).

c. 2',2',2'-Trifluoroethyl 10-methylacridan-9-thiocarboxylate. 2',2',2'-Trifluoroethyl acridan-9-thiocarboxylate (1.66 g) was dissolved in CH$_2$Cl$_2$ (20 mL) under argon and methyl triflate (4.06 mL) was added. The brown solution was stirred for 1.5 days at room temperature. After concentrating the CH$_2$Cl$_2$, the crude product was purified by column chromatography using 50% CH$_2$Cl$_2$/hexane. $^1$H NMR (CDCl$_3$) δ3.39–3.43 (q, 2H), 3.43 (s, 3H), 5.04 (s, 1H), 6.98–7.38 (m, 8H).

d. 9-(2',2',2'-Trifluoroethylthiophosphoryloxymethylidene)-10-methylacridan, bis(cyanoethyl) ester. 2',2',2'-Trifluoroethyl 10-methylacridan-9-thiocarboxylate (300 mg) in 10 mL of THF was added to a solution of LDA (1.4 eq.) in 10 mL of THF dropwise at –78° C. After stirring 60 min at –78 C., a solution of POCl$_3$ (239 mg) and pyridine (703 mg) in 4 mL of THF was added slowly. After 30 min, the dry ice bath was removed and stirring continued for 60 min. The solution was cooled in an ice bath and treated with pyridine (500 μL) and 3-hydroxypropionitrile (395 μL). A brownish-yellow precipitate formed. After stirring over night at room temperature, the precipitate was filtered away and the reaction solvent evaporated in vacuo. The residue was taken up in ethyl acetate, washed with 5×25 mL of water, dried and concentrated. The crude product was separated chromatographically using CH$_2$Cl$_2$ to elute the column and then switching solvents to a 60–100% ethyl acetate/hexane gradient. Two fractions were isolated, each as mixture of two closely eluting products, the slower eluting being the minor component. Each fraction was further purified separately by prep. TLC using 25% ethyl acetate/hexane. The slower eluting product proved to be the expected bis(cyanoethyl) phosphate ester. $^1$H NMR (CDCl$_3$) δ2.69 (t, 4H), 3.41–3.54 (q, 2H), 3.49 (s, 3H), 4.04–4.24 (m, 4H), 7.04–7.95 (m, 8H); $^{31}$P NMR-8.66 (p).

The other product was determined by $^1$H NMR, $^{13}$C NMR, $^{19}$F NMR and $^{31}$P NMR as well as homonuclear and heteronuclear decoupling experiments to be 9-(2',2'-difluoroethenylthio-phosphoryloxymethylidene)-10-methylacridan, bis(cyanoethyl) ester, derived from elimination of HF from the SCH$_2$CF$_3$ group and phosphorylation of the enolate. $^1$H NMR (CDCl$_3$) δ2.60–2.76 (m, 4H), 3.49 (s, 3H), 4.02–4.26 (m, 4H), 5.17 (d, 1H), 7.03–7.88 (m, 8H); $^{19}$F NMR (CDCl$_3$) δ–76.76 (d, J=Hz), –78.88 (t, J=Hz); $^{31}$P NMR (CDCl$_3$) δ–8.83 (p). Irradiation of the doublet at δ5.17 did not affect any other signal in the $^1$H NMR spectrum. Irradiation of the multiplet at δ4.02–4.26 collapsed the multiplet at δ2.60–2.76 to a singlet and collapsed the phosphorus signal to a singlet. Irradiation of the doublet at δ5.17 in the $^1$H spectrum collapsed the triplet in the $^{19}$F spectrum to a doublet.

e. 9-(2',2',2'-Trifluoroethylthiophosphoryloxymethylidene)-10-methylacridan, disodium salt (11). A solution of the bis(cyanoethyl) phosphate compound (15 mg) in 4 mL of acetone was purged with argon. A solution of 1M NaOH in water (58 μL) was added dropwise followed by an additional 100 μL of water and the solution stirred under argon over night. TLC showed complete deprotection. The mixture was concentrated to dryness, producing an off-white solid which was washed with 20% CH$_2$Cl$_2$/acetone and air-dried. $^1$H NMR (D$_2$O) δ3.399 (s, 3H), 3.45–3.61 (m, 2H), 7.04–8.18 (m, 8H); $^{31}$P NMR (D$_2$O) δ1.465 (s) (rel. to ext. H$_3$PO$_4$).

Example 12

Synthesis of Acridan Derivative 12

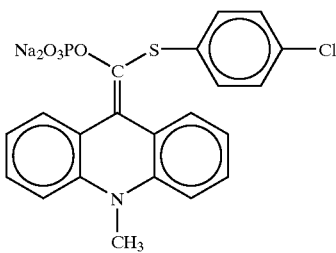

12 a. 4'-Chlorophenyl acridine-9-thiocarboxylate. 4-Chlorothiophenol (4.75 g) and 7.22 g of acridine-9-carbonyl chloride were dissolved in 100 mL of CH$_2$Cl$_2$ followed by 12.1 mL of pyridine. The reaction mixture became orange-brown. The mixture was stirred overnight at room temperature under argon. After evaporation of is 15 solvent, the solids were washed with 100 mL of hexanes, filtered, washed with another 100 mL of hexanes, filtered, and then with a 500 mL of water, filtered and air-dried. The thioester was obtained (8.71 g) as a slightly brownish yellow solid. $^1$H NMR (CDCl$_3$) δ7.47–7.50 (m, 2H), 7.58–7.67 (m, 4H), 7.81–7.86 (m, 2H), 8.12 (d, 2H), 8.29 (d, 2H).

b. 4'-Chlorophenyl acridan-9-thiocarboxylate. 4'-Chlorophenyl acridine-9-thiocarboxylate (2.0 g) was dissolved in CH$_2$Cl$_2$ (25 mL). The solution was purged with argon and then 3.72 g of zinc powder added followed by 0.45 mL of acetic acid. TLC showed the starting material was consumed in 20 min. The mixture was filtered and the solids washed with CH$_2$Cl$_2$. The combined CH$_2$Cl$_2$ solutions were washed with water (3×50 mL) and dried. A small amount of the product was purified by prep. TLC for analytical characterization. the remainder of the product was used without further purification. $^1$H NMR (CDCl$_3$) δ5.22 (s, 1H), 6.28 (s, 1H), 6.79–7.31 (m, 12H).

c. 4'-Chlorophenyl 10-methylacridan-9-thiocarboxylate. 4'-Chlorophenyl acridan-9-thiocarboxylate (2.0 g) was dissolved in CH$_2$Cl$_2$ (30 mL) under argon and methyl triflate (6.5 g) was added. The brown solution was evaporated and the crude product purified by column chromatography using 30% ethyl acetate/hexanes. The pure product (1.8 g) was thereby obtained. $^1$H NMR (CDCl$_3$) δ3.47 (s, 3H), 5.09 (s, 1H), 7.02–7.39 (m, 12H).

d. 9-(4-Chlorophenylthiophosphoryloxymethylidene)-10-methylacridan, bis(cyanoethyl) ester. 4-Chlorophenyl 10-methylacridan-9-thiocarboxylate (0.70 g) in 10 mL of anhydrous THF was added dropwise to a solution of LDA (1.4 eq.) in THF at –78 C. After stirring 60 min at –78 C., the yellow solution was treated with a solution of POCl$_3$ (0.517 g) and pyridine (1.52 mL) in 4 mL of THF slowly. The dry ice bath was removed after 30 min and stirring continued for 1 h. The solution became yellow and formed a precipitate.

The mixture was cooled in an ice bath and treated with 3-hydroxypropionitrile (0.89 g) and 1.0 mL of pyridine. The ice bath removed after the addition was complete. After stirring over night at room temperature, the precipitated pyridine-HCl was filtered off and washed with THF. The combined filtrates were evaporated in vacuo and the brown material obtained was dissolved in ethyl acetate and washed with 4×25 mL of water. The ethyl acetate solution was dried and concentrated. The residue was separated by column chromatography using 80–100% ethyl acetate/hexanes from which the 0.325 g of the product was isolated; $^1$H NMR (CDCl$_3$) δ2.48–2.64 (m, 4H), 3.53 (s, 3H), 3.86–4.16 (m, 4H), 6.94–7.94 (m, 12H); $^{31}$P NMR (D$_2$O) δ–9.48 (p) (rel. to ext. H$_3$PO$_4$).

e. 9-(4-Chlorophenylthiophosphoryloxymethylidene)-10-methylacridan, disodium salt (12). A solution of the bis(cyanoethyl) phosphate compound (0.325 g) in 10 mL of acetone was purged with argon. A solution of 2.5 M NaOH (473 μL) was added followed by an additional 500 μL of water. The solution was stirred under argon over night. The precipitate which had formed was suction filtered and air-dried. The mother liquor was found to contain the mono (cyanoethyl)-protected compound (140 mg). A second crop of the disodium salt was obtained by repeating the NaOH deprotection. $^1$H NMR (D$_2$O) δ3.35 (s, 3H), 6.92–7.36 (m, 10H), 7.78 (d, 1H), 8.20 (d, 1H); $^{31}$P NMR (D$_2$O) δ1.22 (s) (rel. to ext. H$_3$ PO$_4$).

Example 13

Synthesis of Acridan Derivative 13

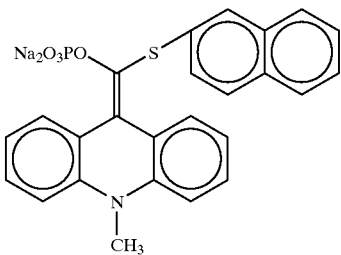

a. Naphthyl acridine-9-thiocarboxylate. 2-Naphthalenethiol (48.81 g) and the acridine-9-carbonyl chloride prepared from 65.17 g of acridine-9-carboxylic acid were dissolved in 100 mL of $CH_2Cl_2$ followed by the addition of 120 mL of pyridine. The mixture was stirred overnight at room temperature under argon. After evaporation of solvent, the solids were washed with 500 mL of hexanes, filtered, washed with another 500 mL of hexanes, filtered, and then washed with 600 mL of water, filtered and air-dried overnight. The thioester was dissolved in 1500 ml of $CH_2Cl_2$, dried over sodium sulfate, filtered, and dried in vacuo. The thioester was obtained (94.67 g) as a brown solid. $^1$H NMR (CDCl$_3$) δ7.54–8.00 (m, 11H), 8.17–8.31 (m, 4H).

b. Naphthyl 10-methylacridinium-9-thiocarboxylate triflate. Naphthyl acridine-9-thiocarboxylate (26.38 g) was suspended in $CH_2Cl_2$ (200 mL). Methyl trifluoromethanesulfonate (24.5 ml) was added and the mixture left to stir overnight. The mixture was filtered and the solids washed with $CH_2Cl_2$ (300 ml) and hexanes (500 ml). After air drying, the product (28.83 g) was obtained as a yellow solid. $^1$H NMR (acetone-d$_6$) δ5.20 (S, 3H), 7.66–7.75 (m, 2H), 7.88–7.92 (m, 1H), 8.03–8.09 (m, 2H), 8.15 (d, 1H), 8.26 (t, 2H), 8.48 (S, 1H), 8.61–8.68 (m, 2H), 8.80 (d, 2H), 9.03 (d, 2H).

c. Naphthyl 10-methylacridan-9-thiocarboxylate. Naphthyl 10-methylacridinium-9-thiocarboxylate triflate (65.50 g) was suspended in $CH_2Cl_2$ (1000 mL) under argon and glacial acetic acid (21.2 ml) and zinc (40.43 g) were added. After stirring overnight, TLC showed the dissappearance of the starting material and the formation of a new product. The reaction mixture was filtered through a bed of silica gel and the $CH_2Cl_2$ removed in vacuo. The slightly yellow solid obtained was stirred in isopropanol (500 ml), filtered, washed with 500 ml more isopropanol, and allowed to air dry. The pure product (46.36 g) was thereby obtained. $^1$H NMR (CDCl$_3$) δ3.47 (s, 3H), 5.13 (s, 1H), 7.00–7.06 (m, 4H), 7.25–7.49 (m, 7H), 7.70–7.79 (m, 4H).

d. 9-(Naphthylthiophosphoryloxymethylidene)-10-methyl-acridan, bis(cyanoethyl) ester. Naphthyl 10-methylacridan-9-thiocarboxylate (17.32 g) in 600 mL of anhydrous THF was added dropwise to a solution of LDA (1.25 eq.) in THF at –78 C. After stirring 90 min at –78 C., the orangish brown solution was treated with a solution of $POCl_3$ (20.80 g) and pyridine (50 mL) in 150 mL of THF slowly. The dry ice bath was removed after 60 min and stirring continued for 1 h. The solution became brown and formed a precipitate.

The mixture was treated with 3-hydroxypropionitrile (27.8 ml). After stirring over night at room temperature, the precipitated pyridine-HCl was filtered off and washed with THF. The combined filtrates were evaporated in vacuo and the brown oil obtained was separated by column chromatography using 50–100% ethyl acetate/hexanes from which the product was isolated. The yellow oil was dissolved in $CH_2Cl_2$ (300 ml), washed with water (450 ml), dried over sodium sulfate, filtered, and dried in vacuo. This yielded the product (17.76 g) as a yellow solid. $^1$H NMR (CDCl$_3$) δ2.33–2.53 (m, 4H), 3.53 (s, 3H), 3.82–4.06 (m, 4H), 6.93 (t, 1H), 7.03 (d, 1H), 7.10–7.18 (m, 2H), 7.25–7.55 (m, 5H), 7.79–7.92 (m, 5H), 8.02 (d, 1H); $^{31}$P NNR (CDCl$_3$) δ–9.69 (p) (rel. to ext. $H_3PO_4$).

e. 9-(Naphthylthiophosphoryloxymethylidene)-10-methylacridan, disodium salt (13). A solution of the bis (cyanoethyl) phosphate compound (17.28 g) in 200 mL of acetone was purged with argon. A solution of NaOH (2.76 g) in 50 ml of water was added and the solution was stirred under argon over night. The precipitate which had formed was suction filtered washed with 20% water in acetone (300 ml) and dried under vacuum. The product (15.07 g) was obtained as a light yellow solid. $^1$H NMR (D$_2$O) δ3.22 (s, 3H), 6.67 (d, 1H), 6.87 (t, 1H), 7.01 (t, 1H), 7.08–7.15 (m, 2H), 7.23 (d, 1H), 7.31–44 (m, 3H), 7.51 (s, 1H), 7.59 (d, 2H), 7.73 (d, 1H), 7.86 (d, 1H), 8.25 (d, 1H); $^{31}$P NM (D$_2$O) δ1.30 (s) (rel. to ext. $H_3PO_4$).

Example 14

Chemiluminescent Detection of Alkaline Phosphatase with Compound 1

An effective reagent composition for chemiluminescent detection of alkaline phosphatase comprised 0.1 M tris buffer, pH 8.5, 0.88 mm magnesium salt, 0.33 mM acridan phosphate 1 (from a 1:100 dilution of a 0.033 M methanol solution) and 0.01 mg/mL of the Enhancer A (polyvinylbenzyltributylphosphonium chloride co-polyvinylbenzyltrioctylphosphonium chloride, containing a 3:1 ratio of tributyl:trioctyl groups). Reaction of 100 µL of this composition with $10^{-13}$ mol of AP at 25° C. in a test tube housed in a Turner TD-20e luminometer produced easily measurable blue chemiluminescence which reached maximum intensity in 2 min.

Example 15

Chemiluminescent Detection with Compounds 2–13

In the manner of Example 14, compositions containing each of compounds 2–13 were reacted with AP at 25° C. Each produced easily measurable chemiluminescence discernable above the background measured in the absence of AP.

It will be obvious to one skilled in the art that other compounds of formula I in addition to those specifically illustrated herein will function in like manner in the present methods.

Example 16

Chemiluminescent Detection of Alkaline Phosphatase with Compound 5

An effective reagent composition for chemiluminescent detection of alkaline phosphatase comprised 0.2 M 2-methyl-2-amino-1-propanol buffer, pH 9.6, 0.88 mm $Mg^{2+}$, 0.66 mM acridan phosphate 5 (from a 1:100 dilution of a 0.033 M methanol solution) and 0.5 mg/mL of the Enhancer A. Reaction of 100 µL of this composition with $10^{-13}$ mol of AP at 25° C. in a test tube housed in a Turner TD-20e luminometer produced easily measurable blue chemiluminescence which reached maximum intensity in 2 min. Light intensity measured between 1 and 10 min correlated with amount of enzyme in the range $8\times10^{-14}$ mol to $8\times10^{-18}$ mol.

Example 17

Kinetic Profile of Chemiluminescence Intensity

The rapid detection speed afforded by compositions containing the acridan phosphate 1 is shown by the plot in FIG. 1. Reaction of 100 μL of the reagent composition of Example 14 with $8\times10^{-16}$ mol of AP at 25° C. caused a burst of light emission which achieved maximum intensity in ca. 2 min. The figure also shows for comparison the chemiluminescence profile of the ester phenyl 10-methylacridan-9-carboxylate in a reagent composition similar to that described in Example 14 but containing the ester in place of 1. Addition of AP to the latter solution of the ester produced no effect. The much lower light intensity and slower rise time from spontaneous autoxidation of the ester is incompatible with a scheme in which emission from reaction of 1 is simply due to generation of the ester (via removal of the phosphate protecting group from the enol phosphate) by AP followed by autoxidation of the ester.

Example 18

Spectroscopic Study of Reaction of 1 with AP

Figure 2:
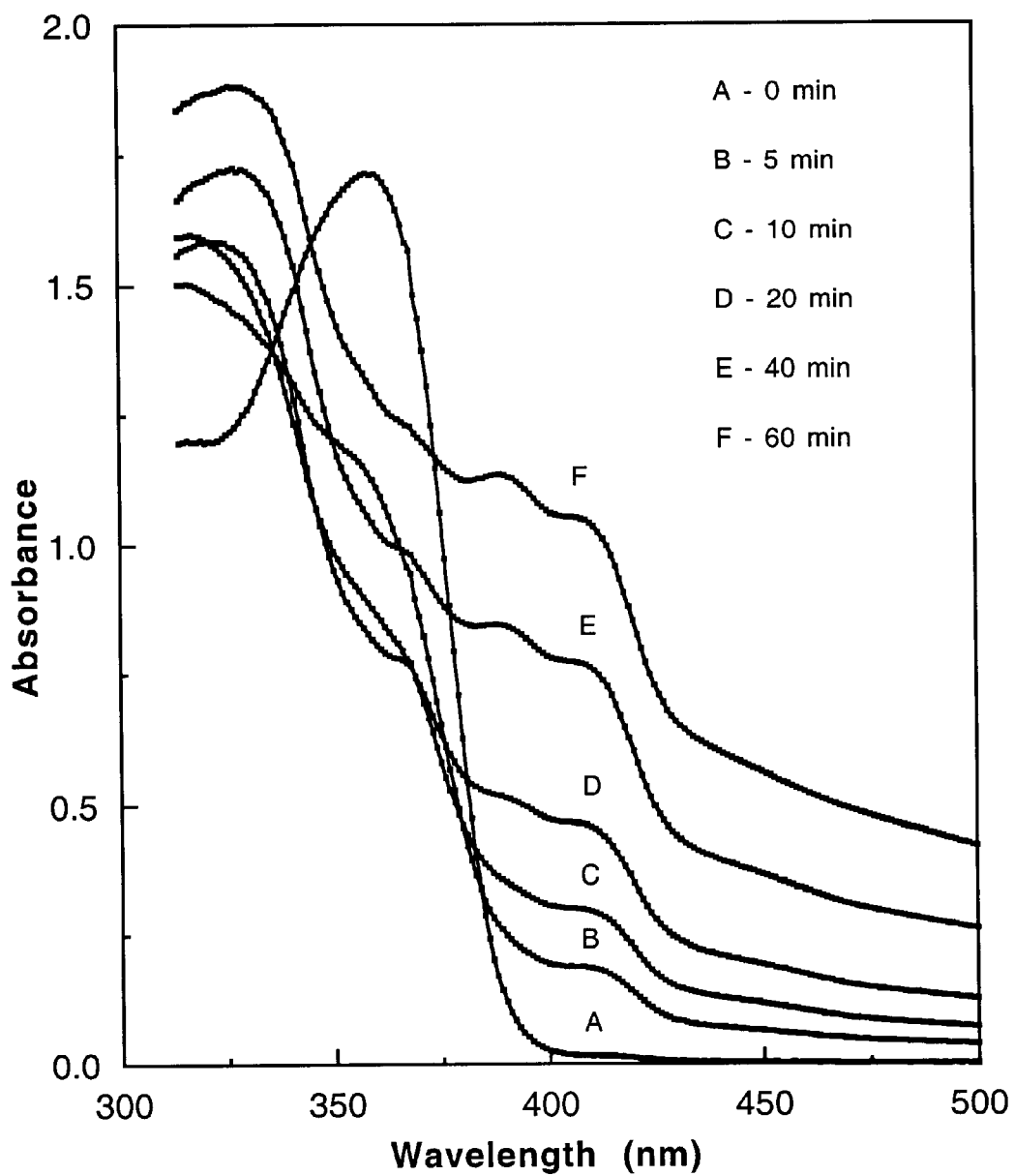
FIG. 2 is a plot of the ultraviolet-visible absorption spectrum of a reaction mixture containing 3 mL of a reagent composition containing 1 with $2.4\times10^{12}$ mol of AP at room temperature. Curves labeled A-F represent scans taken 0, 5, 10, 20, 40 and 60 min after addition of enzyme.

The progress of the reaction between 3 mL of the reagent composition of Example 14 and $2.4\times10^{-12}$ mol of AP at ambient temperature was monitored by UV-visible spectroscopy with a diode array detector. The spectrum was acquired at 5 min intervals. The evolution of the spectrum revealed in FIG. 2 showed a complex pattern consisting of multiple intermediates and products. Curves labeled A-F represent scans taken 0, 5, 10, 20, 40 and 60 min after addition of enzyme.

Example 19

Chemiluminescence Spectrum

Figure 3:
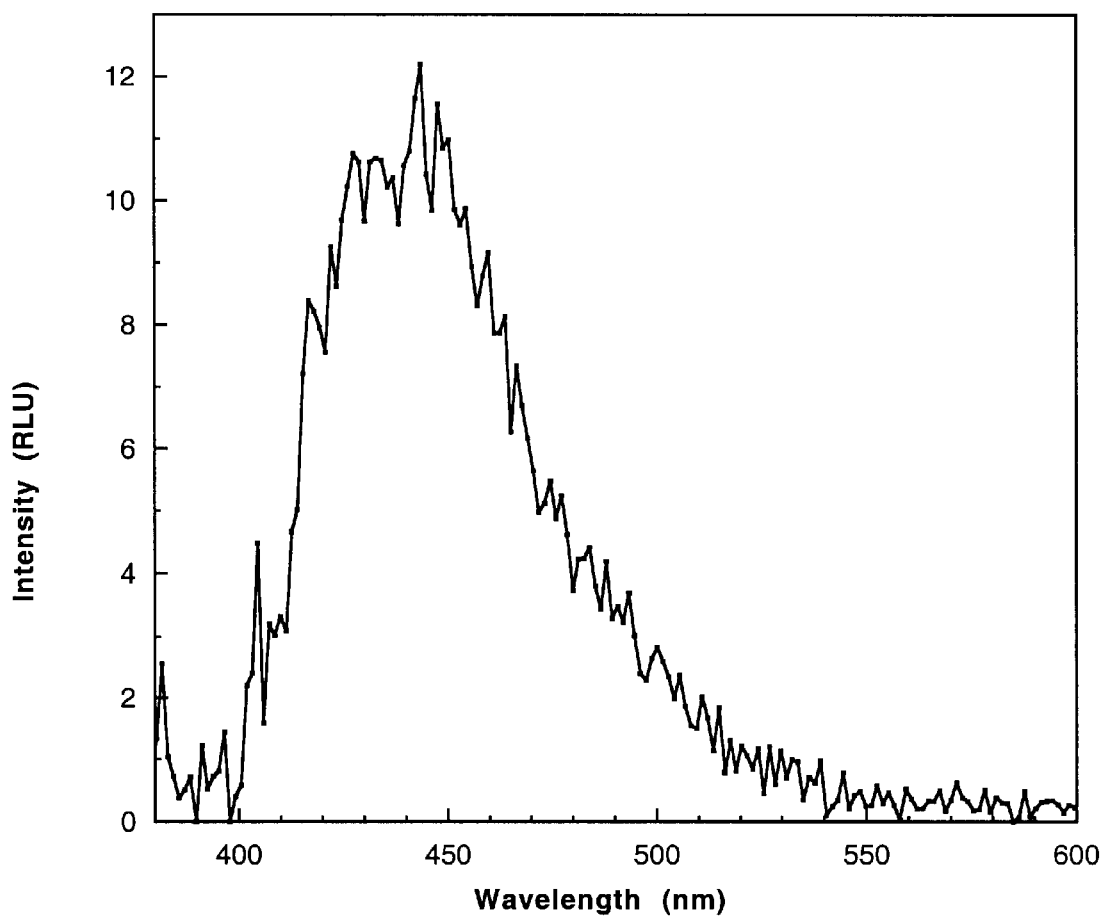
FIG. 3 is a plot of the chemiluminescence spectrum produced by reaction of 200 $\mu$L of a reagent composition containing 1 with $8\times10^{-13}$ mol of AP at room temperature.

A chemiluminescence spectrum was obtained using a device constructed by Dr. Barry Schoenfelner of Lumigen. The reagent composition of Example 14 (200 μL) was reacted with AP ($8\times10^{-13}$ mol) in a sample holder consisting of a test tube inside a light tight box. The emitted light was collected by a lens, and dispersed by a grating monochromator onto a CCD camera element. No correction for the change in intensity with time is required since this system images all wavelengths of visible light simultaneously. The spectrum of light emitted, shown in FIG. 3, reveals a broad emission with a maximum intensity at about 430 nm. This spectrum matches the fluorescence of N-methylacridone. The apparent fine structure in the spectrum is the result of instrument noise.

Example 20

Effect of pH on Chemiluminescent Reaction of 1 with Alkaline Phosphatase

Chemiluminescent detection of alkaline phosphatase with acridans of the present invention can be performed over a broad range of pH. Solutions comprising a 0.1 M buffer (either tris or 2-methyl-2-amino-1-propanol, 221), pH 7–10.5, 0.88 mM $Mg^{2+}$, 0.33 mM acridan phosphate 1 (from a 1:100 dilution of a 0.033 M methanol solution) and 0.01 mg/mL of Enhancer A were prepared and the background light emission measured after 10 min at 25° C. An aliquot of an AP solution containing $8\times10^{-16}$ mol of enzyme was injected and light intensity monitored until maximum intensity was reached. S/B represents the ratio of maximum light intensity to the light intensity in the absence of enzyme.

TABLE 2

| Entry | pH | Buffer | S/B |
|---|---|---|---|
| 1 | 7.0 | tris | 37 |
| 2 | 7.5 | tris | 144 |
| 3 | 8.0 | tris | 273 |
| 4 | 8.5 | tris | 280 |
| 5 | 9.0 | tris | 195 |
| 6 | 9.0 | 221 | 200 |
| 7 | 9.5 | 221 | 87 |
| 8 | 10.0 | 221 | 13 |
| 9 | 10.5 | 221 | 1.3 |

Example 21

Enhancement of Chemiluminescence by Surfactants

The enhancement of chemiluminescence, defined as the increase in light intensity over the level in the absence of the test substance, was assessed under a standard set of test conditions in the reaction of acridan 1 with AP in the presence of various surfactant compounds. The concentration of each surfactant producing the greatest enhancement was determined independently. The value in the column marked S/B represents the ratio of light intensities with $10^{-16}$ mol of AP and that with no enzyme. The column marked Rel. presents the same ratio normalized to the results obtained with no enhancer (entry 11).

TABLE 3

| Entry | Surfactant | Concentration | S/B | Rel. |
|---|---|---|---|---|
| 1 | A | 0.01 g/L | 562 | 40.1 |
| 2 | B | 0.01 | 431 | 30.8 |
| 3 | C | 0.01 | 389 | 27.8 |
| 4 | D | 0.25 | 295 | 21.1 |
| 5 | E | 0.10 | 162 | 11.6 |
| 6 | F | 0.05 | 120 | 8.6 |
| 7 | G | 0.10 | 63 | 4.5 |
| 8 | H | 0.10 | 26 | 1.9 |
| 9 | I | 0.43 | 24 | 1.7 |
| 10 | J | 0.10 | 17 | 1.2 |
| 11 | None | — | 14 | 1 |

* Measured at 2 min.
A: poly(vinylbenzyltributylphosphonium chloride)-co-poly-(vinylbenzyltrioctylphosphonium chloride) (3:1 ratio of tributyl:trioctyl groups
B: polyvinylbenzylbenzyldimethylammonium chloride
C: poly(vinylbenzyltributylphosphonium chloride)-co-poly-(vinylbenzyltrioctylphosphonium chloride)-co-poly (vinyl-benzylfluorescein) (75:25:1)
D: poly(vinylbenzyltributylphosphonium chloride)
E: 1-trioctylphosphoniummethyl-4-tributylphosphonium-methylbenzene dichloride
F: Tween ™ 20, polyoxyethylene(20)sorbitan monolaurate
G: 1-trioctylphosphoniummethyl-4-tributylammonium-methylbenzene, mixed bromide chloride salt

TABLE 3-continued

| Entry | Surfactant | Concentration | S/B | Rel. |
|---|---|---|---|---|

H: SDS, sodium dodecyl sulfate
I: CTAB, cetyltrimethylammonium bromide
J: 1-trioctylammoniumnmethyl-4-tributylammoniummethylbenzene dichloride
The S/B values in entries 4-11 do not represent the maximum enhancement obtainable since light intensity continues to rise for >1 hour when these enhancers are used.

Example 22

Effect of the Concentration of Enhancer A on Light Intensity and Kinetics with Acridan Phosphate 1

A concentration dependence study was conducted in order to determine the amount of Enhancer A which produced the highest signal/background (S/B) level in the chemiluminescent reaction of acridan phosphate 1 with AP. Solutions of 1 in 0.1 M tris buffer, pH 8.5 containing 0.88 mM $Mg^{2+}$ and 0.5, 0.25, 0.1, 0.05 or 0.025 mg/mL of Enhancer A were prepared. Aliquots (100 $\mu$L) were equilibrated at 25° C. and reacted with $8\times10^{-16}$ moles of AP. The S/B values reported in Table 4 show that maximum light enhancement occurs with 0.005–0.01 g/L of enhancer.

TABLE 4

| Entry | Concentration | S/B 2 min | S/B 10 min |
|---|---|---|---|
| 1 | 0.0025 g/L | 431 | 262 |
| 2 | 0.005 | 714 | 500 |
| 3 | 0.010 | 660 | 562 |
| 4 | 0.025 | 399 | 360 |
| 5 | 0.050 | 247 | 240 |
| 6 | 0.10 | 212 | 163 |
| 7 | 0.50 | 40 | 84 |

Example 23

Linearity and Sensitivity of Detection of Alkaline Phosphatase with Acridan Phosphate 1

Figure 4:
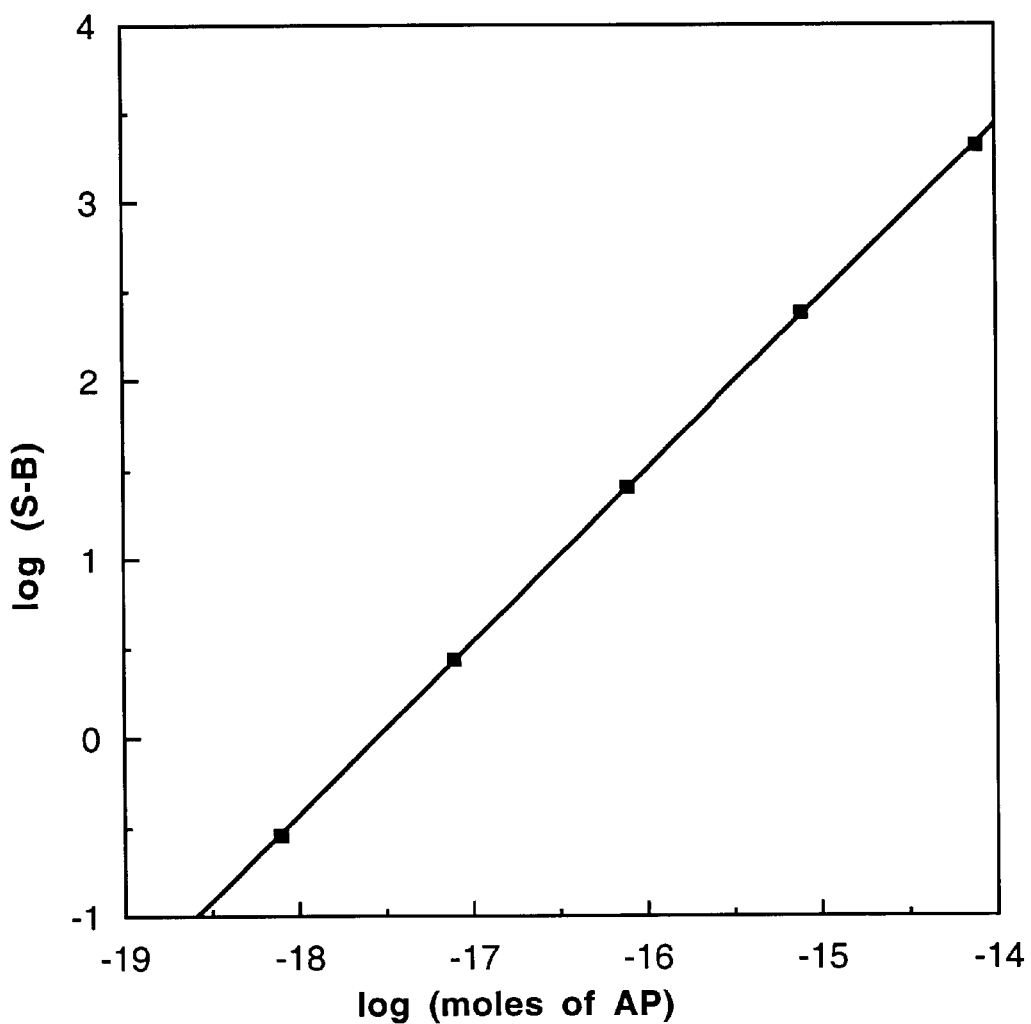
FIG. 4 is a graph relating the amount of AP to the maximum chemiluminescence intensity emitted by 100 $\mu$L of a reagent containing acridan phosphate 1 triggered at room temperature. Chemiluminescence emission was initiated at room temperature by addition of 10 $\mu$L of solutions of AP containing between $8\times10^{-15}$ mol and $8\times10^{-20}$ of enzyme to 100 $\mu$L of a 0.33 mM solution of acridan phosphate 1 in tris buffer, 0.1 M (pH 8.5) containing 0.88 mM $Mg^{+2}$ and 0.01 mg/mL of Enhancer A in the wells of a white microplate. The term S-B refers to the chemiluminescence signal (S) in Relative Light Units (RLU) in the presence of AP corrected for background chemiluminescence (B) in the absence of AP. The graph shows linear detection of alkaline phosphatase. The calculated detection limit (twice the standard deviation of the background) was determined to be $8\times10^{-19}$ mol under these conditions.

The sensitivity and linearity of detection of AP was determined using a reagent composition of the present invention containing acridan phosphate 1. To each of 3 wells in a 96-well white microplate 10 $\mu$L dilutions of AP containing between $8\times10^{-15}$ mol and $8\times10^{-20}$ mol of enzyme were added. A 100 $\mu$L aliquot of detection reagent comprising 0.33 mM solution acridan phosphate 1 in 0.1 M tris buffer, pH 8.5, 0.88 mM $MgCl_2$, 0.01 mg/mL of Enhancer A and 1% methanol was injected. Light intensities were measured after 2.5 min. FIG. 4 shows the linear detection of alkaline phosphatase. The term S-B refers to the chemiluminescence signal (S) in RLU in the presence of AP corrected for background chemiluminescence (B) in the absence of AP. The calculated detection limit (twice the standard deviation of the background) was determined to be $1.2\times10^{-19}$ mol under these conditions. A similar result was obtained using light intensities measured after 10 min.

Example 24

Chemiluminescent Detection of AP by pH Change

An alternate way to detect the light emitted by reaction of AP with 1 is to incubate a reagent composition containing 1 with AP at a first pH in the absence of enhancer and then rapidly raise the pH by injecting a solution of a strong base containing enhancer to cause a burst of light emission. A set of conditions which permitted the detection of $<10^{-18}$ mol of AP was devised.

Figure 5:
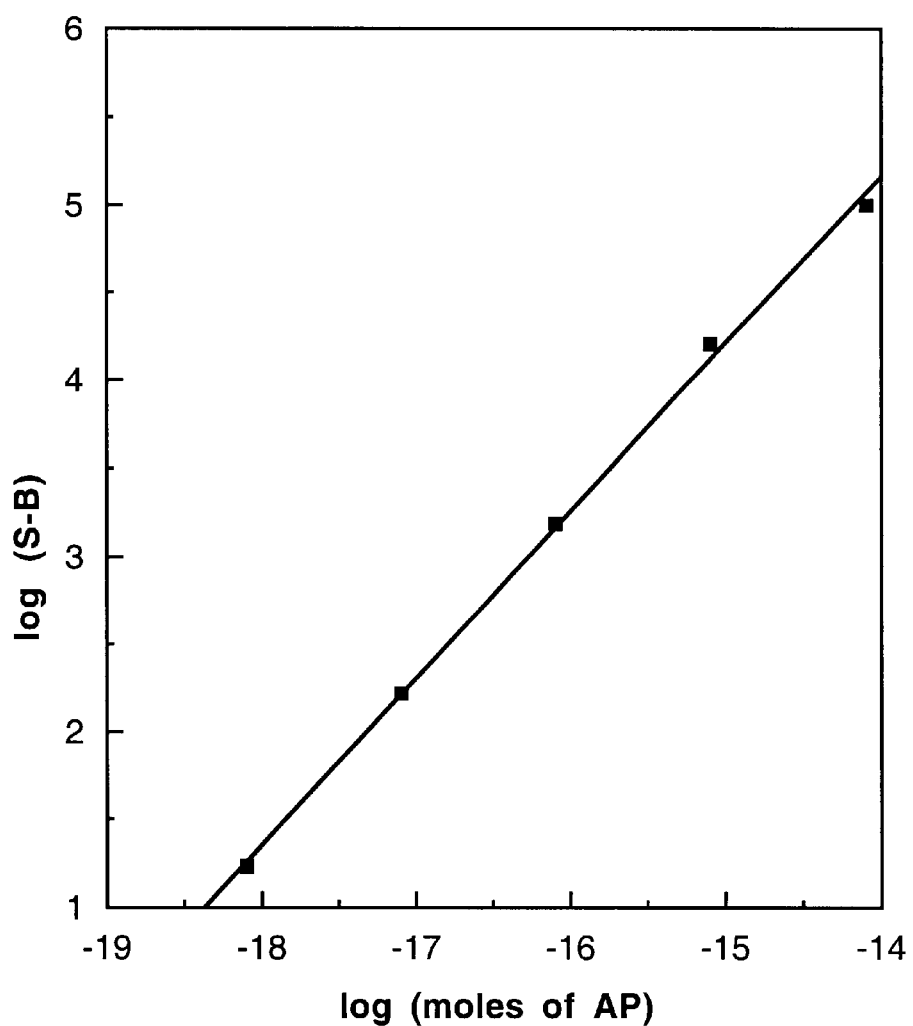
FIG. 5 is a graph relating the amount of AP to the total chemiluminescence intensity emitted by 100 $\mu$L of a reagent composition comprising 0.33 mm acridan phosphate 1 in 0.1 M tris buffer, pH 9, 0.88 mM $MgCl_2$. The composition was reacted with 10 $\mu$L of solutions of AP containing between $8\times10^{-15}$ and $8\times10^{-20}$ mol of enzyme or 10 $\mu$L of water as a reagent blank for 4 min at ambient temperature in the wells of a black microplate. A solution containing 0.5 mg/mL of Enhancer A in 1 N NaOH (100 $\mu$L) was injected and light intensity integrated for 10 sec. The graph shows linear detection of alkaline phosphatase.

A reagent composition (100 $\mu$L) comprising 0.33 mM acridan phosphate 1 in 0.1 M tris buffer, pH 9, 0.88 mM $MgCl_2$, was reacted with 10 $\mu$L of AP ($8\times10^{-15}$–$8\times10^{-20}$ mol) or 10 $\mu$L of water as a reagent blank for 4 min at ambient temperature in the wells of a black microplate. A solution containing 0.5 mg/mL of Enhancer A in 1 N NaOH (100 $\mu$L) was injected and light intensity integrated for 10 sec. Light intensity was a linear function of the amount of AP between $8\times10^{-15}$ and $8\times10^{-19}$ mol of AP as shown in FIG. 5.

Example 25

Chemiluminescent Detection of Acid Phosphatase and Inhibition by Tartrate

A reagent composition for chemiluminescent detection of acid phosphatase (AcP) comprised 0.1 M tris buffer, pH 7, 0.33 mM acridan phosphate 1 (from a 1:100 dilution of a 0.033 M methanol solution) and 0.01–0.1% of Enhancer A. Reaction of 100 $\mu$L of this composition with AcP (Sigma AcP LIN-TROL, reconstituted to 2.0 mL, 83 U/L) at ambient temperature in a test tube housed in a Turner TD-20e luminometer produced chemiluminescence which reached maximum intensity nearly instantaneously and remained nearly constant for several minutes. Addition of the protein bovine serum albumin to the detection reagent at 0.1% prolonged the duration of light emission significantly.

Addition of 5 $\mu$L of 0.04 M tartrate in citrate buffer (0.09 M, pH 4.8) caused complete extinction of light emission due to inhibition of enzyme activity by tartrate, a specific inhibitor for prostatic acid phosphatase. The quenching of emission was not due to a reduction of the pH since addition of 10 $\mu$L of citrate buffer caused only a 25% reduction in light intensity.

Example 26

Chemiluminescent Detection of AcP by pH Change

An alternate way to detect the light emitted by reaction of AcP with 1 is to incubate a reagent composition containing 1 and enhancer with AcP at a first pH and then rapidly raise the pH by injecting a solution of a strong base to cause a burst of light emission. A reagent composition (100 $\mu$L) comprising 0.33 mM acridan phosphate 1 in 0.1 M tris buffer, pH 7.0, 0.1% BSA and 0.01% Enhancer A was reacted with 3 $\mu$L of AcP (Sigma AcP LIN-TROL, reconstituted to 2.0 mL, 83 U/L) for 8 min at ambient temperature in a test tube. A solution of 1 N NaOH (50 $\mu$L) was injected and light intensity integrated for 4 min. Light intensity was three times the reagent blank.

Example 27

Western Blot Assay using PVDF Membrane

Figure 6:
FIG. 6 is a digitally scanned image of an x-ray film from a Western blot experiment detecting human transferrin via an AP-labeled antibody on a PVDF membrane with a chemiluminescent reagent composition. Dilutions of transferrin containing from 5000, 1000, 180, 30 and 5 pg, respectively, of protein were electrophoresed and transferred to the membrane. Protein was detected by briefly soaking the blot with a reagent composition containing 0.5 mg/mL of Enhancer A in 0.2 M 2-amino-2-methyl-l-propanol buffer, pH 9.6 containing 0.88 mM $MgCl_2$ and 0.66 mM acridan phosphate 1 and exposing to x-ray film for 1 min after a 10 min incubation time.

Compositions of the present invention were used to detect and quantify a protein, human transferrin in a Western blot with an AP-labeled antibody on a polyvinylidene difluoride (PVDF) membrane. Dilutions of transferrin containing from 5000, 1000, 180, 30 and 5 pg, respectively, of protein were electrophoresed and transferred to PVDF membranes (Millipore, Bedford, Mass.). The transferrin bands were blocked with and then reacted sequentially with goat anti-human transferrin and rabbit anti-goat-AP conjugate. The membranes were soaked briefly with reagents comprising 0.2 M 221 buffer, pH 9.6 containing 0.88 mM $MgCl_2$, 0.66 mM acridan phosphate 1 and 0.1 to 1 mg/mL of Enhancer A. The membranes were placed between transparent plastic sheets and exposed to X-ray film. FIG. 6 demonstrates the detection of human transferrin after 15 min with a 1 min exposure using a reagent composition containing 0.1 mg/mL of enhancer. The light produced using these compositions with varying amounts of the enhancer led to intense emission which could be imaged for at least 2 weeks.

Surprisingly it has been found that compositions containing 0.5 mg/mL of Enhancer A produced light emission whose intensity was nearly constant for 4 days with no change in the relative band intensities. Light emission produced on PVDF membranes persisted at useful levels for very long periods of time, exceeding a month. The 5 pg band could still be imaged with only a 20 min exposure after 5 weeks. This duration of emission at useful levels is without precedent.

Example 28

Western Blot using Nitrocellulose Membrane

A Western blot assay according to the procedures in Example 27 was performed using nitrocellulose membrane as the solid phase. Transferrin standards in the range of 5000–30 pg were used. A detection reagent which permitted detection of all levels of protein comprised 0.2 M 22 buffer, pH 9.6, 0.88 mM $MgCl_2$, 0.33 mM acridan phosphate 1 and 0.5 mg/mL of Enhancer A. Detection could be performed over several hours.

Example 29

Southern Blot Assay with Chemiluminescent Detection

The use of a composition of the present invention for the chemiluminescent detection of DNA on nitrocellulosse membranes by the technique of Southern blotting is demonstrated in the following example.

Avidin-AP conjugate was obtained from Cappel Products (Durham, N.C.). Bovine serum albumin (heat shocked) was purchased from Sigma Chemical Co. (St. Louis, Mo.). Human genomic DNA and human transferrin receptor cDNA were from Clontech (Palo Alto, Calif.). Biotinylated lambda DNA/HindIII fragments, biotin-7-dATP and the Nick Translation kit were from Life Technologies, restriction endonuclease HindIII was from Boehringer-Mannheim (Indianapolis, IN), and nitrocellulose membrane from Schleicher & Schuell Inc (Keene, N.H.). X-ray film was X-OMAT AR from Kodak (Rochester, N.Y.).

Human genomic DNA (19.5 $\mu$g) was cleaved with HindIII to completion and divided into 13 $\mu$g and 6.5 $\mu$g portions. Restricted DNA was purified by phenol/chloroform extraction and ethanol precipitation. Purified DNA was separated by electrophoresis on 0.75% agarose gel with 40 mmol/L Tris-acetate, 2 mmol/L EDTA, pH 8.0 as the elution buffer. Following electrophoresis, the gel was rinsed with water, equilibrated for 12 min with 0.25 mol/L HCl, rinsed with water again, incubated in 0.5 mol/L NaOH, 1.5 mol/L NaCl for 15 min then in a fresh change of the same solution for 30 min, rinsed with water, and incubated in three changes of 1 mol/L tris, 1.5 mol/L NaCl, pH 7.5 for 15 min each.

Nitrocellulose membrane was soaked sequentially with water for two min and 10×SSC for 30 min. DNA was transferred to the membrane by capillary blotting overnight in 10×SSC. The membrane was washed by gentle agitation in 10×SSC for 10 min at room temperature and air-dried on Whatman 3MM blotting paper for 30 min and baked at 80° C. under vacuum for 2 h.

The membrane was soaked in 6×SSPE (20×SSPE is 3 mol/L NaCl, 0.2 mol/L $NaH_2PO_4$, 20 mmol/L EDTA, pH 7.4) followed by prehybridization for 3 h at 42° C. in pre-hybridization solution: 6×SSPE, 50% freshly deionized formamide, filtered 5×Denhardt's solution (50×is 1% Ficoll 400, 1% PVP, 1% BSA (initial fraction by heat shock)), filtered 1% SDS and 200 $\mu$g/mL sheared, denatured herring sperm DNA. The hybridization probe, human transferrin receptor cDNA was labeled with biotin-7-dATP by nick translation according to the manufacturers instructions. Genomic DNA was hybridized overnight at 42° C in 6×SSPE, 45% formamide, filtered 5×Denhardt's, 1% SDS, 200 $\mu$g/mL herring sperm DNA with 300 $\mu$g/mL denatured biotinylated probe. The biotinylated probe was denatured by boiling 4 min and cooling 10 min at 0° C. The membrane was washed twice with 0.5×SSC, 0.4% SDS at 25° C. for 5 min, three times with 0.5×SSC, 0.4% SDS at 55° C. for 10 min, once with 2×SSC at 25° C. for 5 min, twice with TBS (50 mmol/L Tris-HCl, pH 7.4, 0.15 mol/L NaCl) for 3 min. After the wash step, the membrane was blocked at 63° C. for 1 h in filtered 3% BSA, 100 mmol/L Tris-HCl, pH 7.4, 0.15 mol/L NaCl and washed in T-TBS (0.05% Tween 20 in TBS) for 1 min.

The blocked membrane was incubated with a 1:2000 dilution of avidin-AP in T-TBS for 12 min followed by four fresh changes of T-TBS for 5, 10, 15 and 20 min followed by a final wash with TBS for 5 min. Excess buffer was drained off and blots soaked in the detection reagent described in Example 27 for 3 min. Excess reagent was drained off, and the blots placed between transparent sheets and exposed to X-ray film.

The single copy gene was detected at 10.5 and 5.2 kbp by soaking the membrane with detection reagent and exposure to x-ray film for varying lengths of time. After an incubation period of 12 min, a band corresponding to the single copy gene in both fractions was visible with a 5 min exposure to film using a reagent of the present invention. Shorter incubation times also produced excellent images. Multiple exposures could be easily performed for a day.

Example 30

Effect of Lucigenin on the Chemiluminescence Profile

Figure 7:
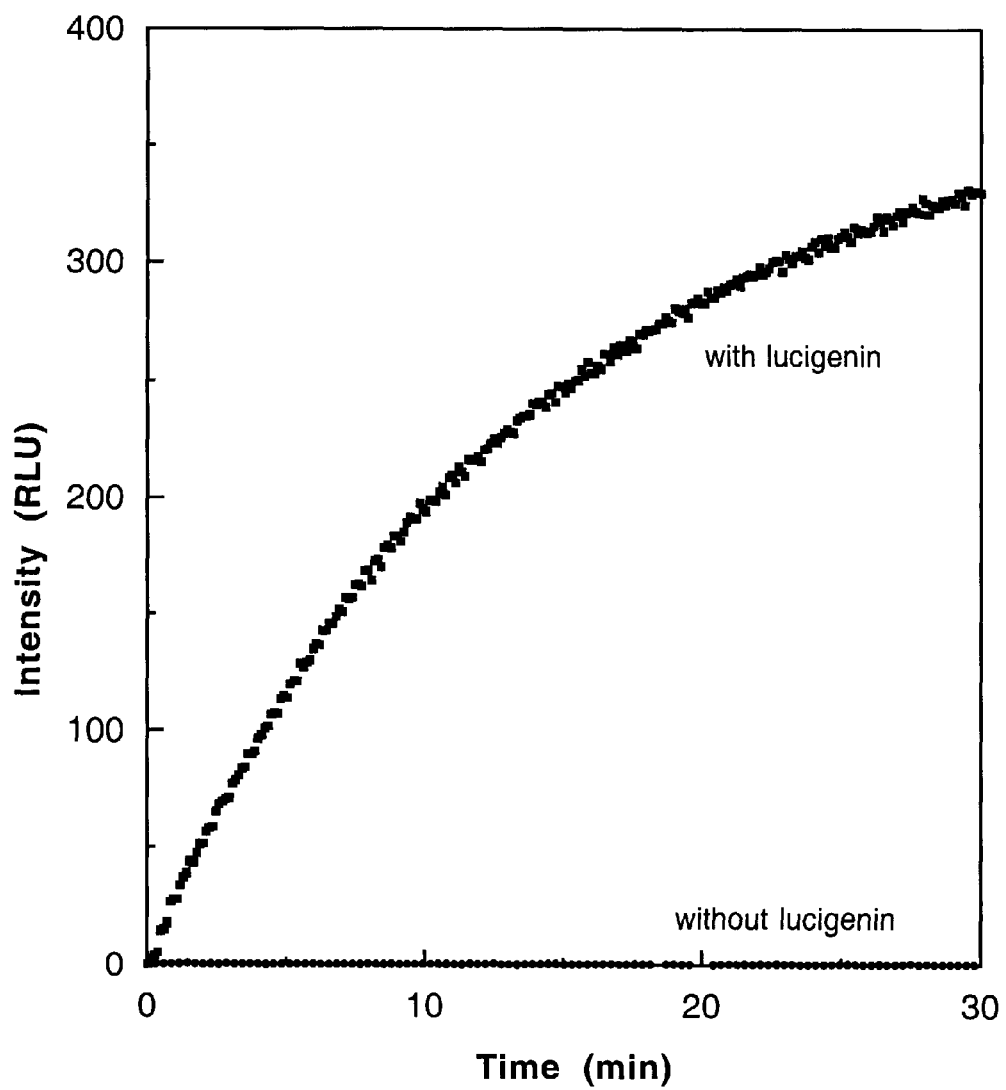
FIG. 7 is a graph showing the effect on chemiluminescence production from reaction of 5 with alkaline phosphatase (AP) by adding lucigenin to the reaction solution. Equal volumes of two solutions containing 5 in buffer were reacted with $8\times10^{-16}$ moles of alkaline phosphatase (AP). One solution also contained 6.4 $\mu$M lucigenin.

The higher light intensity afforded by the addition of lucigenin to the reaction of acridan phosphate 5 with AP is shown by the plots in FIG. 7. Reaction of 100 $\mu$L portions of a solution of 5 (0.66 mM) in 0.1 M tris buffer, pH 8.8 containing 0.88 mM $MgCl_2$, with $8\times10^{-16}$ mol of AP at 25° C. were conducted in the presence and absence of 6.4 $\mu$M lucigenin. FIG. 7 shows the much higher light intensity resulting from incorporation of lucigenin into the solution.

Example 31

Chemiluminescent Detection of Alkaline Phosphatase with Compound 5

Figure 8:
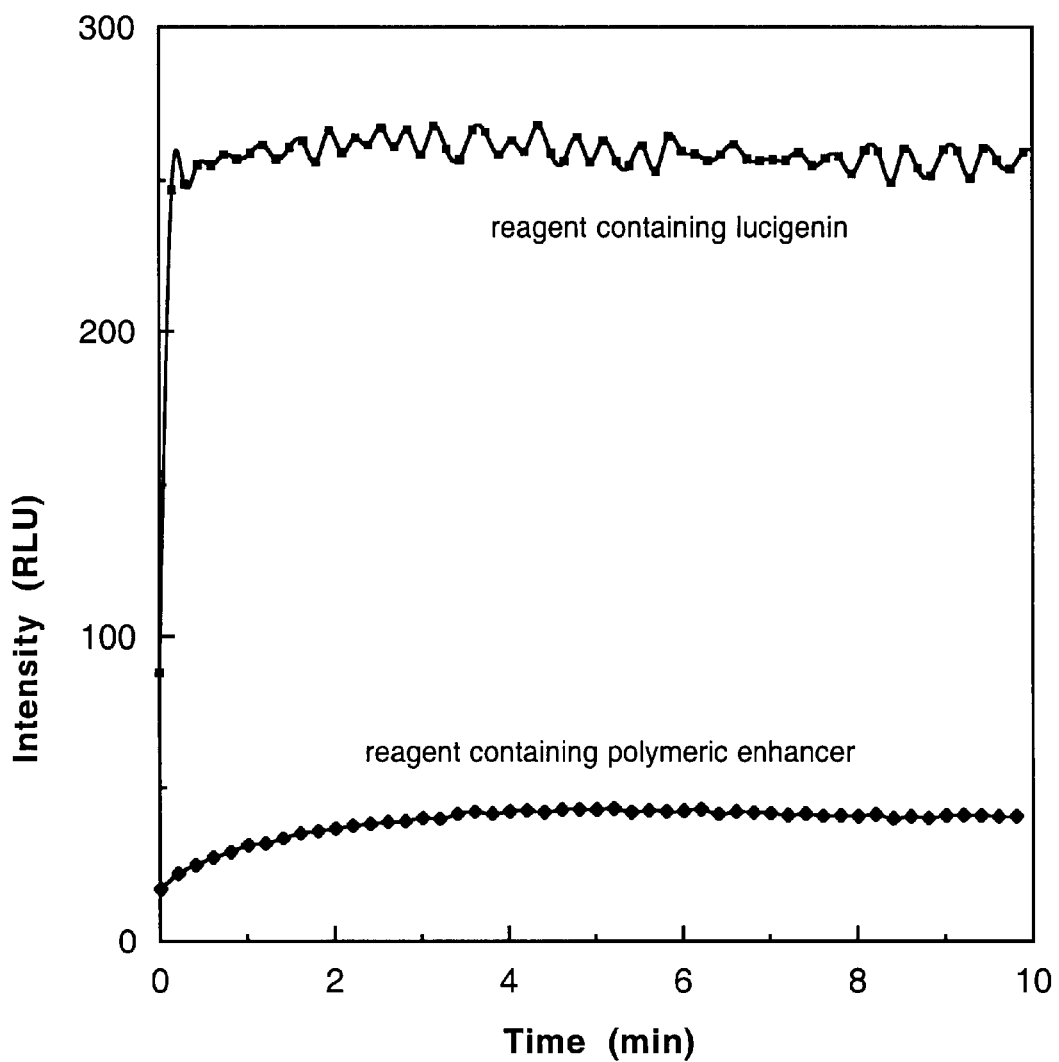
FIG. 8 is a graph showing the time profile of the chemiluminescence intensity emitted by 100 $\mu$L of Reagent A consisting of 0.1 M tris buffer, pH 8,8, 6.4 $\mu$M lucigenin, 0.66 mM acridan phosphate 5 (from a 1:100 dilution of a 0.066 M methanol solution), 1 mg/mL sodium dodecyl sulfate, 0.01 mg/mL $Na_2SO_3$, 0.033% (w/v) TWEEN 20 and 0.88 mM $MgCl_2$ triggered at room temperature by addition of $8\times10^{-16}$ mol of AP. The figure also shows for comparison the chemiluminescence profile from a reagent composition containing 5 and a cationic polymeric surfactant enhancer (0.25 TB/TO).

A highly effective reagent composition for chemiluminescent detection of alkaline phosphatase comprised 0.1 M tris buffer, pH 8.8, 6.4 $\mu$M lucigenin, 0.66 mM compound 5, 1 mg/mL SDS, 0.01 mg/mL $Na_2SO_3$, 0.033% (w/v) TWEEN 20 and 0.88 mM $MgCl_2$. Reaction of 100 $\mu$L of this composition with $8\times10^{-16}$ mol of AP at 25° C. produced chemiluminescence which reached maximum intensity in 2 min. FIG. 8 shows the comparison with a reagent composition containing 5 and the cationic polymeric surfactant enhancer poly(vinylbenzyltributylphosphonium chloride)-co-poly-(vinylbenzyltrioctylphosphonium chloride), containing about a 3:1 ratio of tributyl:trioctyl groups (0.25TB/TO), triggered at 37° C. Compositions containing the latter polymeric surfactant were found previously to be the highest levels of chemiluminescence in the absence of a CAC.

Example 32

Linearity and Sensitivity of Detection of Alkaline Phosphatase

The sensitivity and linearity of detection of AP was determined using a reagent composition containing compound 5 and lucigenin (reagent A) and compared to the results achievable using a reagent composition containing compound 5 and 0.25TB/TO (reagent B). The reagents have the following composition:

| Reagent A | Reagent B |
|---|---|
| Compound 5, 0.66 mM | Compound 5, 0.66 mM |
| 0.1 M tris buffer, pH 8.8 | 0.2 M 221 buffer, pH 9.6 |
| 0.01 or 0.88 mM $MgCl_2$ | 0.88 mM $MgCl_2$ |
| lucigenin, 6.4 $\mu$M | 0.25 TB/TO, 0.5 mg/mL |
| SDS, 1 mg/mL | |
| $Na_2SO_3$, 0.01 mg/mL | |
| TWEEN 20, 0.033% (w/v) | |

Figure 9:
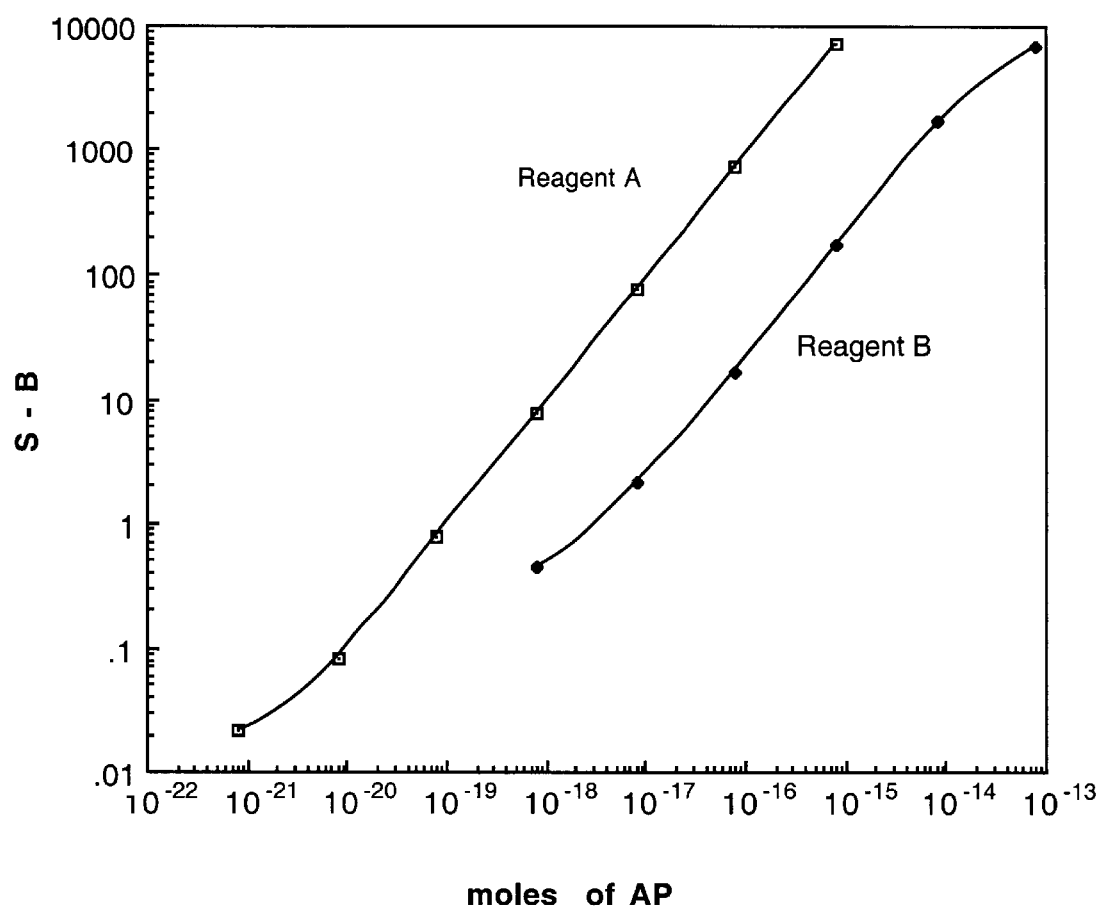
FIG. 9 is a graph relating the amount of AP to the maximum chemiluminescence intensity emitted by 100 $\mu$L of a reagent composition of the present invention (reagent A) containing acridan phosphate 5, lucigenin, SDS and TWEEN 20 triggered at 25° C. For comparison, a similar graph is presented from a set of experiments using a reagent composition (reagent B) containing the same acridan phosphate and (0.25TB/TO) but without lucigenin triggered at 37° C. Chemiluminescence emission was initiated by addition of 10 $\mu$L of solutions of AP containing between $8\times10^{-13}$ and $8 \times 10^{-22}$ mol of enzyme to 100 µL of the respective reagent compositions in the wells of a white microplate. The term S-B refers to the chemiluminescence signal (S) in Relative Light Units (RLU) in the presence of AP corrected for background chemiluminescence (B) in the absence of AP. The graph shows that reagent A including lucigenin achieves a 100-fold lower detection limit for AP.

To each of 3 wells in a 96-well white microplate, 10 $\mu$L dilutions of AP containing between $8 \times 10^{-13}$ mol and $8 \times 10^{-22}$ mol of enzyme were added 100 $\mu$L aliquots of detection reagent A or B. Light intensities were measured after 2.5 min. FIG. 9 shows the linear detection of alkaline phosphatase. The calculated detection limit (two standard deviations over the background) was determined to be $3.5 \times 10^{-21}$ mol for reagent A and $1.2 \times 10^{-19}$ mol for reagent B.

Example 33

Chemiluminescent Detection with Compounds 1–13

In the manner of Example 30, compositions containing 0.66 mM of each of compounds 1–13 with 0 and 6.4 $\mu$M lucigenin were reacted with $8 \times 10^{-16}$ moles of AP at 25° C. Each demonstrated significantly more intense chemiluminescence when lucigenin was in the reaction solution.

Example 34

Linearity and Sensitivity of Detection of AP using Compounds 7–12

Figure 10:
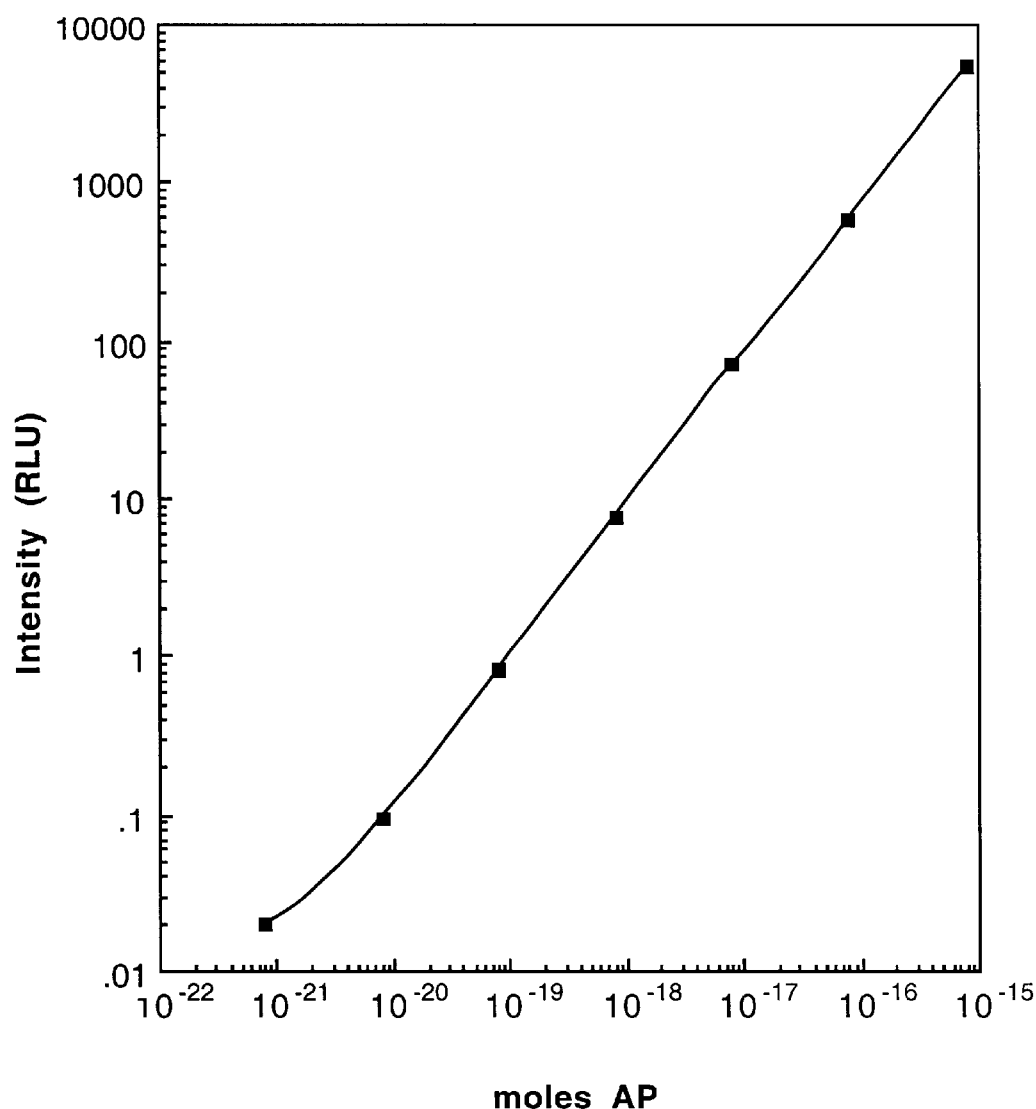
FIG. 10 is a graph relating the amount of AP to the maximum chemiluminescence intensity emitted by 100 µL of a reagent composition comprising 0.66 mM acridan phosphate 7 in 0.1 M tris buffer, pH 8,8, 6.4 µM lucigenin, 1 mg/mL sodium dodecyl sulfate, 0.01 mg/mL $Na_2SO_3$, 0.033% (w/v) TWEEN 20 and 0.88 mM $MgCl_2$. The composition was reacted with 10 µL of solutions of AP containing between $8 \times 10^{-15}$ and $8 \times 10^{-22}$ mol of enzyme or 10 µL of water as a reagent blank and measured after 75 sec at ambient temperature in the wells of a black microplate.
Figure 11:
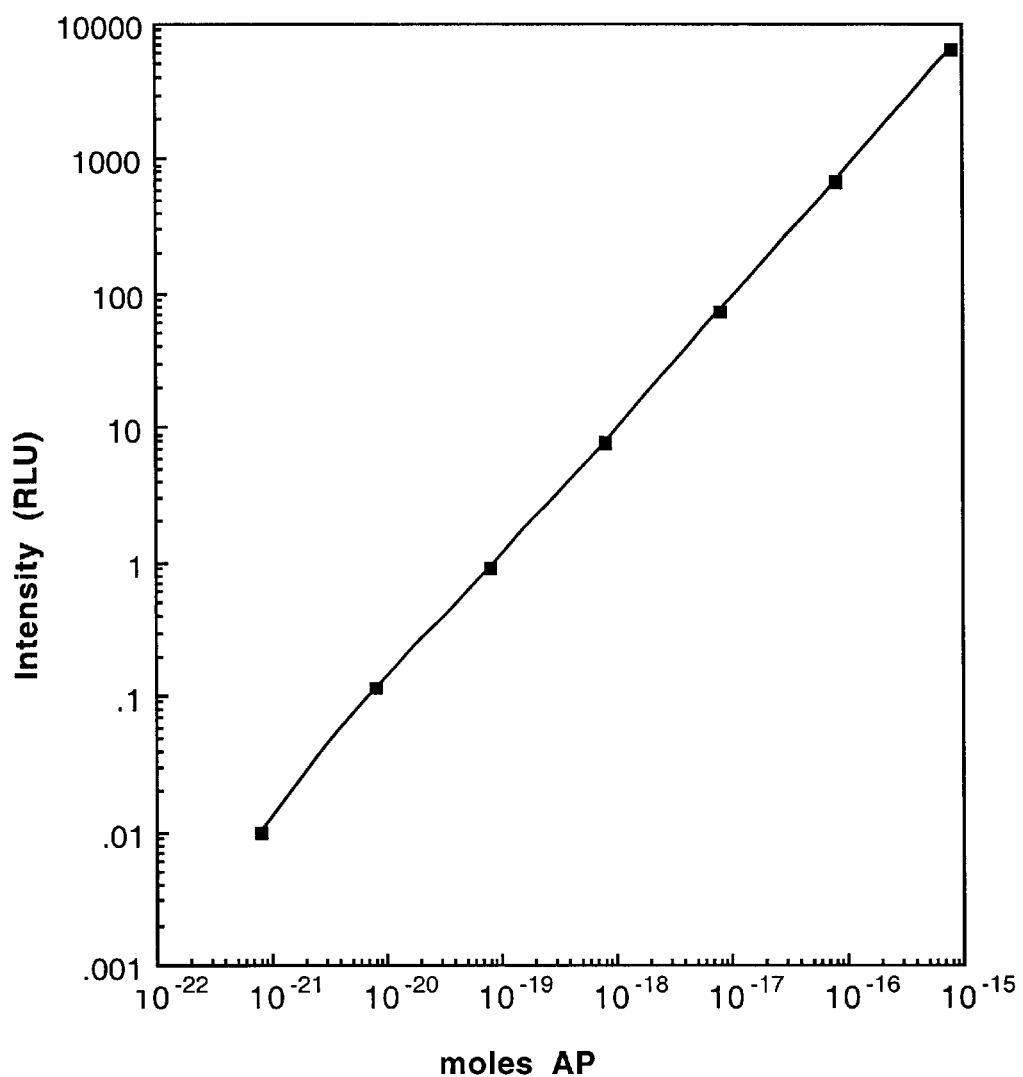
FIG. 11 is a graph relating the amount of AP to the maximum chemiluminescence intensity emitted by 100 µL of a reagent composition comprising 0.66 mM acridan phosphate 8 in 0.1 M tris buffer, pH 8,8, 6.4 µM lucigenin, 1 mg/mL sodium dodecyl sulfate, 0.01 mg/mL $N_2SO_3$, 0.033% (w/v) TWEEN 20 and 0.88 mM $MgCl_2$. The composition was reacted with 10 µL of solutions of AP containing between $8 \times 10^{-15}$ and $8 \times 10^{-22}$ mol of enzyme or 10 µL of water as a reagent blank and measured after 75 sec at ambient temperature in the wells of a black microplate.
Figure 18:
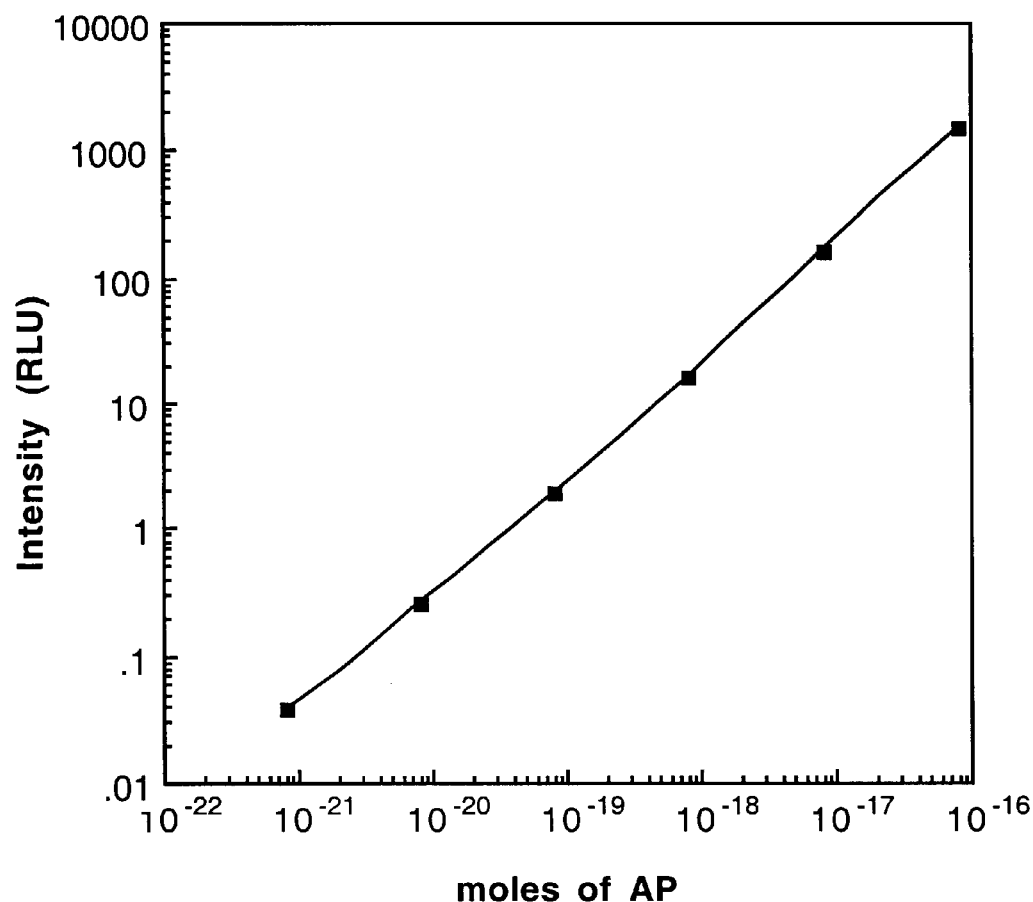
FIG. 18 is a graph relating the amount of AP to the maximum chemiluminescence intensity emitted by 100 µL of a reagent composition comprising 0.66 mM acridan phosphate 12 in 0.1 M tris buffer, pH 8,8, 6.4 µM lucigenin, 1 mg/mL sodium dodecyl sulfate, 0.01 mg/mL $Na_2SO_3$, 0.033% (w/v) TWEEN 20 and 10 µM $MgCl_2$. The composition was reacted with 10 µL of solutions of AP containing between $8 \times 10^{-15}$ and $8 \times 10^{-22}$ mol of enzyme or 10 µL of water as a reagent blank and measured after 75 sec at ambient temperature in the wells of a black microplate.

In the manner of Example 32, reagents were prepared according to the composition of reagent A substituting 0.66 mM of each of compounds 7–12 in place of compound 5. To 100 $\mu$L portions of each of these reagents was added 10 $\mu$L dilutions of AP containing between $8 \times 10^{-16}$ mol and $8 \times 10^{-22}$ mol of enzyme or 10 $\mu$L of water for the reagent blank. In each case, the reaction solution containing $8 \times 10^{-21}$ mol of enzyme produced a peak signal within about 2 minutes which was higher than the blank. FIGS. 10 and 11 and 18 depict the results for compounds 7, 8, and 12 respectively.

Example 35
Time profile of Chemiluminescence using Compound 7

Figure 12:
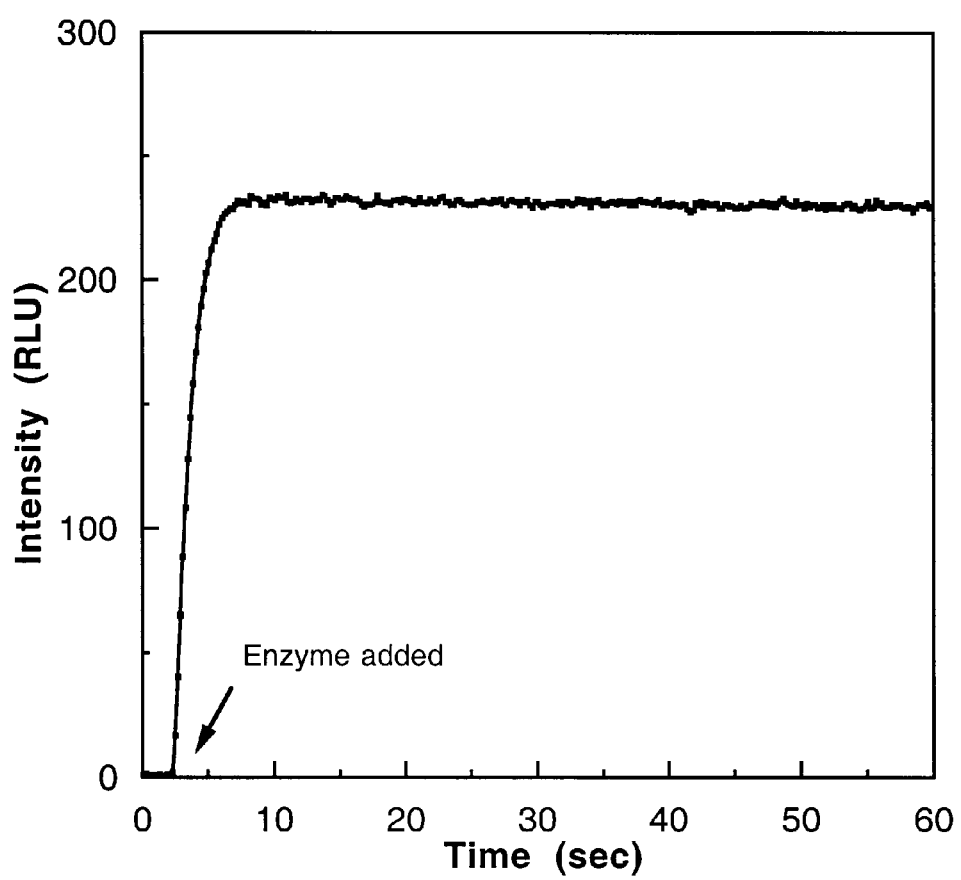
FIG. 12 is a graph showing the rapid generation of chemiluminescence emitted by 100 µL of a reagent consisting of 0.1 M tris buffer, pH 8,8, 6.4 µM lucigenin, 0.66 mm acridan phosphate 7 (from a 1:100 dilution of a 0.066 M methanol solution), 1 mg/mL sodium dodecyl sulfate, 0.01 mg/mL $Na_2SO_3$, 0.033% (w/v) TWEEN 20 and 0.88 mM $MgCl_2$ triggered at room temperature by addition of $8 \times 10^{-16}$ mol of AP.

The rapid generation of chemiluminescence emitted by a reagent composition containing compound 7 is demonstrated in the following experiment. A 100 $\mu$L portion of a reagent consisting of 0.1 M tris buffer, pH 8,8, 6.4 $\mu$M lucigenin, 0.66 mM acridan phosphate 7), 1 mg/mL sodium dodecyl sulfate, 0.01 mg/mL $Na_2SO^{-3}$, 0.033% (w/v) TWEEN 20 and 0.88 mM $MgCl_2$ was reacted with $8 \times 10^{-16}$ mol of AP at room temperature. The chemiluminescence intensity reached a stable plateau in under 5 sec as shown in FIG. 12.

Example 36
Increase in Chemiluminescence Intensity with Various CACs

Test solutions were prepared containing 21 mM of CAC 1–11 in DMSO. These were diluted 1:1000 into a solution of acridan phosphate compound 5 in 0.1 M tris buffer, pH 8.8 containing 0.88 mM $MgCl_2$. Triplicate 100 $\mu$L portions of each of the final reagent compositions were reacted with $4 \times 10^{-16}$ mol of AP at room temperature in a white microwell plate. Table 5 shows the effect on plateau intensity (S), measured at 36 min and signal/background (S/B) for each CAC. Each produced higher peak signal S and S/B than a control without CAC.

TABLE 5

| CAC | S at 36 min |
|---|---|
| 1 | 2602 |
| 2 | 45.3 |
| 3 | 5963 |
| 4 | 4645 |
| 5 | 34.7 |
| 6 | 72.3 |
| 7 | 61.6 |
| 8 | 19.1 |
| 9 | 781 |
| 10 | 21.1 |
| 11 | 9.3 |
| None | 2.8 |

1: Lucigenin
2: Basic Red 29
3: Basic Blue 66
4: Basic Blue 41
5: 3,3'-Diethylthiadicarbocyanine iodide
6: 3,3'-Diethyl-9-methylthiacarbocyanine iodide
7: 3,3'-Diethylselenacarbocyanine iodide
8: 3,3'-Diethylthiacyanine iodide
9: IR-1040
10: 5-[3-Ethoxy-4-(3-ethyl-5-methyl-2(3H)-benzothiazolyl-idene)-2-butenylidene]-3-ethyl-2-[(3-ethyl-4,5-diphenyl-2(3H)-thiazolylidene) methyl]-4,5-dihydro-4-oxothiazolium iodide
11: IR-786 perchlorate Example 37
Effect of Concentration of CAC on Chemiluminescent Reaction of 5 with AP Chemiluminescent detection of AP with compositions of the present invention can be performed over a broad range of concentration of CAC. Compositions containing 0.66 mM compound 5 in 0.1 M tris buffer, pH 8.8 containing 0.88 mM $MgCl_2$ were prepared with varying concentrations of lucigenin ranging from 6.4 mM to 6.4 nM by 10-fold serial dilutions of a stock lucigenin solution. The control contained no lucigenin. Test solutions (100 $\mu$L, 5 replicates) containing between 6.4 mM and 6.4 nM reacted with $4 \times 10^{-16}$ mol of AP produced a higher signal (S) than the control after a 3.5 min incubation at room temperature.

Example 38
Effect of Concentration of Anionic Surfactant on Chemiluminescent Reaction of 5 with AP Chemiluminescent detection of AP with compositions of the present invention can be performed over a broad range of concentration of the anionic surfactant SDS. Compositions containing 0.66 mM compound 5 and 0.88 mM $MgCl_2$ in 0.1 M tris buffer, pH 8.8 with varying concentrations of SDS ranging from 10 mg/mL to 10 µg/mL were prepared. The control contained no SDS. Test solutions (100 µL, 5 replicates) reacted with $4 \times 10^{-16}$ mol of AP produced a faster rise to peak signal at room temperature than the control.

Example 39

Effect of Concentration of Nonionic Surfactant on Chemiluminescent Reaction of 5 with AP Chemiluminescent detection of AP with compositions of the present invention can be performed over a broad range of concentration of the non-ionic surfactant TWEEN 20. Compositions according to Reagent A in Example 32 were prepared but with 21 µM lucigenin and varying concentrations of the non-ionic surfactant ranging from 1.0% to 0.001% and lacking the $Na_2SO_3$. The control contained no non-ionic surfactant. The test solutions (100 µL, 5 replicates) and the controls were reacted with $4 \times 10^{-16}$ mol of AP at room temperature. Each test solution was effective in extending the duration of chemiluminescence at or near maximum intensity.

Example 40

Effect of Concentration of Sodium Sulfite on Chemiluminescent Reaction of 5 with AP Chemiluminescent detection of AP with compositions of the present invention can be performed over a broad range of concentration of sodium sulfite ($Na_2SO_3$). Compositions according to Reagent A in Example 32 were prepared but with varying concentrations of $Na_2SO_3$ ranging from 1.0 mg/mL to 1.0 µg/mL. The control contained no $Na_2SO_3$. Each test solution (100 µL, 5 replicates) produced a lower background signal (B) in the absence of AP and a higher signal (S) than the control when reacted with $4 \times 10^{-16}$ mol of AP after a 3.5 min incubation at room temperature. In this experiment, the maximum signal was obtained using 1.0 µg/mL while the maximum S/B was obtained using 1.0 mg/mL.

Example 41

Western Blot Assay

A composition of the present invention were used to detect and quantify a protein, human transferrin in a Western blot with an AP-labeled antibody on a polyvinylidene difluoride (PVDF) membrane. Dilutions of transferrin containing from 5000, 1000, 180, 30 and 5 pg, respectively, of protein were electrophoresed and transferred to PVDF membranes (Millipore, Bedford, Mass.). The transferrin bands were blocked with and then reacted sequentially with goat anti-human transferrin and rabbit anti-goat-AP conjugate. The membranes were soaked briefly with reagents comprising 0.1 M tris buffer, pH 8.8 containing 0.88 mM $MgCl_2$, 0.66 mM compound 5 and 64 µM lucigenin. The membranes were placed between transparent plastic sheets and exposed to X-ray film. The bands for human transferrin were detected after 10 min with a 2.5 min exposure. The light produced using this composition led to intense emission which could be imaged for several hours.

Similar results were obtained using nitrocellulose blotting membrane instead of PVDF membrane.

Example 42

Southern Blot Assay

A representative example of the use of a reagent of the present invention in a Southern blot assay is demonstrated in the following example.

Avidin-AP conjugate was obtained from Cappel Products (Durham, N.C.). Bovine serum albumin (heat shocked) was purchased from Sigma Chemical Co. (St. Louis, Mo.). Mouse genomic DNA was from Clontech (Palo Alto, Calif.). Biotinylated lambda DNA/HindIII fragments, biotin-7-dATP and the Nick Translation kit were from Life Technologies, restriction endonuclease EcoRI was from Boehringer-Mannheim (Indianapolis, Ind.), and nylon membrane from Micron Separations Inc (Westborough, Mass.). X-ray film was X-OMAT AR from Kodak (Rochester, N.Y.).

Mouse genomic DNA (30 µg) was cleaved with EcoRI to completion. Two and four µg portions were purified by phenol/chloroform extraction and ethanol precipitation. Purified DNA was separated by electrophoresis on 0.75% agarose gel with 40 mmol/L Tris-acetate, 2 mmol/L EDTA, pH 8.0 as the elution buffer. Following electrophoresis, the gel was rinsed with water, equilibrated for 12 min with 0.25 mol/L HCl, rinsed with water again, incubated in 0.5 mol/L NaOH, 1.5 mol/L NaCl for 15 min then in a fresh change of the same solution for 30 min, rinsed with water, and incubated in three changes of 1 mol/L tris, 1.5 mol/L NaCl, pH 7.5 for 15 min each.

Nylon membrane was soaked sequentially with water for two min and 10xSSC for 30 min. DNA was transferred to the membrane by capillary blotting overnight in 10xSSC. The membrane was washed by gentle agitation in 10xSSC for 10 min at room temperature and air-dried on Whatman 3MM blotting paper for 30 min and baked at 80° C. under vacuum for 2 h.

The membrane was soaked in 6xSSPE (20xSSPE is 3 mol/L NaCl, 0.2 mol/L $NaH_2PO_4$, 20 mmol/L EDTA, pH 7.4) followed by prehybridization for 3 h at 42° C. in pre-hybridization solution: 6xSSPE, 50% freshly deionized formamide, filtered 5xDenhardt's solution (50x is 1% Ficoll 400, 1% PVP, 1% BSA (initial fraction by heat shock)), filtered 1% SDS and 200 µg/mL sheared, denatured herring sperm DNA. The hybridization probe, oncogene probe v-mos DNA (PanVera Corp., Madison, Wis.) was labeled with biotin-7-dATP by nick translation according to the manufacturers instructions. Genomic DNA was hybridized overnight at 42° C. in 6xSSPE, 45% formamide, filtered 5xDenhardt's, 1% SDS, 200 µg/mL herring sperm DNA with 500 ng of denatured biotinylated probe. The biotinylated probe was denatured by boiling 4 min and cooling 10 min at 0° C. The membrane was washed twice with 0.5x SSC, 0.4% SDS at 25° C. for 15 and 35 min respectively, three times with 0.5xSSC, 0.4% SDS at 50° C. for 10 min, once with 2xSSC at 25° C. for 5 min, twice with TBS (50 mmol/L Tris-HCl, pH 7.4, 0.15 mol/L NaCl) for 3 min. After the wash step, the membrane was blocked at 65° C. for 1 h in filtered 3% BSA, 100 mmol/L Tris-HCl, pH 7.4, 0.15 mol/L NaCl and washed in T-TBS (0.05% Tween 20 in TBS) for 1 min.

The blocked membrane was incubated with a 1:2000 dilution of avidin-AP in T-TBS for 12 min followed by four fresh changes of T-TBS for 5, 10, 15 and 20 min followed by a final wash with TBS for 5 min. Excess buffer was drained off and blots soaked in either the detection reagent described in Example 41 for 4 min. Excess reagent was drained off, and the blots placed between transparent sheets and exposed to X-ray film.

The single copy gene was detected at 14.5 kbp by soaking the membrane with detection reagent and exposure to x-ray film for varying lengths of time. After an incubation period of 9 min, a band corresponding to the single copy gene in both fractions was visible with a 5 min exposure to film. Multiple exposures could be performed for a day by using longer exposures.

Example 43

Chemiluminescent Immunoassay of hCG

A method for detection of hCG by chemiluminescent immunoassay was performed on the IMMULITE Automated Analyzer using an IMMULITE kit supplied by Diagnostic Products Corp. (Los Angeles, Calif.) according to the protocol provided by the manufacturer. Reagent A of Example 32 was substituted for the detection reagent supplied in the kit. The software was modified to allow a shorter substrate incubation. All data points are the average of triplicate tests except for blank readings which were the average of 5 tests of the sample diluent. Analytes were prepared by serial dilution of special calibrators with the standard diluents supplied in the kit. Chemiluminescence measurements were made at 1.5 minutes after substrate introduction.

A minor modification of the injection mechanism was made to minimize the dead volume of chemiluminescent reagent in the tubing. The substrate heater was disconnected and an 18"×1/16" OD clear teflon tubing wrapped in black electrical tape having flared ends was connected directly between the substrate pump and the gray substrate dispensing nozzle. A similar length of the same teflon tubing was attached to the inlet port of the substrate pump. This inlet tubing was placed in the bottle containing the substrate. No attempt was made to preheat or temperature control the substrate. Insensitivity to temperature is indicated by the tight CV's even in the absence of external substrate temperature control.

Figure 13:
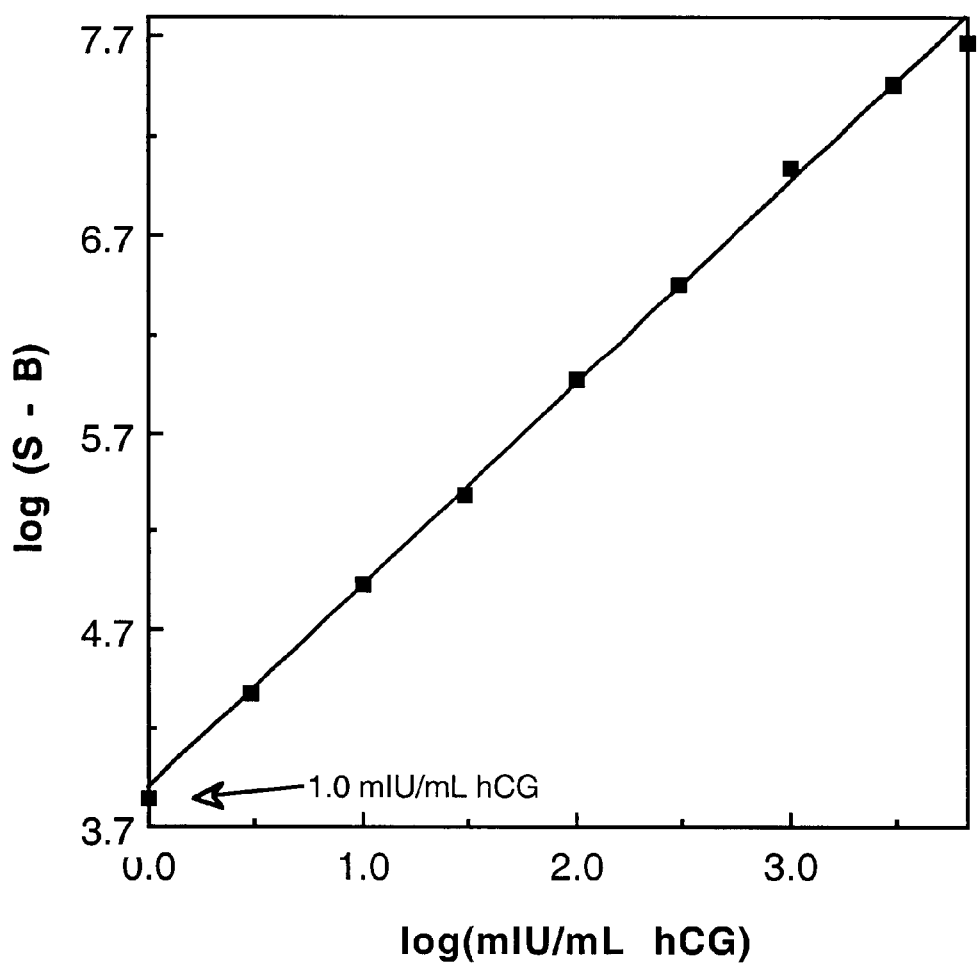
FIG. 13 is a graph showing the results of a chemiluminescent immunoassay for human chorionic gonadotropin using a detection reagent of the invention.

Independent tests on rapid reading luminometers indicate that the substrate can be read with as little as 10 seconds incubation time yielding no loss of sensitivity or accuracy. Assay results as shown in FIG. 13 and Table 6 demonstrate the utility of the present compositions in a sandwich-type immunoassay.

TABLE 6

IMMULITE hCG Assay Tabulated Data

| mIU/mL hCG | Intensity (CPS) | % CV |
|---|---|---|
| 6675 | 47332040 | 3.8 |
| 3000 | 29174720 | 1.2 |
| 1000 | 11031867 | 1.5 |
| 300 | 2906560 | 2.5 |
| 100 | 977760 | 2.6 |
| 30 | 288883 | 0.7 |
| 10 | 133573 | 6.3 |
| 3 | 71507 | 5.9 |
| 1 | 54738 | 7.4 |
| Blank | 47634 | 9.0 |

Example 44

Rapid Chemiluminescent Immunoassay of TSH

A method for detection of TSH by chemiluminescent immunoassay was performed on the IMMULITE Automated Analyzer using an IMMULITE RTH Rapid TSH Assay kit from Diagnostic Products Corp. according to the manufacturer's protocol with modifications as described in Example 43. Reagent A of Example 32 was substituted for the detection reagent supplied in the kit.

The reagent background was tested by removing the antibody conjugates from a Third Generation TSH test wedge, carefully washing the wedge and replacing the contents with Type 1 water. The observed substrate background was approximately 5000 counts per second. This indicates that the non-specific binding background is several times the reagent background. Therefore, it is possible that reoptimization of the biochemistry in the wedge could significantly extend the sensitivity of several of the assays and/or allow a reduction of the biochemical incubation time. Chemiluminescence measurements were made at 1.5 minutes after substrate introduction.

TABLE 7

IMMULITE RTH Rapid TSH Assay Data

| $\mu$IU/mL TSH | Intensity (CPS) | % CV |
|---|---|---|
| 75 | 17370000 | 0.9 |
| 10 | 2263413 | 5.3 |
| 1 | 202120 | 2.6 |
| 0.3 | 72357 | 2.6 |
| 0.1 | 36887 | 1.5 |
| 0.03 | 25607 | 2.6 |
| 0.01 | 22647 | 5.0 |
| Blank | 20810 | 2.0 |

Figure 14:
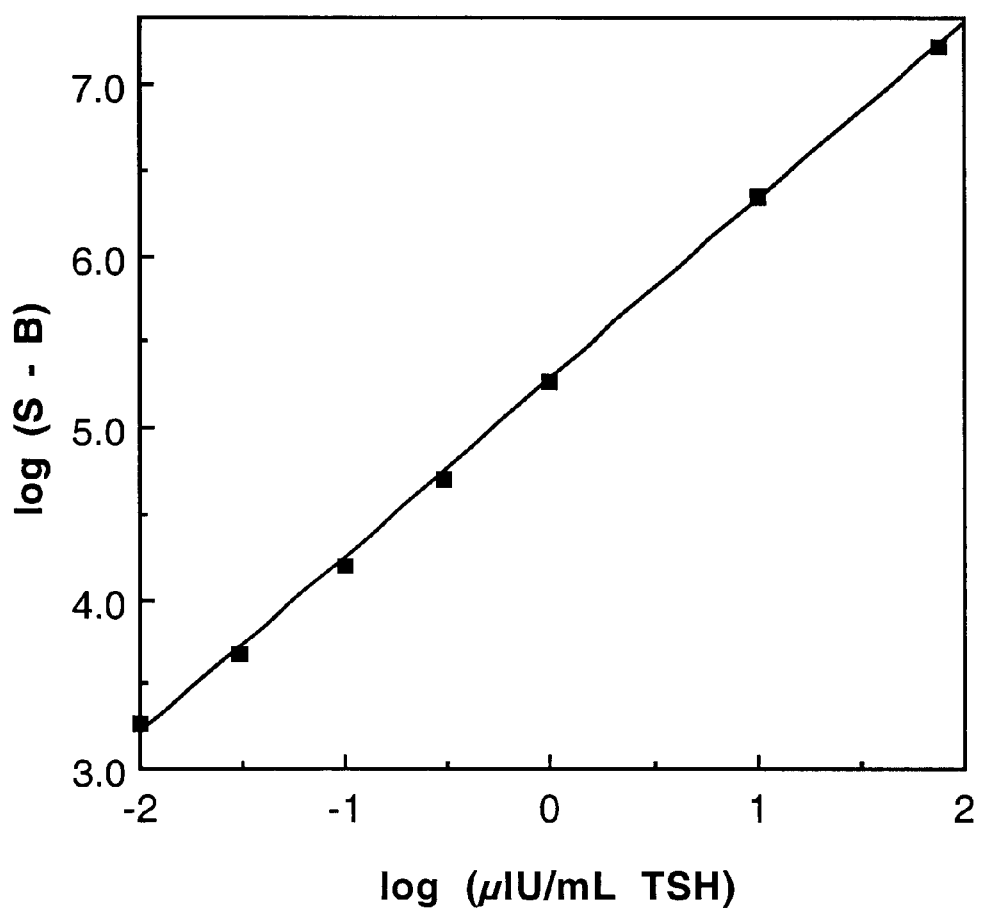
FIG. 14 is a graph showing the results of a rapid chemiluminescent immunoassay for thyroid stimulating hormone using a detection reagent of the invention.

Assay results as shown in FIG. 14 and Table 7 demonstrate the utility of the present compositions in providing a rapid assay.

Example 45

Chemiluminescent Immunoassay of TSH

A method for detection of TSH by chemiluminescent immunoassay was performed on the IMMULITE Automated Analyzer using an IMMULITE TSH Third Generation TSH Assay kit from Diagnostic Products Corp. according to the manufacturer's protocol with modifications as described in Example 43. Reagent A of Example 32 was substituted for the detection reagent supplied in the kit. Chemiluminescence measurements were made at 1.5 minutes after substrate introduction.

TABLE 8

IMMULITE Third Generation TSH Assay Data

| $\mu$IU/mL TSH | Intensity (CPS) | % CV |
|---|---|---|
| 75 | 25249293 | 1.6 |
| 10 | 4265600 | 1.5 |
| 1 | 415363 | 0.8 |
| 0.3 | 122580 | 4.3 |
| 0.1 | 54070 | 0.3 |
| 0.03 | 23810 | 3.7 |
| 0.01 | 17240 | 0.4 |
| 0.003 | 13900 | 1.7 |
| Blank | 12996 | 4.4 |

Figure 15:
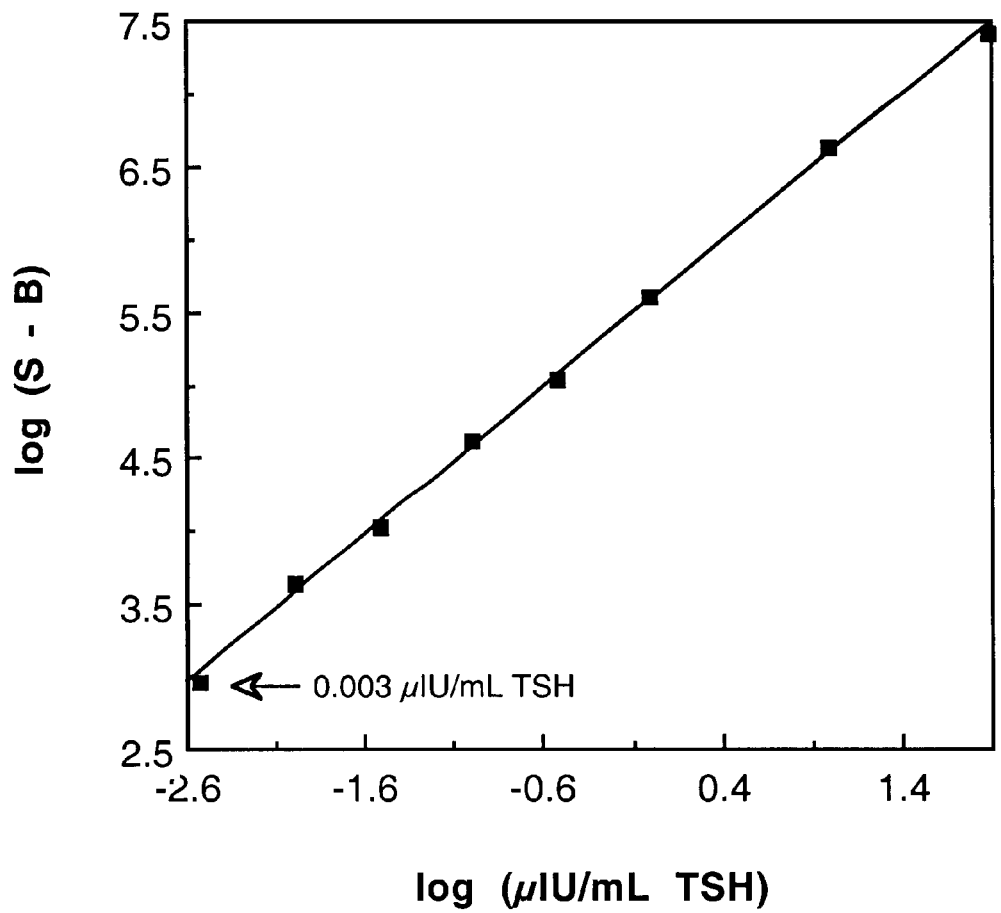
FIG. 15 is a graph showing the results of a chemiluminescent immunoassay for thyroid stimulating hormone using a detection reagent of the invention.

The assay results as shown in FIG. 15 and Table 8 demonstrate the utility of the present compositions in providing a highly sensitive assay.

Example 46

Chemiluminescent Immunoassay of Estradiol

A method for detection of estradiol by chemiluminescent immunoassay was performed on the IMMULITE Automated Analyzer using a kit supplied by Diagnostic Products Corp. according to the manufacturer's protocol with modifications as described in Example 43. Reagent A of Example 32 was substituted for the detection reagent supplied in the kit. Chemiluminescence measurements were made at 1.5 minutes after substrate introduction.

TABLE 9

IMMULITE E2 Estradiol Assay Data

| pg/mL Estradiol | Intensity (CPS) | % CV |
|---|---|---|
| 2000 | 500300 | 4.1 |
| 1000 | 783877 | 3.3 |
| 300 | 2521788 | 2.7 |
| 100 | 5398650 | 2.9 |
| 30 | 8808133 | 1.8 |
| 10 | 10036147 | 2.1 |
| Blank | 10536776 | 3.9 |

Figure 16:
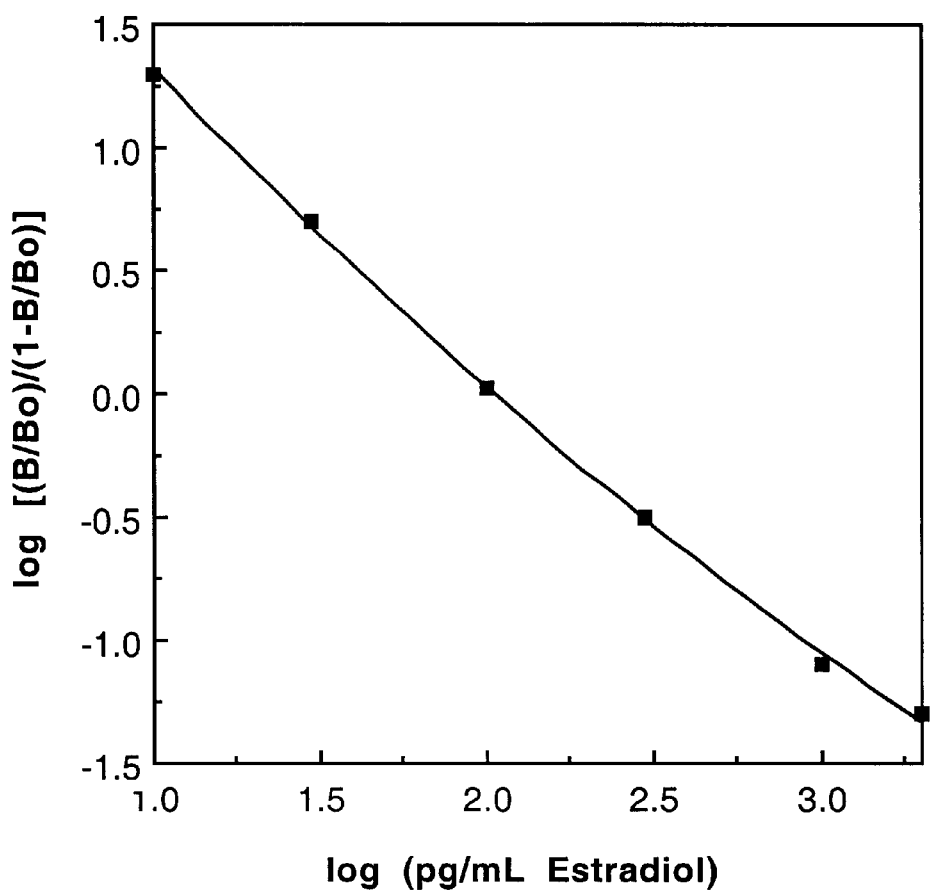
FIG. 16 is a graph showing the results of a chemiluminescent immunoassay for estradiol using a detection reagent of the invention.

The assay results as shown in FIG. 16 and Table 9 demonstrate the utility of the present compositions in competitive-type immunoassays.

Example 47

Chemiluminescent Detection of Acid Phosphatase (AcP)

Reagent A of Example 32 was used in an experiment to detect acid phosphatase. Reaction of 100 μL of this composition with AcP (Sigma AcP LIN-TROL, reconstituted to 2.0 mL, 83 U/L) at ambient temperature in a test tube housed in a Turner TD-20e luminometer produced chemiluminescence which reached maximum intensity within 2–5 sec and decayed to zero within 10–15 sec.

Figure 17:
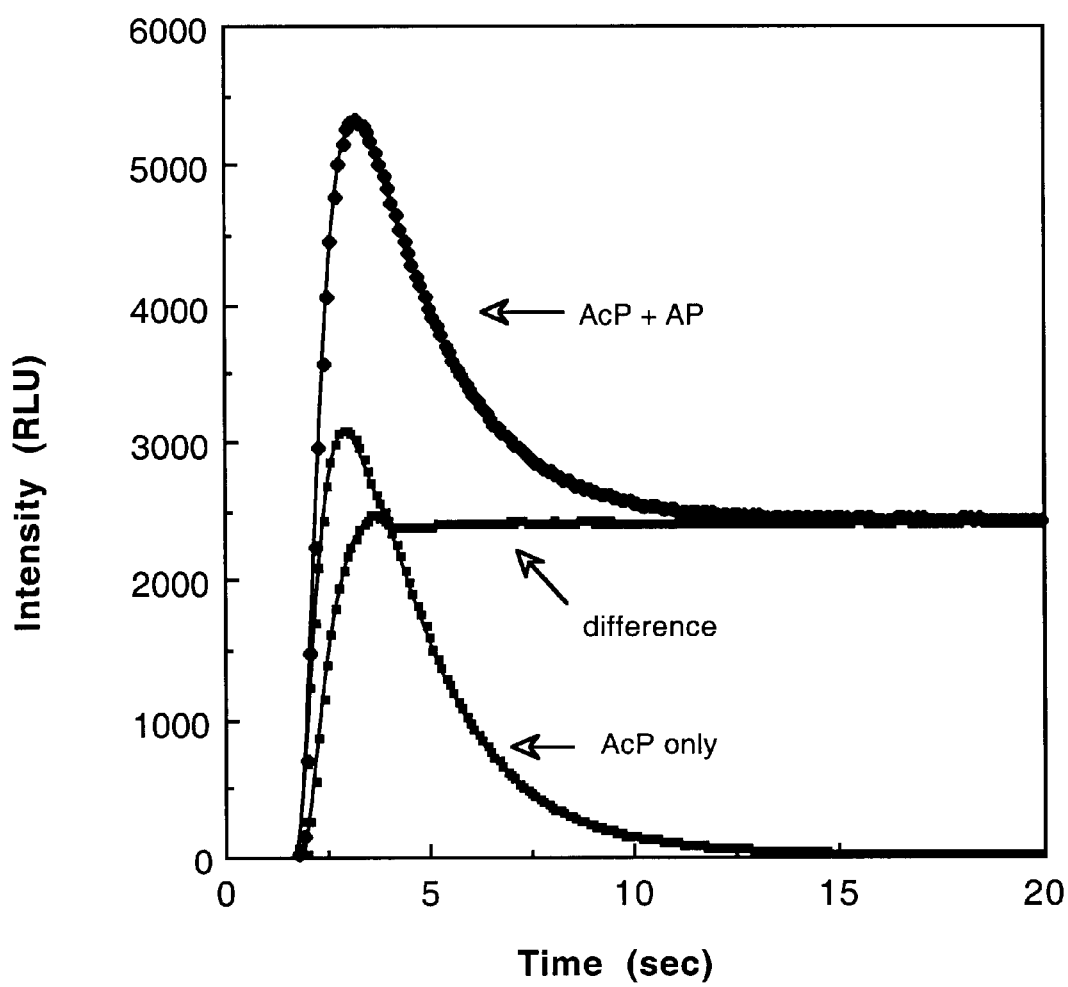
FIG. 17 is a plot demonstrating the ability to simultaneously detect acid phosphatase and alkaline phosphatase in one sample. The upper trace is the light emitted from a sample containing both enzymes, the lower trace is the light emitted from a sample containing only acid phosphatase and the middle trace represents the difference attributable to alkaline phosphatase.

Acid phosphatase could be measured in the presence of alkaline phosphatase by means of this detection reagent. Since the chemiluminescent signal induced by AcP decayed nearly completely within seconds, measuring the stable light intensity after about 15–20 sec allows discrimination of AP activity as shown in FIG. 17. This method allowed the simultaneous quantitation of both AcP and AP activity in the same sample in one experiment. AcP could be easily measured in human whole blood.

Example 48

Linearity and Sensitivity of Detection of AP using Compound 13

Figure 19:
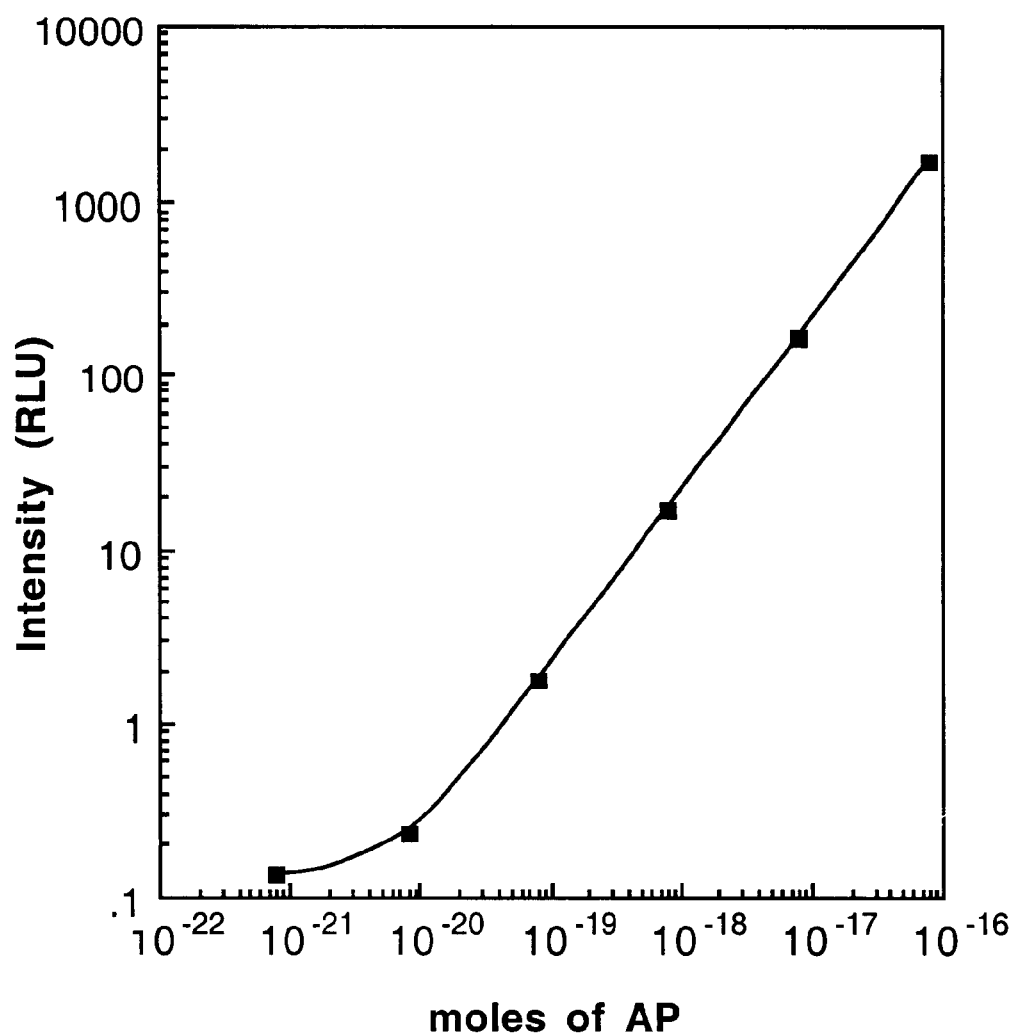
FIG. 19 is a graph relating the amount of AP to the maximum chemiluminescence intensity emitted by 100 µL of a reagent composition comprising 0.33 mM acridan phosphate 13 in 0.1 M tris buffer, pH 8,8, 3.2 µM lucigenin, 0.5 mg/mL sodium dodecyl sulfate, 0.005 mg/mL $Na_2SO_3$, 0.016% (w/v) TWEEN 20 and 5 µM $MgCl_2$. The composition was reacted with 10 µL of solutions of AP containing between $8 \times 10^{-15}$ and $8 \times 10^{-22}$ mol of enzyme or 10 µL of water as a reagent blank and measured after 75 sec at ambient temperature in the wells of a black microplate.

In the manner of Example 32, a reagents was prepared according to the composition below. To 100 μL portions of each of the reagent was added 10 μL dilutions of AP containing between $8 \times 10^{-16}$ mol and $8 \times 10^{-22}$ mol of enzyme or 10 μL of water for the reagent blank. Light intensity was measured at 75 sec. FIG. 19 depicts the results.

| Reagent |
|---|
| Compound 13, 0.33 mM |
| 0.1 M tris buffer, pH 8.8 |
| MgCl$_2$, 5 μM |
| lucigenin, 3.2 μM |
| SDS, 0.5 mg/mL |
| Na$_2$SO$_3$, 5 μg/mL |
| TWEEN 20, 0.15 mg/mL (w/v) |

Example 49

The following compounds have also been synthesized and found to provide chemiluminescence when reacted with AP:

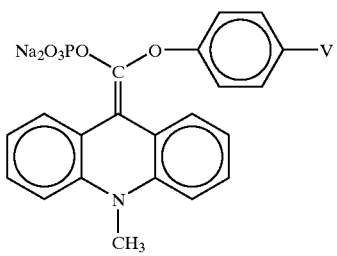

wherein V is t-butyl, CH$_3$, OCH$_3$F, Cl, Br, I, COCH$_3$, CN and NO$_2$ as well as compounds of the formula:

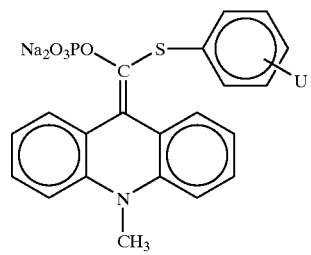

wherein U is p-I, p-CH, m-OCH$_3$, o-Cl, m-Cl, o-Br, m-Br, p-Br and p-NO$_2$ as well as compounds of this formula having a 3,4-dichloro-, 2,5-dichloro- and 2,6-dichlorophenyl group.

The foregoing description and examples are illustrative only and not to be considered as restrictive. It is recognized that modifications of the specific compounds and methods not specifically disclosed can be made without departing from the spirit and scope of the present invention. The scope of the invention is limited only by the appended claims.

What is claimed is:

1. A method for detecting an analyte in a sample by a chemiluminescent assay procedure which comprises:

(a) reacting a phosphatase enzyme with at least one compound of formula I to produce chemiluminescence for detecting the analyte,

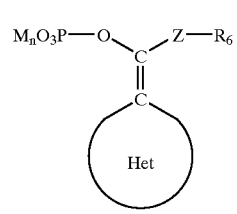

I wherein in the compound of formula I, Het is selected from the group consisting of:

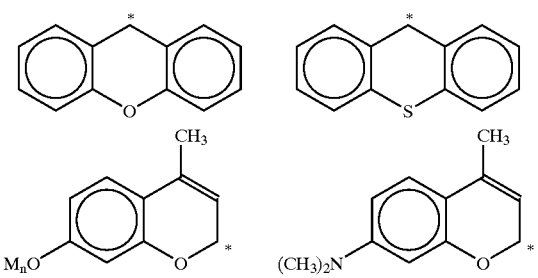

-continued

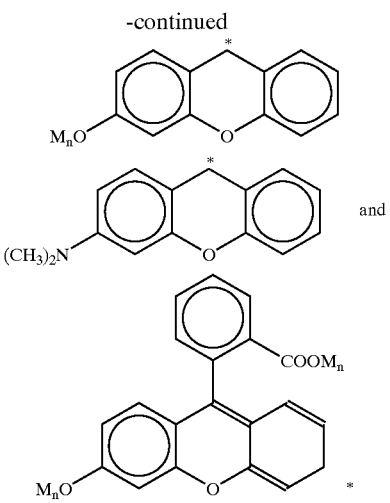

wherein * indicates the point of attachment of an enol phosphate group, wherein Z is selected from the group consisting of O and S atoms, wherein $R_6$ is selected from the group consisting of alkyl, substituted alkyl, aryl, substituted aryl and aralkyl groups, wherein each H is independently selected from H and a cationic center and wherein n is a number which satisfies electroneutrality;
   (b) detecting the chemiluminescence; and
   (c) relating the amount of the chemiluminescence to the amount of the analyte.
2. The method of claim 1 wherein the analyte to be detected is the phosphatase enzyme.
3. The method of claim 1 wherein the analyte to be detected is an inhibitor of the phosphatase enzyme.
4. The method of claim 1 further comprising reacting the analyte in the sample with an analyte binding compound which specifically binds with the analyte wherein the analyte-binding compound is labeled with alkaline phosphatase.
5. The method of claim 4 wherein the analyte-binding compound is selected from the group consisting of antibodies, antigens, haptens and nucleic acids.
6. The method of claim 1 further comprising reacting the analyte in the sample with:
   (a) a labeled analyte binding compound comprising an analyte binding compound which specifically binds with the analyte and at least one second specific binding substance; and
   (b) a phosphatase-labeled binding partner for the second specific binding substance.
7. The method of claim 1 wherein the detection is performed on a membrane.
8. The method of claim 7 wherein the membrane is selected from the group consisting of a nitrocellulose membrane, a polyvinylidene difluoride membrane and a nylon membrane.
9. The method of claim 1 further comprising providing the compound of formula I in a reagent composition comprising, in an aqueous solution, the compound of formula I and a surfactant enhancer in an amount effective to enhance the chemiluminescence.
10. The method of claim 9 wherein the surfactant enhancer is a copolymer of a vinylbenzyltributylphosphonium salt and a vinylbenzyltrioctylphosphonium salt.
11. The method of claim 1 further comprising:
   (a) reacting the compound of formula I with the phosphatase enzyme in a buffer at a first pH for a first period of time;

(b) adding a strongly basic trigger solution to the buffer solution to raise the pH of the buffer to a second pH for inducing the chemiluminescence; and
   (c) measuring the chemiluminescence.
12. The method of claim 11 wherein the first pH is in the range 5.0–9.51 wherein the pH of the trigger solution is greater than about 11 and the first period of time is from about 1 seconds to about 10 minutes.
13. The method of claim 11 wherein the basic trigger solution contains a surfactant enhancer.
14. The method of claim 13 wherein the enhancer is a copolymer of a vinylbenzyltributylphosphonium salt and a vinylbenzyltrioctylphosphonium salt.
15. A reagent composition which produces chemiluminescence in the presence of a phosphatase enzyme which comprises in an aqueous solution:
   a) a compound of formula I:

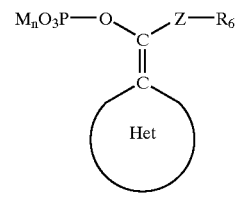

I which reacts with the phosphatase enzyme wherein Het is selected from the group consisting of:

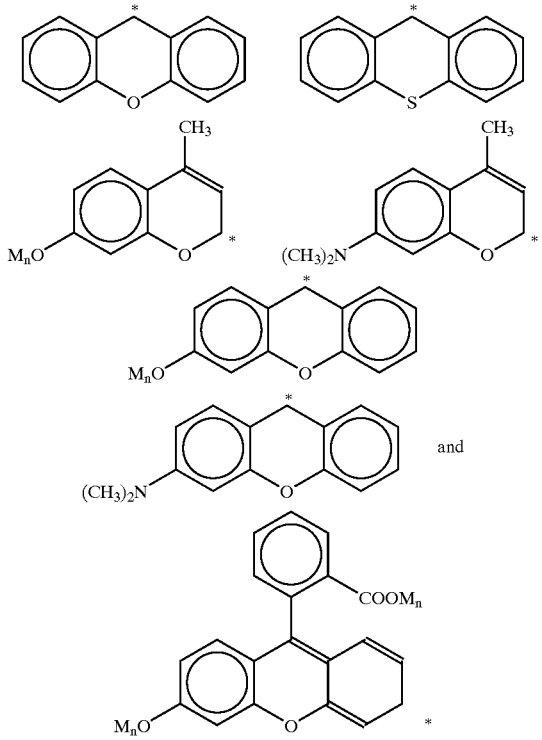

wherein * indicates the point of attachment of an enol phosphate group, wherein Z is selected from the group consisting of O and S atoms, wherein $R_6$ is selected from the group consisting of alkyl, substituted alkyl, aryl, substituted aryl and aralkyl groups, wherein each M is independently selected from H and a cationic center and wherein n is a number which satisfies electroneutrality; and b) a cationic aromatic compound in an amount effective to increase the chemiluminescence compared to that generated in the absence of the cationic aromatic compound.

16. The composition of claim 15 wherein the cationic aromatic compound is selected from the group consisting of cyanine dyes, carbocyanine dyes, azo dyes, acridinium derivatives, methylene blue, Nile Blue, IR-1040, lucigenin and paraquat dichloride.

17. The composition of claim 15 further comprising an anionic surfactant in an amount effective to increase the speed with which maximum chemiluminescence intensity is reached and a non-ionic surfactant in an amount effective to increase the amount of chemiluminescence.

18. The composition of claim 17 wherein the anionic surfactant is selected from alkylsulfates containing at least 10 carbon atoms and alkylsulfonates containing at least 10 carbon atoms.

19. The composition of claim 17 wherein the non-ionic surfactant is selected from polyoxyethylenated alkylphenols, polyoxyethylenated alcohols, polyoxyethylenated ethers and polyoxyethylenated sorbitol esters.

20. The composition of claim 17 additionally comprising a sulfite salt in an amount effective to reduce chemiluminescence produced by the composition in the absence of a phosphatase enzyme.

21. The composition of claim 18 wherein the anionic surfactant is sodium dodecyl sulfate.

22. The composition of claim 20 wherein the sulfite salt is sodium sulfite.

23. A method for producing chemiluminescence which comprises reacting a phosphatase enzyme with a) at least one compound of formula I:

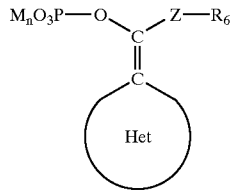

wherein Het is selected from the group consisting of:

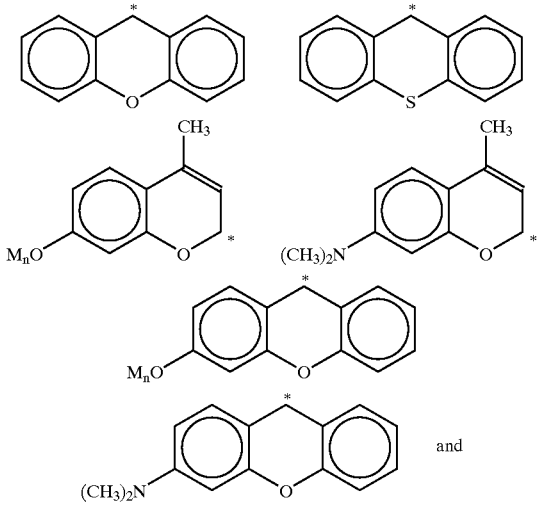

-continued

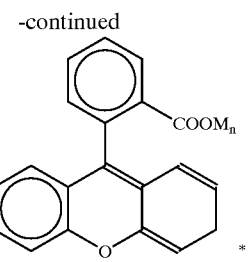

wherein * indicates the point of attachment of an enol phosphate group, wherein Z is selected from the group consisting of O and S atoms, wherein $R_6$ is selected from the group consisting of alkyl, substituted alkyl, aryl, substituted aryl and aralkyl groups, wherein each M is independently selected from H and a cationic center and wherein n is a number which satisfies electroneutrality; and b) a cationic aromatic compound in an amount effective to increase the chemiluminescence compared to that generated in the absence of the cationic aromatic compound.

24. The method of claim 23 wherein the phosphatase enzyme is selected from the group consisting of acterial alkaline phosphatase, mammalian alkaline phosphatase, plant acid phosphatase, mammalian acid phosphatase and alkaline phosphatase conjugates.

25. The method of claim 23 wherein the alkaline phosphatase conjugate comprises alkaline phosphatase linked to a biological molecule selected from the group consisting of haptens, antibodies, proteins, nucleic acids and oligonucleotides.

26. The method of claim 23 further comprising providing the compound of formula I and the cationic aromatic compound in a reagent composition which composition further comprises, in an aqueous solution, an anionic surfactant in an amount effective to increase the speed with which maximum chemiluminescence intensity is reached and a non-ionic surfactant in an amount effective to increase the chemiluminescence.

27. A method for detecting acid phosphatase and alkaline phosphatase in a sample suspected of containing both acid phosphatase and alkaline phosphatase by a chemiluminescent assay procedure which comprises:

(a) reacting the sample with a reagent composition comprising at least one compound of formula I,

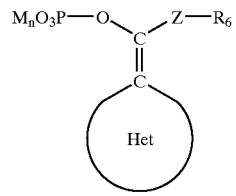

wherein in the compound of formula I, Het is selected from the group consisting of:

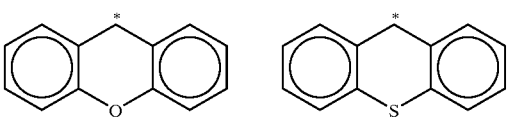

-continued

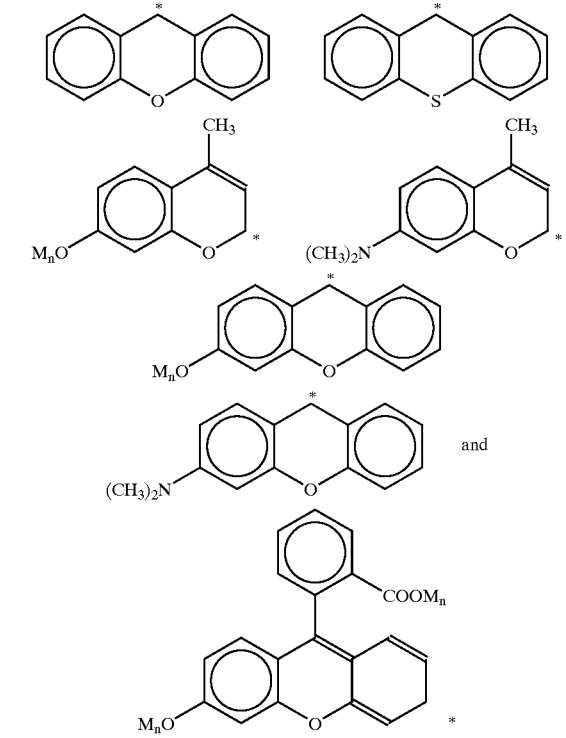

wherein Het is selected from the group consisting of:

wherein * indicates the point of attachment of an enol phosphate group, wherein Z is selected from the group consisting of O and S atoms, wherein $R_6$ is selected from the group consisting of alkyl, substituted alkyl, aryl, substituted aryl and aralkyl groups, wherein each M is independently selected from H and a cationic center and wherein n is a number which satisfies electroneutrality, a cationic aromatic compound, an anionic surfactant in an amount effective to increase the speed with which maximum chemiluminescence intensity is reached and a non-ionic surfactant in an amount effective to increase the chemiluminescence;

(b) detecting the amount or intensity of chemiluminescence during an initial period;

(c) waiting a second period of time until the chemiluminescence has achieved a constant level;

(d) detecting the amount or intensity of chemiluminescence during a third period;

(e) relating the chemiluminescence in the initial time period to the amount of acid phosphatase; and (f) relating the chemiluminescence in the third time period to the amount of alkaline phosphatase.

28. A process for the preparation of a compound of formula I:

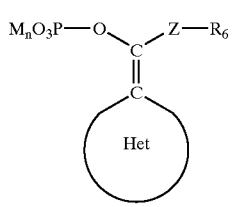

wherein Het, Z and are as defined for compound I with a base to form an enolate of VIII;

(b) reacting the enolate with a phosphorylating agent to form a protected enol phosphate IX having the formula:

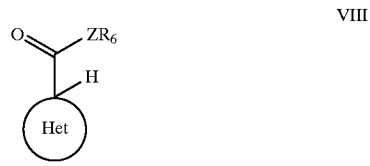

wherein Het, Z and $R_6$ are as defined above and Y is a protecting group; and (c) deprotecting the enol phosphate to form the enol phosphate salt compound I by reacting IX with at least one deprotecting agent in the presence of a cationic species M if the cationic species is not a part of the deprotecting agent.

29. The process of claim 28 wherein the step of reacting the enolate of compound VIII with a phosphorylating agent to form a protected enol phosphate IX comprises the steps of:

(a) reacting the enolate of compound VIII with a phosphorus oxyhalide compound $POW_3$, where W is a halogen atom selected from F, Cl, Br and I to form an enol dihalophosphate X having the formula

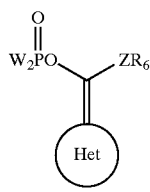

X wherein Het, Z and $R_6$ are as defined in compound VIII; and (b) reacting compound X with at least two equivalents of a hydroxylic compound Y—OH to form the protected enol phosphate IX.

30. The process of claim 28 wherein the step of reacting the enolate of compound VIII with a phosphorylating agent to form a protected enol phosphate IX comprises reacting the enolate of compound VIII with a phosphorylating agent containing the protecting groups Y and having the formula W—PO(OY)$_2$ and wherein W is a halogen atom selected from F, Cl, Br and I.

31. The process of claim 28 wherein the groups Y are selected from the group consisting of lower alkyl groups, substituted lower alkyl groups, phenyl, substituted phenyl and benzyl groups.

32. The process of claim 28 wherein the groups Y are connected to form the single group —$CH_2CH_2$—.

33. The process of claim 28 wherein the deprotecting agent is selected from the group consisting of organic and inorganic bases such as sodium hydroxide, potassium hydroxide, potassium carbonate, sodium methoxide, sodium ethoxide, potassium t-butoxide, ammonium hydroxide, nucleophilic agents such as cyanide ion, fluoride ion.

34. The process of claim 28 wherein Y is a $CH_2CH_2CN$ group and the deprotecting agent is selected from sodium hydroxide and sodium carbonate.

35. The process of claim 29 wherein Y is a $CH_2CH_2CN$ group and the deprotecting agent is selected from sodium hydroxide and sodium carbonate.

36. The method of claim 1 wherein the phosphatase enzyme is selected from the group consisting of bacterial alkaline phosphatase, mammalian alkaline phosphatase, plant acid phosphatase, mammalian acid phosphatase and alkaline phosphatase conjugates.

37. The method of claim 1 wherein M is selected from H, alkali metal ions, alkaline earth ions, quaternary ammonium ions and quaternary phosphonium ions.

38. The method of claim 1 wherein the compound of formula I is reacted with the phosphatase enzyme in the presence of a cationic aromatic compound.

39. The method of claim wherein the cationic aromatic compound is selected from the group consisting of cyanine dyes, carbocyanine dyes, azo dyes, acridinium derivatives, methylene blue, Nile Blue, IR-1040, lucigenin and paraquat dichloride.

40. The method of claim 38 further comprising providing the compound of formula I and the cationic aromatic compound in a reagent composition which composition further comprises, in an aqueous solution, an anionic surfactant in an amount effective to increase the speed with which maximum chemiluminescence intensity is reached and a non-ionic surfactant in an amount effective to increase the chemiluminescence.

41. The composition of claim 15 wherein M is selected from H, alkali metal ions, alkaline earth ions, quaternary ammonium ions and quaternary phosphonium ions.

42. The method of claim 23 wherein M is selected from H, alkali metal ions, alkaline earth ions, quaternary ammonium ions and quaternary phosphonium ions.

* * * * *